US010835152B2

(12) United States Patent
Jones et al.

(10) Patent No.: US 10,835,152 B2
(45) Date of Patent: Nov. 17, 2020

(54) ELECTROMECHANICAL PILL DEVICE WITH LOCALIZATION CAPABILITIES

(71) Applicant: PROGENITY, INC., San Diego, CA (US)

(72) Inventors: Mitchell Lawrence Jones, La Jolla, CA (US); Alain Labbe, St-Philippe (CA); Mark Sasha Drlik, Victoria (CA); Christian Terry Proch McMechan, Victoria (CA)

(73) Assignee: Progenity, Inc., San Diego, CA (US)

( * ) Notice: Subject to any disclaimer, the term of this patent is extended or adjusted under 35 U.S.C. 154(b) by 834 days.

(21) Appl. No.: 15/514,413

(22) PCT Filed: Sep. 25, 2015

(86) PCT No.: PCT/US2015/052500
§ 371 (c)(1),
(2) Date: Mar. 24, 2017

(87) PCT Pub. No.: WO2016/049602
PCT Pub. Date: Mar. 31, 2016

(65) Prior Publication Data
US 2017/0296092 A1 Oct. 19, 2017

Related U.S. Application Data

(60) Provisional application No. 62/055,244, filed on Sep. 25, 2014.

(51) Int. Cl.
A61B 5/06 (2006.01)
A61B 5/07 (2006.01)
(Continued)

(52) U.S. Cl.
CPC .............. A61B 5/065 (2013.01); A61B 1/041 (2013.01); A61B 5/002 (2013.01); A61B 5/0086 (2013.01);
(Continued)

(58) Field of Classification Search
CPC ....... A61B 5/065; A61B 5/7264; A61B 5/002; A61B 5/6861; A61B 5/0086; A61B 5/073;
(Continued)

(56) References Cited

U.S. PATENT DOCUMENTS 3,057,344 A 10/1962 Alberto
3,118,439 A 1/1964 Barana
(Continued)

FOREIGN PATENT DOCUMENTS

CN 103209632 7/2013
EP 108607 2/1983
(Continued)

OTHER PUBLICATIONS

Chinese Office Action in Application No. 2015800635638, dated Sep. 29, 2019, 10 pages.
(Continued)

Primary Examiner — Peter Luong
(74) Attorney, Agent, or Firm — Fish & Richardson P.C.

(57) ABSTRACT

Various embodiments are described herein for a device, system, and method for identifying a location of an ingestible device within a gastrointestinal tract of a body. In some embodiments, the ingestible device includes a sensing unit with an axial optical sensing sub-unit located proximal to at least one end of the device, and a radial optical sensing sub-unit located proximal to a radial wall of the device, and may autonomously identify a location within the gastrointestinal tract. In some embodiments, the ingestible device
(Continued)

includes optical illumination sources and detectors that operate at a plurality of different wavelengths, and may discern regions of a gastrointestinal tract by using the reflection properties of organ tissue and occasional particulates. In some embodiments, the ingestible device may sample fluid or release medicament based on a detected device location.

37 Claims, 44 Drawing Sheets

(51) Int. Cl.
    *A61B 5/00*     (2006.01)
    *A61B 1/04*     (2006.01)
    *H04B 13/00*     (2006.01)
    *H04B 10/114*     (2013.01)

(52) U.S. Cl.
    CPC ............ *A61B 5/073* (2013.01); *A61B 5/6861* (2013.01); *A61B 5/7264* (2013.01); *H04B 10/1143* (2013.01); *H04B 13/00* (2013.01); *A61B 5/0017* (2013.01); *A61B 2560/0443* (2013.01); *A61B 2560/0462* (2013.01); *A61B 2562/162* (2013.01)

(58) Field of Classification Search
    CPC .......... A61B 5/0017; A61B 2560/0443; A61B 2560/0462; A61B 2562/162; H04B 13/00; H04B 10/1143
    See application file for complete search history.

(56) References Cited

U.S. PATENT DOCUMENTS

| | | | |
|---|---|---|---|
| 3,315,660 A | 4/1967 | Abella |
| 3,485,235 A | 12/1969 | Felson |
| 4,223,680 A | 9/1980 | Jobsis |
| 4,239,040 A | 12/1980 | Hosoya |
| 4,292,961 A | 10/1981 | Kawashima |
| 4,425,117 A | 1/1984 | Hugeman |
| 4,507,115 A | 3/1985 | Kambara |
| 4,573,447 A | 3/1986 | Thrash et al. |
| 4,844,076 A | 7/1989 | Lesho |
| 5,170,801 A | 12/1992 | Casper |
| 5,279,607 A | 1/1994 | Schentag |
| 5,395,366 A | 3/1995 | Andrea |
| 5,604,531 A | 2/1997 | Iddan et al. |
| 5,858,001 A | 1/1999 | Tsals et al. |
| 5,951,538 A | 9/1999 | Joshi |
| 5,984,860 A | 11/1999 | Shan |
| 6,082,366 A | 7/2000 | Andra et al. |
| 6,344,027 B1 | 2/2002 | Goll |
| 6,428,469 B1 | 8/2002 | Iddan et al. |
| 6,576,429 B1 | 6/2003 | Hallgren |
| 6,632,216 B2 | 10/2003 | Houzego |
| 7,056,673 B2 | 6/2006 | Kamme et al. |
| 7,553,276 B2 | 6/2009 | Iddan |
| 7,611,480 B2 | 11/2009 | Levy |
| 7,797,033 B2 | 9/2010 | D'Andrea et al. |
| 8,185,185 B2 | 5/2012 | Gilreath |
| 8,206,285 B2 | 6/2012 | Blijevsky |
| 8,394,034 B2 | 3/2013 | Iddan |
| 8,540,623 B2 | 9/2013 | Blijevsky |
| 8,626,268 B2 | 1/2014 | Adler |
| 8,696,602 B2 | 4/2014 | Semler et al. |
| 8,911,368 B2 | 12/2014 | Rabinovitz et al. |
| 9,026,192 B2 | 5/2015 | Blit et al. |
| 9,131,842 B2 | 9/2015 | Old |
| 9,324,145 B1 | 4/2016 | Cherevatsky |
| 1,058,860 A1 | 3/2020 | Jones et al. |
| 2001/0035902 A1 | 11/2001 | Iddan et al. |
| 2002/0099310 A1 | 7/2002 | Kimchy et al. |
| 2003/0139661 A1 | 7/2003 | Kimchy |
| 2003/0191430 A1 | 10/2003 | Andrea et al. |
| 2004/0253304 A1 | 12/2004 | Gross et al. |
| 2004/0254455 A1 | 12/2004 | Iddan |
| 2005/0010168 A1 | 1/2005 | Kendall |
| 2005/0049462 A1* | 3/2005 | Kanazawa ......... A61B 1/00096 600/170 |
| 2005/0065441 A1* | 3/2005 | Glukhovsky .......... A61B 1/041 600/476 |
| 2005/0158246 A1 | 7/2005 | Takizawa |
| 2005/0266074 A1 | 12/2005 | Zilberstein et al. |
| 2006/0069317 A1 | 3/2006 | Horn et al. |
| 2006/0178557 A1 | 8/2006 | Mintchev |
| 2007/0027362 A1* | 2/2007 | Handa ................ A61B 1/00009 600/160 |
| 2007/0043320 A1 | 2/2007 | Kenany |
| 2007/0092401 A1 | 4/2007 | Liao et al. |
| 2007/0161928 A1 | 7/2007 | Sprenkels |
| 2007/0293736 A1 | 12/2007 | Casset |
| 2008/0027329 A1 | 1/2008 | Glukhovsky |
| 2008/0051633 A1 | 2/2008 | Blijevsky |
| 2008/0194912 A1 | 8/2008 | Trovato |
| 2008/0208077 A1 | 8/2008 | Iddan et al. |
| 2008/0234548 A1* | 9/2008 | Amit .................... A61B 1/0638 600/160 |
| 2008/0294023 A1 | 11/2008 | Rabinovitz et al. |
| 2009/0131784 A1 | 5/2009 | Betesh |
| 2010/0045786 A1 | 2/2010 | Kitamura |
| 2010/0111763 A1 | 5/2010 | Kahn et al. |
| 2010/0285475 A1 | 11/2010 | Palanisanny |
| 2011/0046458 A1 | 2/2011 | Pinedo |
| 2011/0125007 A1 | 5/2011 | Steinberg |
| 2011/0125031 A1 | 5/2011 | Blit et al. |
| 2011/0306055 A1 | 12/2011 | Haince |
| 2011/0313348 A1 | 12/2011 | Potter et al. |
| 2012/0136209 A1 | 5/2012 | Kostenich et al. |
| 2012/0258473 A1 | 10/2012 | Moriya et al. |
| 2013/0013031 A1 | 1/2013 | Ben-Yehuda et al. |
| 2013/0018279 A1 | 1/2013 | Plante et al. |
| 2013/0022983 A1 | 1/2013 | Grifantini |
| 2013/0085414 A1 | 4/2013 | Yamatani |
| 2013/0158344 A1 | 6/2013 | Taniguchi |
| 2014/0113313 A1 | 4/2014 | Moreau |
| 2014/0128833 A1 | 5/2014 | Vogt |
| 2014/0206956 A1 | 7/2014 | Rabinovitz et al. |
| 2014/0296666 A1 | 10/2014 | Rabinovitz et al. |
| 2014/0343451 A1 | 11/2014 | Pannell |
| 2015/0011874 A1 | 1/2015 | Amoako-Tuffour et al. |
| 2015/0057548 A1 | 2/2015 | Kaufman |
| 2016/0033373 A1 | 2/2016 | Hill et al. |
| 2016/0038086 A1 | 2/2016 | Wrigglesworth |
| 2016/0066855 A1 | 3/2016 | Hyde |
| 2016/0213234 A1 | 7/2016 | Poon |
| 2016/0249793 A1 | 9/2016 | Wang |
| 2017/0006202 A1 | 1/2017 | Otani |
| 2017/0246438 A1 | 8/2017 | Aran et al. |
| 2017/0258583 A1 | 9/2017 | McCawley |
| 2018/0049725 A1 | 2/2018 | Jones et al. |
| 2018/0052084 A1 | 2/2018 | Jones et al. |
| 2018/0070857 A1 | 3/2018 | Jones et al. |
| 2018/0160950 A1 | 6/2018 | Rabinovitz et al. |
| 2018/0279908 A1 | 10/2018 | Jones et al. |
| 2020/0245897 A1 | 8/2020 | Jones et al. |

FOREIGN PATENT DOCUMENTS

| | | |
|---|---|---|
| EP | 1243524 | 9/2002 |
| EP | 1530950 | 5/2005 |
| EP | 1932462 | 6/2008 |
| EP | 2 057 934 | 5/2009 |
| EP | 3 108 810 | 12/2016 |
| JP | 2005-73888 | 3/2005 |
| JP | 2013-500815 | 1/2013 |
| JP | 2015-509744 | 4/2015 |
| KR | 100931946 | 12/2009 |
| WO | WO 2001045552 | 6/2001 |
| WO | WO 2010/091926 | 8/2010 |
| WO | WO 2010/146588 | 12/2010 |

(56) References Cited

FOREIGN PATENT DOCUMENTS

| WO | WO 2011/016002 | 2/2011 |
|---|---|---|
| WO | WO 2013/088444 | 6/2013 |
| WO | WO 2013120184 | 8/2013 |
| WO | WO 2015059569 | 4/2015 |
| WO | WO 2015/099749 | 7/2015 |
| WO | WO 2015147305 | 10/2015 |
| WO | WO 2016054015 | 4/2016 |
| WO | WO 2017004000 | 1/2017 |
| WO | WO 2016/049602 | 3/2018 |
| WO | WO 2018050647 | 3/2018 |

OTHER PUBLICATIONS

Steven L. Jacques, "Optical properties of biological tissues: a review," Phys., Med. Biol., IPEM, 58, R37, 28 pages, 2013.
European Exam Report in Application No. 15775911.9, dated Jan. 2, 2020, 4 pages.
Eurasian Office Action in Application No. 201790706/31, dated May 29, 2019, 4 pages, (with English Translation).
International Search Report and Written Opinion in International Application No. PCT/US2015/052500, dated Dec. 17, 2015, 15 pages.
Australian Office Action in Application No. 2015319850, dated Aug. 2, 2019, 4 pages.
European Exam Report in Application No. 157759119.9, dated May 28, 2018, 3 pages.
European Exam Report in Application No. 157759119.9, dated Mar. 3, 2019, 4 pages.
Japanese Office Action in Application No. 2017-516962, dated Jul. 22, 2019, 4 pages.
Invitation to Pay Fees om International Application No. PCT/US2018/025191, dated Jul. 12, 2018, 22 pages.
Chen et al., "Developing assessment system for wireless capsule endoscopy videos based on event detection", Proceedings of SPIE, vol. 7260, p. 72601G, 2009.
International Search Report and Written Opinion in International Application No. PCT/US2018/025191, dated Oct. 19, 2018.
Lee et al., "Automatic classification of digestive organs in wireless capsule endoscopy videos", Applied Computing 2007. The 22nd Annual ACM Symposium on Applied Computing, 1041-1045, 2007.
Anselmo et al., "Non-invasive delivery strategies for biologics", Nature Reviews, Drug Discovery, vol. 18, 19-40, 2019.
Aran et al., "An oral microjet vaccination system elicits antibody production in rabbits", Sci. Transl. Med. 9, eaaf6413, 10 pages, 2017.
Barolet et al., "Current trends in needle-free jet injection: an update", Clinical, Cosmetic and Investigational Dermatology, 11, 231-238, 2018.
Battula et al., "A Miniature Shock Wave Driven Micro-Jet Injector for Needle-Free Vaccine/Drug Delivery", Biotechnology and Bioengineering, vol. 113, No. 11, 2507-2512, 2016.
Dingle et al., "Stable and Noncompetitive RNA Internal Control for Routine Clinical Diagnostic Reverse Transcription-PCR", Journal of Clinical Microbiology, vol. 42(3): 1003-1011, Mar. 2004.

Hunter et al., "Aerosol delivery of Virus-like Particles to the genital tract induces local and systemic antibody responses", Vaccine, 29(28): 4584-4592, 2011.
International Search Report and Written Opinion in International Application No. PCT/US2017/050642, dated Jan. 29, 2018, 28 pages.
International Search Report Written Opinion. International Application No. PCT/US2017/047476, dated Jan. 22, 2018, 20 pages.
International Search Report Written Opinion. International Application No. PCT/US2017/047481, dated Jan. 17, 2018, 18 pages.
Invitation to Pay Additional Fees and Where Applicable Protest Fee International Application No. PCT/US2012/047476, dated Nov. 13, 2017, 13 pages.
Invitation to Pay Additional Fees and Where Applicable Protest Fee International Application No. PCT/US2017/050642, dated Dec. 8, 2017, 25 pages.
Invitation to Pay Additional Fees for International Application No. PCT/US2017/047481, dated Nov. 24, 2017, 14 pages.
Iverson et al., "An innate antiviral pathway acting before interferons at epithelial surfaces", Nature Immunology, vol. 17, No. 2, 150-158, 2016.
Kale et al., "Needle free injection technology—An overview", Innovations in pharmacy, vol. 1, No. 1, Article 148, 10 pages, 2014.
Kane et al., "Fecal Lactoferrin is a Sensitive and Specific Marker in Identifying Intestinal Inflammation", The American Journal of Gastroenterology, 98(6): 1309-1314, 2003.
Kostic et al., "The Gut Microbiome and Disease", Gastroenterology, vol. 146(6): 1489-1499, 2014.
Lambert et al., "Autonomous telemetric capsule to explore the small bowel," Med Biol Eng Comput 29(2): 191-196, 1991.
Lehmann et al.,"The role and utility of faecal markers in inflammatory bowel disease", Therapeutic Advances in Gastroenterology, vol. 8(1): 23-36, 2015.
Lo et al., "The use of carbon dioxide in gastrointestinal endoscopy", Gastrointestinal Endoscopy, vol. 83, No. 5, 857-865, 2016.
Sanschagrin and Yergeau, Next-generation Sequencing of 16S Ribosomal RNA Gene Amplicons, Journal of Visualized Exoeriments, Issue 90: 51709, Aug. 2014.
Sartor and Mazmanian, "Intestinal Microbes in Inflammatory Bowel Diseases", The American Journal of Gastroenterology Suoolements, vol. 1, 12-21, 2012.
U.S. Final Office Action in U.S. Appl. No. 15/680,400, dated Jan. 15, 2020, 14 pages.
U.S. Non-Final Office Action in U.S. Appl. No. 15/680,400, dated Mar. 5, 2020, 18 pages.
U.S. Non-Final Office Action in U.S. Appl. No. 15/680,400, dated Oct. 1, 2019, 11 pages.
U.S. Non-Final Office Action in U.S. Appl. No. 15/940,407, dated Jun. 15, 2020, 17 pages.
Wright et al., "Recent Advances in Characterizing the Gastrointestinal Microbiome in Crohn's Disease: A Systematic Review", Inflammatory Bowel Disease Journal, vol. 21(6): 1219-1228, 2015.
Bao and Pahlavan, "Motion estimation of the endoscopy capsule using region-based kernel SVM classifier," 2013 IEEE International. Conf. Electro-Information Technol., EIT 2013, 5 pages.
Li et al., "Outlier detection and removal improves accuracy of machine learning approach to multispectral burn diagnostic imaging," J. Biomed. Opt., 2015, 20:121305.

* cited by examiner

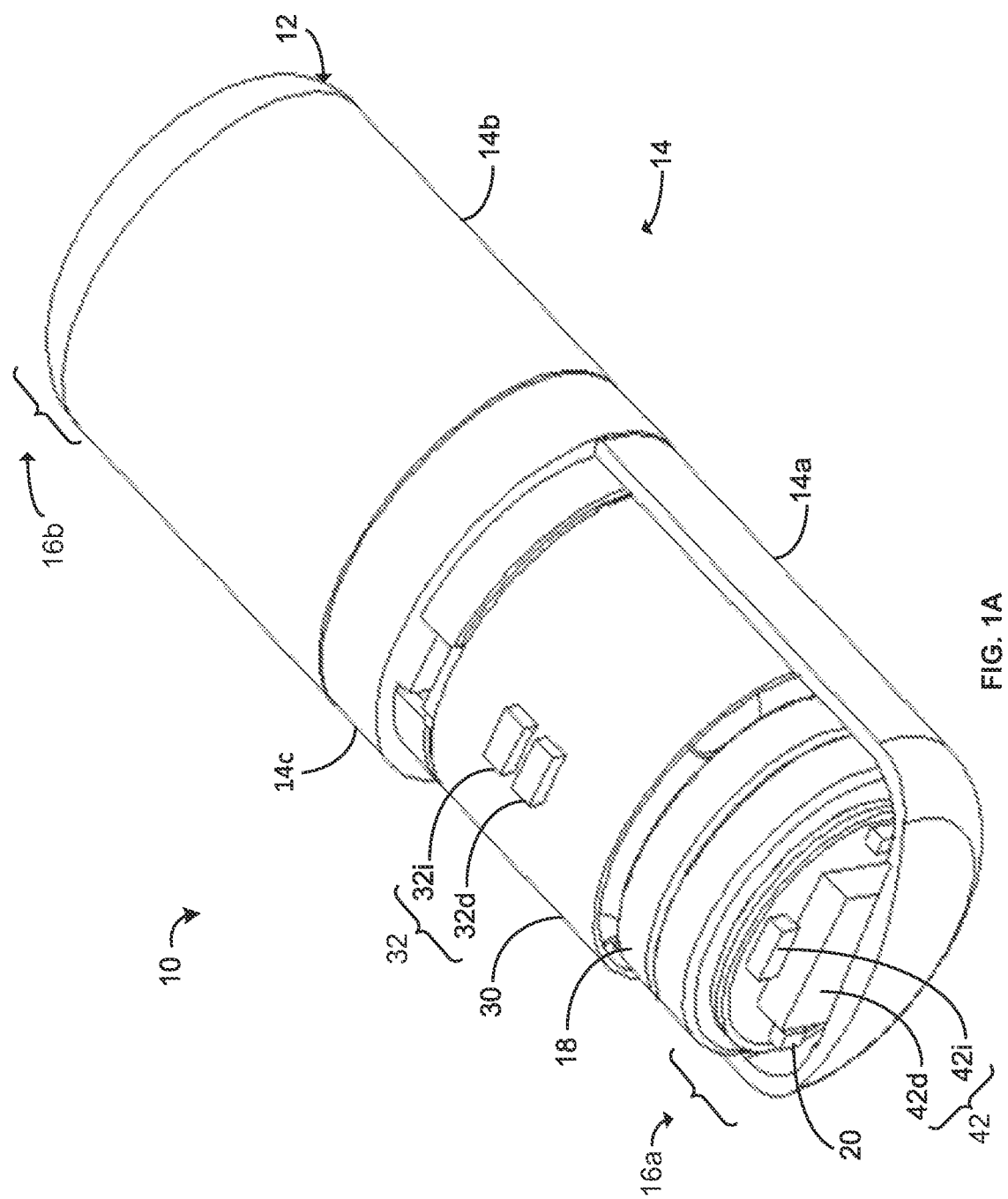

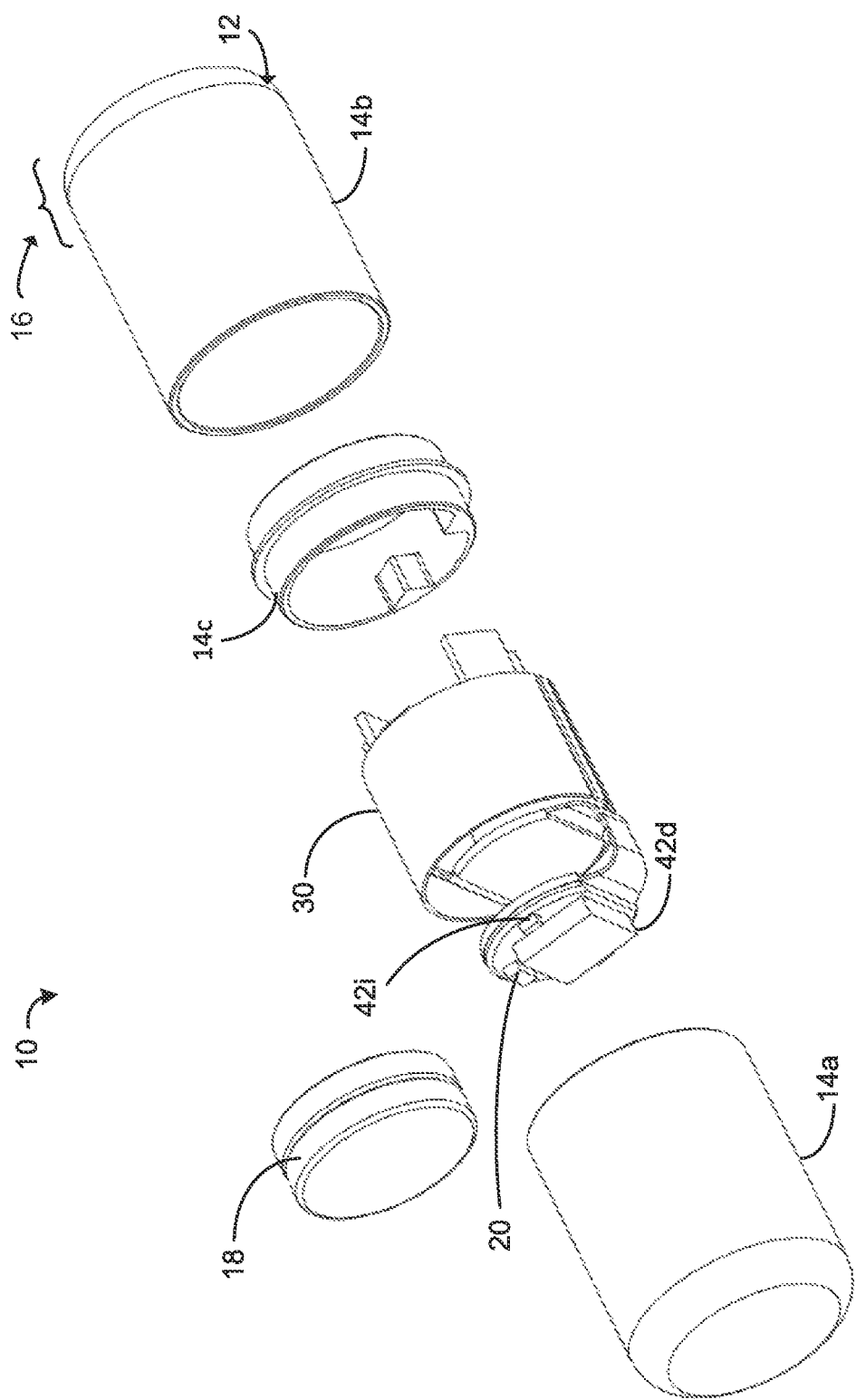

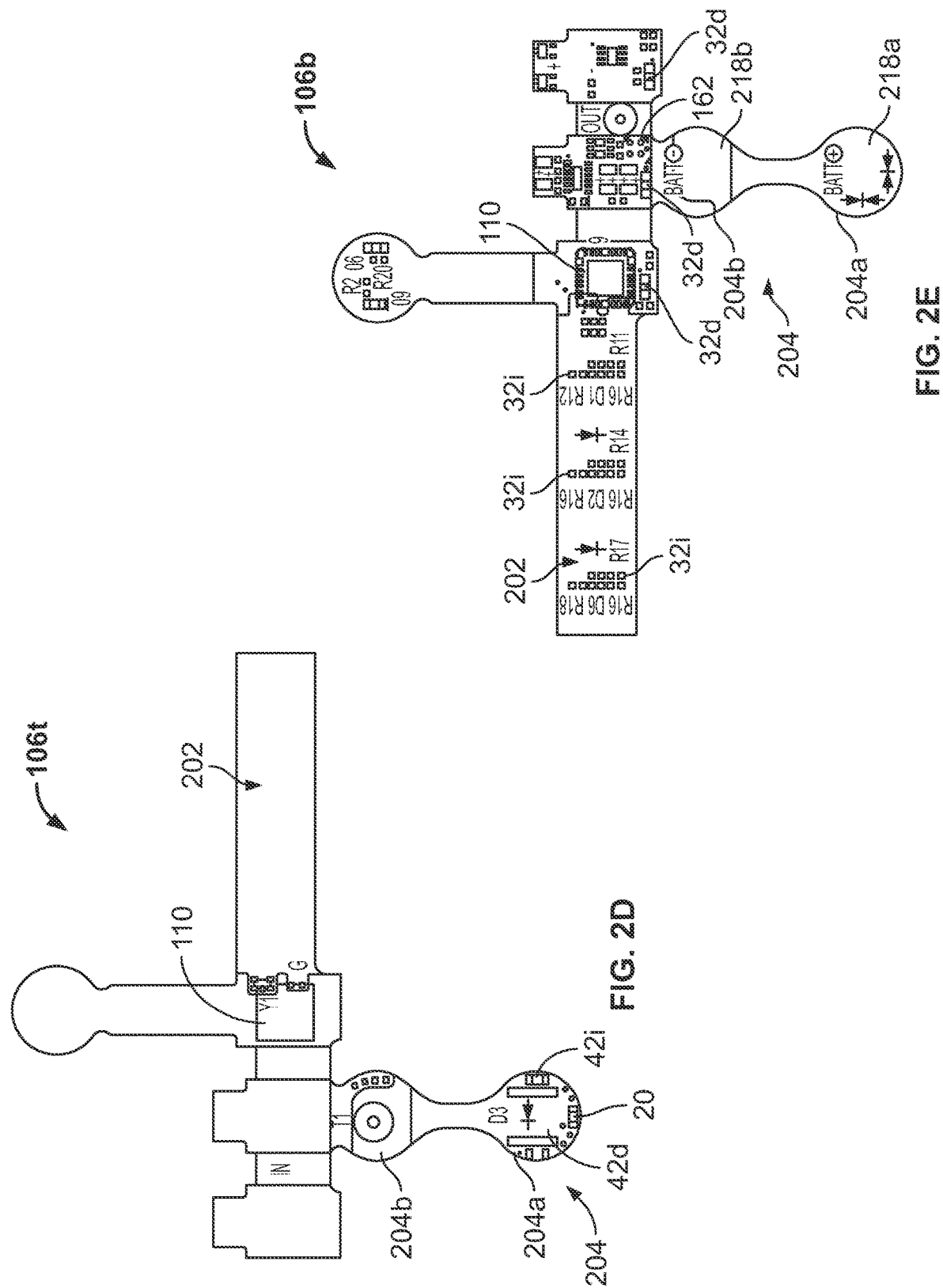

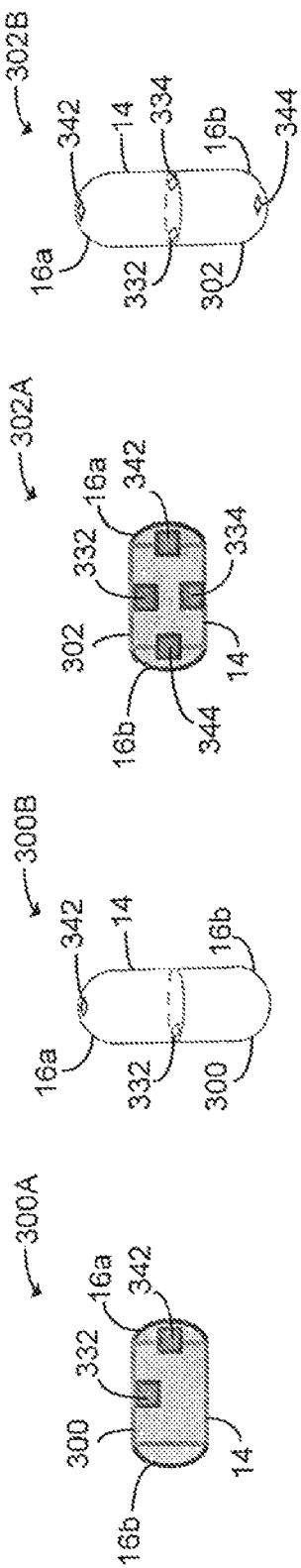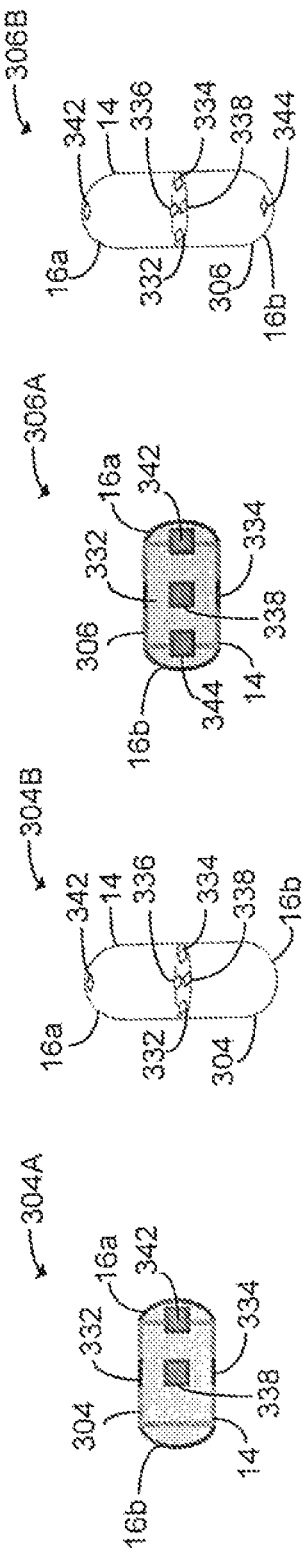

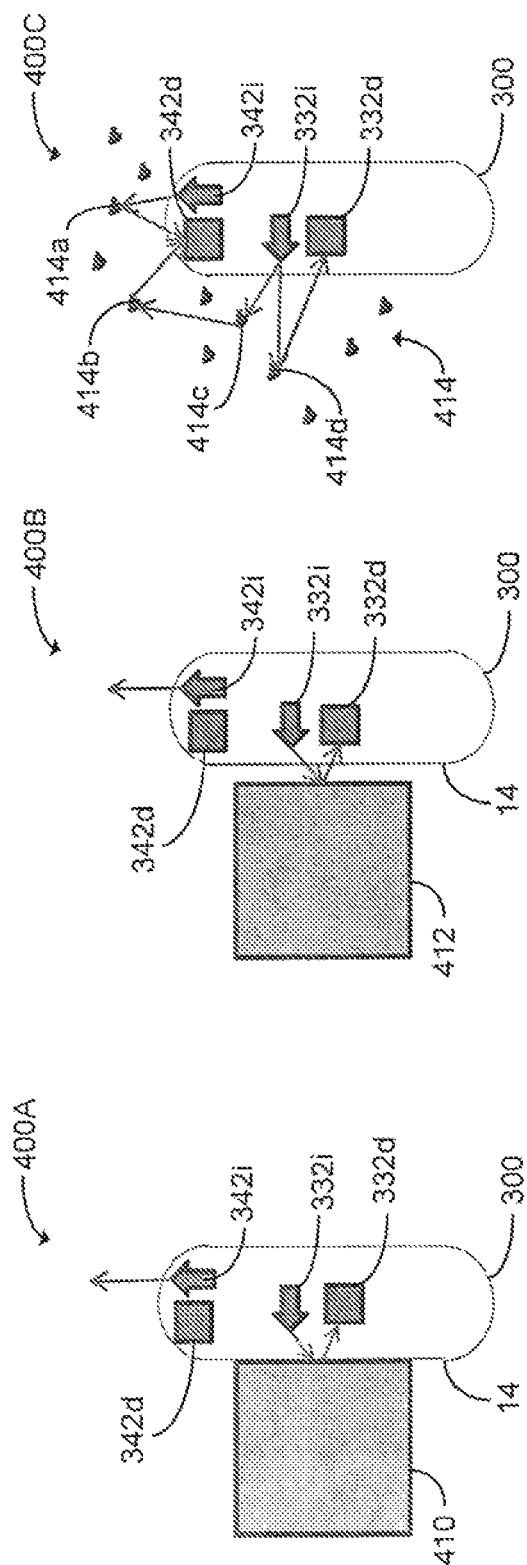

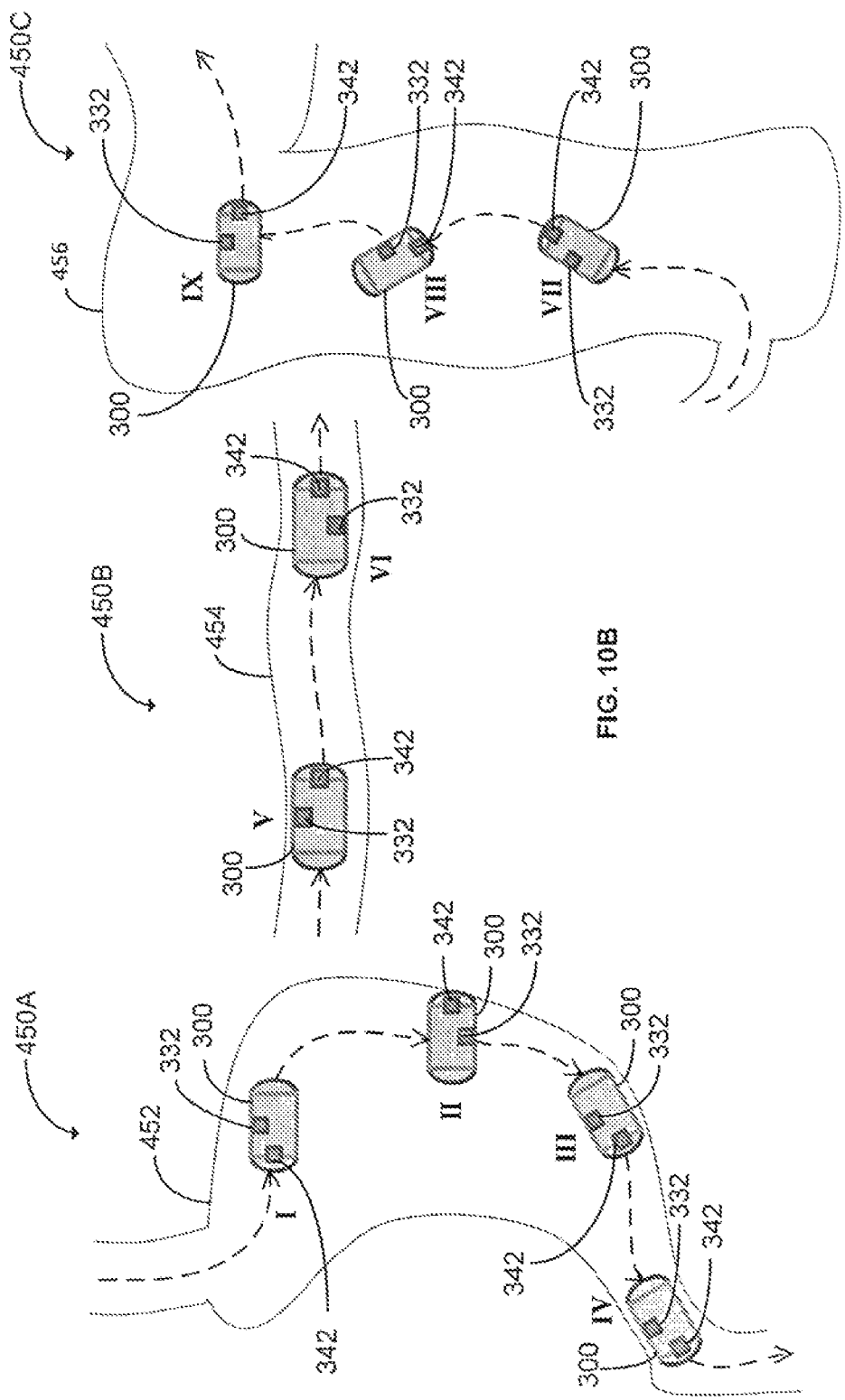

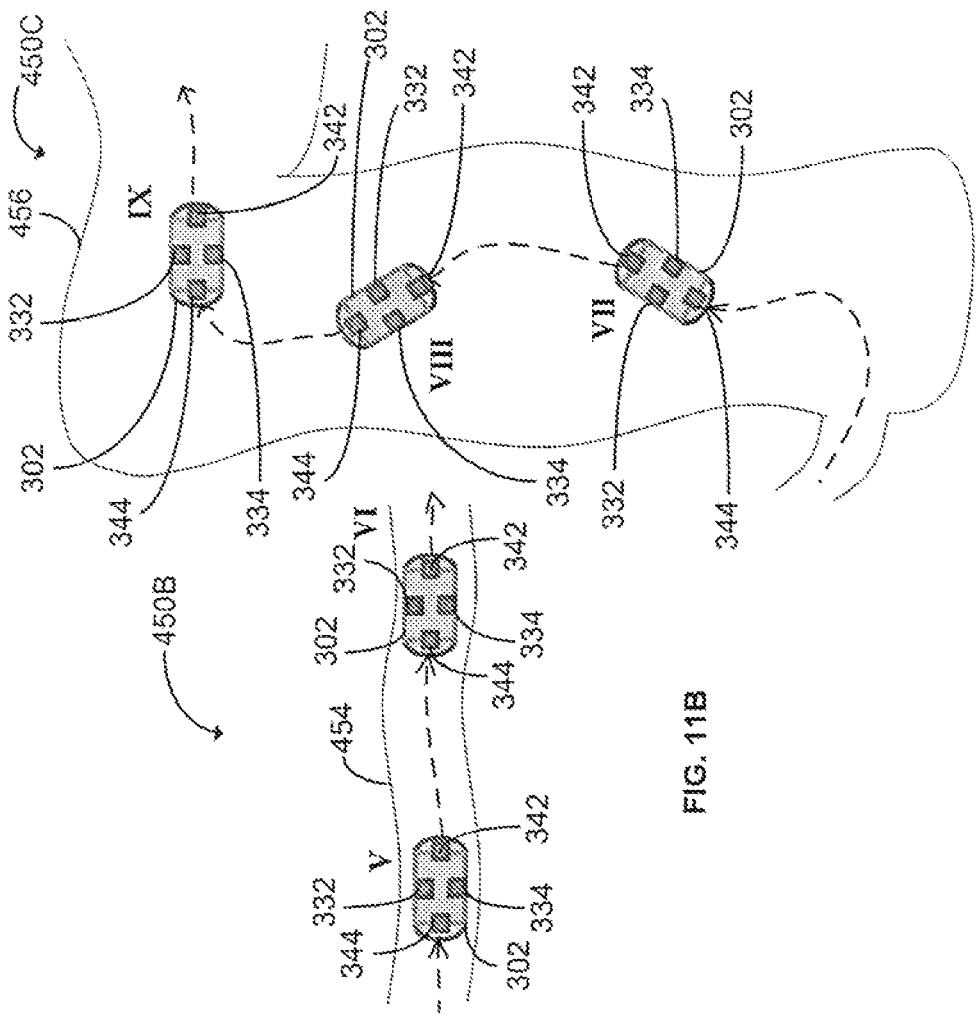
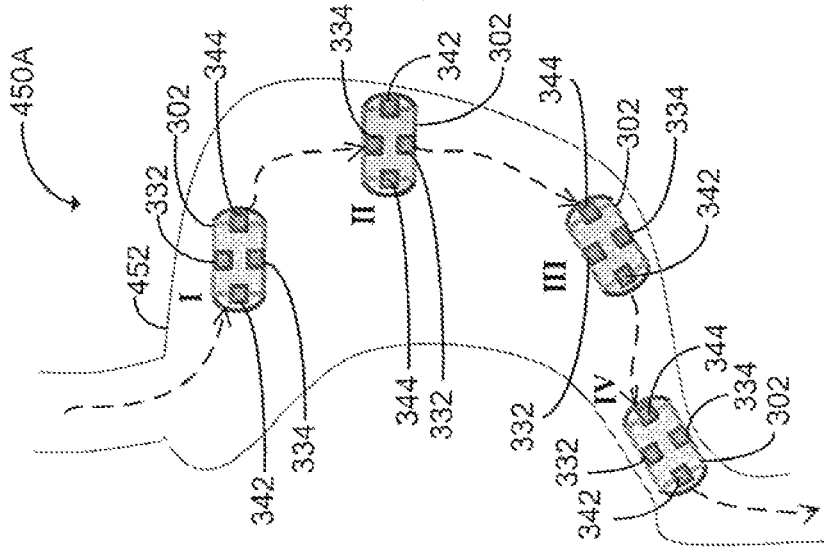
FIG. 11A  FIG. 11B  FIG. 11C

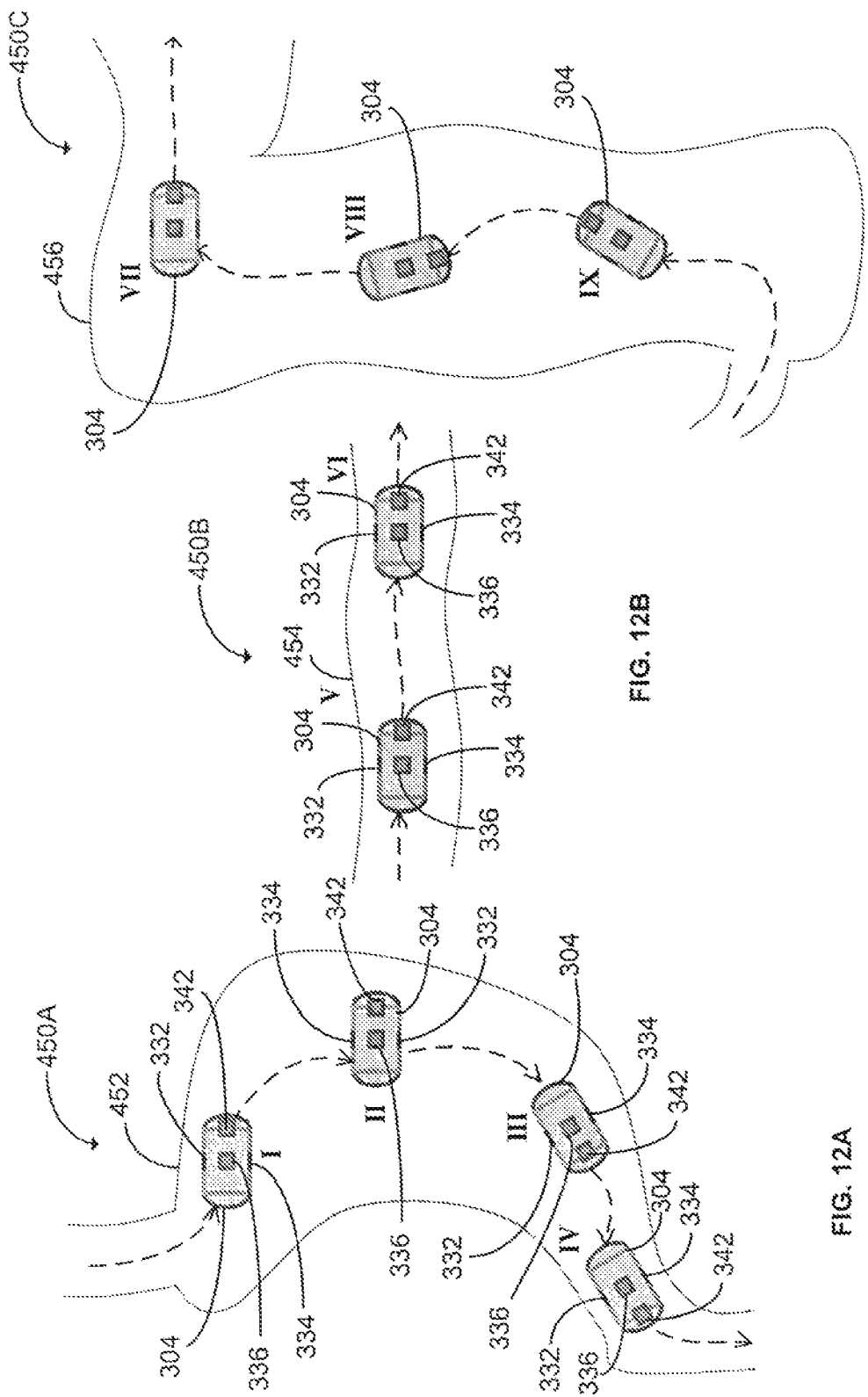

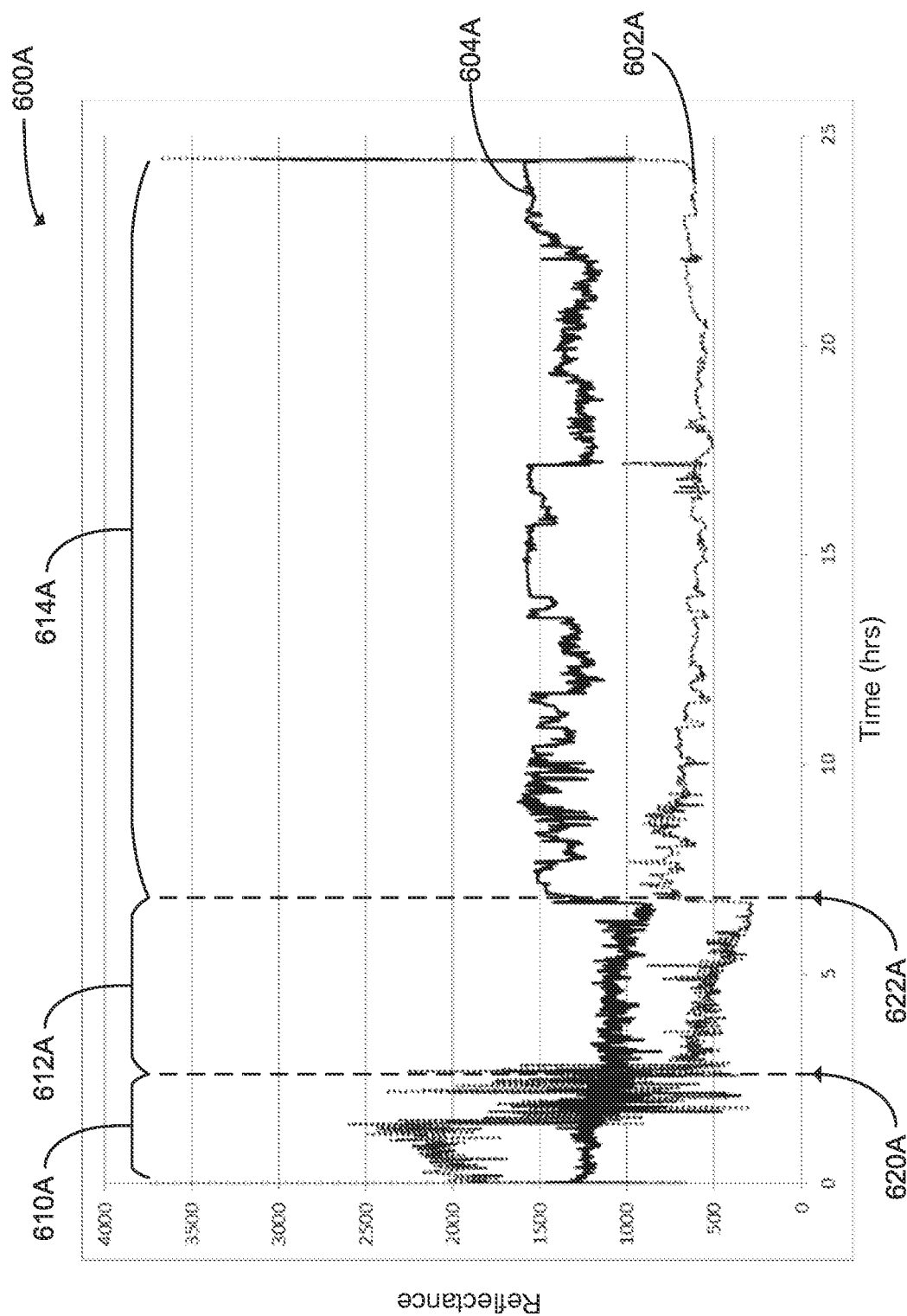

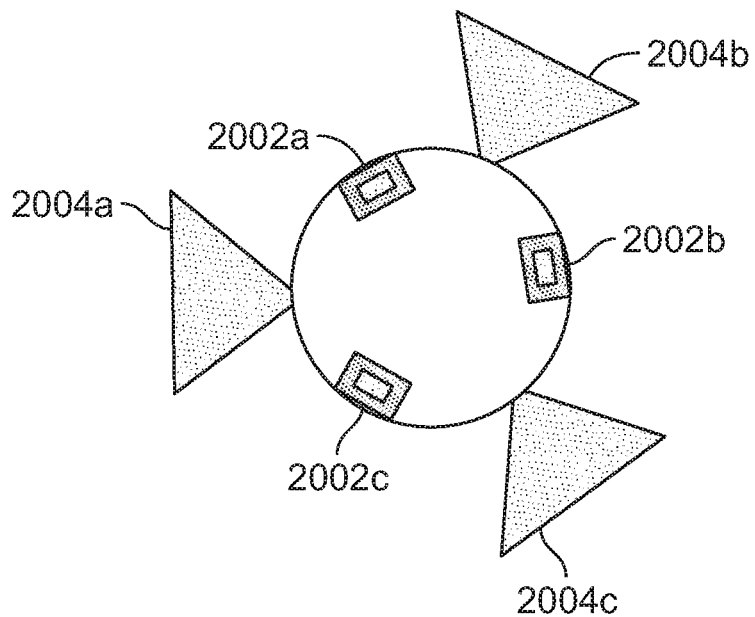
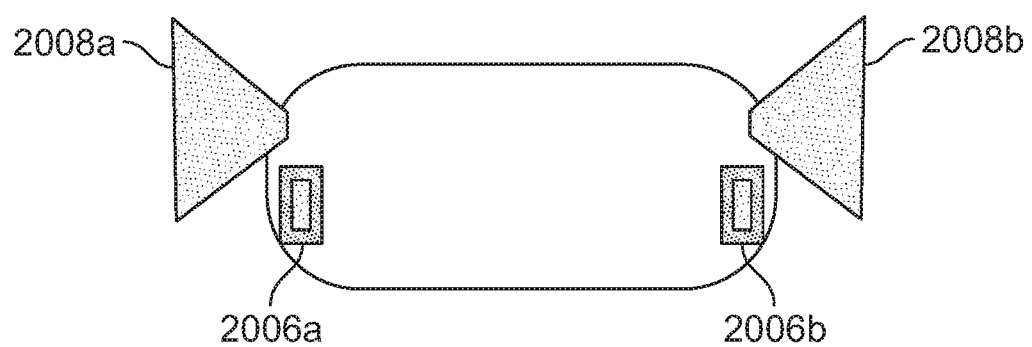
FIG. 20

ELECTROMECHANICAL PILL DEVICE WITH LOCALIZATION CAPABILITIES

CROSS-REFERENCE OF RELATED APPLICATIONS

This application is a United States National Stage under 35 U.S.C. § 371 of International Application No. PCT/US2015/052500 (pending), filed Sep. 25, 2015, which claims priority from U.S. Provisional Application No. 62/055,244. The content of each of the aforementioned patent applications is hereby incorporated by reference in their entirety.

BACKGROUND

The gastrointestinal (GI) tract generally contains a wealth of information regarding an individual's body. For example, contents in the GI tract may provide information regarding the individual's metabolism. An analysis of the contents of the GI tract may also provide information for identifying relationships between the GI content composition (e.g., relationship between bacterial and biochemical contents) and certain diseases or disorders.

Present methods and devices for analyzing the GI tract are limited in certain aspects, such as the accuracy of the data retrieved from the GI tract. Data retrieved from the GI tract can include physical samples and/or measurements. The value of the retrieved data can depend, to an extent, on how accurately the location from which the data is retrieved can be identified. However, in vivo location detection within the GI tract can be difficult. The different segments within the GI tract may, at times, include certain substances (e.g., blood) that can impact in vivo location detection and there may also be differences in the GI tract amongst different individuals.

SUMMARY

In some aspects, an ingestible device for identifying a location within a gastrointestinal (GI) tract of a body is provided herein. The ingestible device includes a housing defined by a first end, a second end substantially opposite from the first end, and a radial wall extending longitudinally from the first end to the second end; a sensing unit inside the housing, the sensing unit including: an axial optical sensing sub-unit located proximal to at least one of the first end and the second end, the axial optical sensing sub-unit being configured to transmit an axial illumination towards an environment external to the housing and to detect an axial reflectance from the environment resulting from the axial illumination; and a radial optical sensing sub-unit located proximal to the radial wall, the radial optical sensing sub-unit being configured to transmit a radial illumination towards the environment external to the housing and to detect a radial reflectance from the environment resulting from the radial illumination, the radial illumination being substantially perpendicular to the axial illumination; wherein a processing module is configured to identify the location of the ingestible device based on at least the detected radial and axial reflectance.

In at least some embodiments, the processing module may be an external processing module and the device may further comprise a communication module configured to transmit one or more radial reflectance values corresponding to the detected radial reflectance and one or more axial reflectance values corresponding to the detected axial reflectance to the external processing module.

In at least some embodiments, the device may comprise the processing module.

In at least some embodiments, the axial optical sensing sub-unit may comprise at least one axial sensor having an axial illuminator configured to transmit the axial illumination and an axial detector configured to detect the axial reflectance.

In at least some embodiments, the radial optical sensing sub-unit may comprise at least one radial sensor having a radial illuminator configured to transmit the radial illumination and a radial detector configured to detect the radial reflectance.

In at least some embodiments, the radial optical sensing sub-unit may comprise three radial sensors, the radial illuminator and the radial detector of a given radial sensor are disposed approximately 60 degrees from each other along a circumference of the radial wall.

In at least some embodiments, the radial optical sensing sub-unit further comprises four radial sensors, each radial sensor being positioned substantially equidistant from each other along a circumference of the radial wall.

In at least some embodiments, the axial optical sensing sub-unit may comprise a first axial sensor located proximal to the first end of the ingestible device, the first axial sensor configured to transmit a first axial illumination towards the environment and to detect a first axial reflectance from the environment resulting from the first axial illumination; and a second axial sensor located proximal to the second end of the ingestible device, the second axial sensor configured to transmit a second axial illumination towards the environment and to detect a second axial reflectance from the environment resulting from the second axial illumination, the second axial illumination being in a substantially opposite direction from the first axial illumination.

In at least some embodiments, the radial optical sensing sub-unit may comprise a first radial sensor located proximal to a first wall portion of the radial wall, the first radial sensor configured to transmit a first radial illumination towards the environment and to detect a first radial reflectance from the environment resulting from the first radial illumination; and a second radial sensor located proximal to a second wall portion of the radial wall, the second radial sensor configured to transmit a second radial illumination towards the environment and to detect a second radial reflectance from the environment resulting from the second radial illumination, the second wall portion being spaced from the first wall portion by at least 60 degrees along a circumference of the radial wall, and the second radial illumination being in a different radial direction from the first radial illumination.

In at least some embodiments, the first wall portion may be spaced from the second wall portion by approximately 180 degrees along the circumference of the radial wall.

In at least some embodiments, the radial optical sensing sub-unit may further comprise a third radial sensor located proximal to a third wall portion of the radial wall, the third radial sensor configured to transmit a third radial illumination towards the environment and to detect a third radial reflectance from the environment resulting from the third radial illumination, the third wall portion being spaced from each of the first wall portion and the second wall portion by approximately 60 degrees along the circumference of the radial wall, and the third radial illumination being in another different radial direction from the first radial illumination and the second radial illumination.

In at least some embodiments, the axial optical sensing sub-unit may comprise an infrared Light-Emitting Diode (LED).

In at least some embodiments, the radial optical sensing sub-unit may comprise a LED emitting light having a wavelength of approximately 571 nm.

In at least some embodiments, the radial optical sensing sub-unit may comprise a RGB LED package.

In at least some embodiments, the housing is capsule-shaped.

In some aspects, a method for identifying a location within a GI tract of a body is provided herein. The method including: using an ingestible device comprising: a housing having a first end, a second end substantially opposite from the first end, and a radial wall extending longitudinally from the first end to the second end; and a sensing unit inside the housing, the sensing unit including: an axial optical sensing sub-unit located proximal to at least one of the first end and the second end, the axial optical sensing sub-unit being configured to transmit an axial illumination towards an environment external to the housing and to detect an axial reflectance from the environment resulting from the axial illumination; and a radial optical sensing sub-unit located proximal to the radial wall, the radial optical sensing sub-unit being configured to transmit a radial illumination towards the environment external to the housing and to detect a radial reflectance from the environment resulting from the radial illumination, the radial illumination being substantially perpendicular to the axial illumination; and operating a processing module to identify the location based on at least the detected radial and axial reflectance.

The ingestible device may further be defined according to any of the teachings herein.

In some aspects, a system for identifying a location within the GI tract of a body is provided herein. The system includes: an ingestible device including: a housing having a first end, a second end substantially opposite from the first end, and a radial wall extending longitudinally from the first end to the second end; and a sensing unit inside the housing, the sensing unit including: an axial optical sensing sub-unit located proximal to at least one of the first end and the second end, the axial optical sensing sub-unit being configured to transmit an axial illumination towards an environment external to the housing and to detect an axial reflectance from the environment resulting from the axial illumination; and a radial optical sensing sub-unit located proximal to the radial wall, the radial optical sensing sub-unit being configured to transmit a radial illumination towards the environment external to the housing and to detect a radial reflectance from the environment resulting from the radial illumination, the radial illumination being substantially perpendicular to the axial illumination; and a processing module configured to identify the location of the ingestible device based on at least the radial and axial reflectance detected during transit within the body.

The ingestible device may further be defined according to any one of the teachings herein.

In some aspects, another method for identifying a location within the GI tract of a body is provided herein. The method including: providing an ingestible device having a sensing unit to collect reflectance data, the sensing unit including: an axial optical sensing sub-unit operable to transmit an axial illumination towards an environment external to the ingestible device and to detect an axial reflectance from the environment resulting from the axial illumination; and a radial optical sensing sub-unit operable to transmit a radial illumination towards the environment external to the ingestible device and to detect a radial reflectance from the environment resulting from the radial illumination, the radial illumination being substantially perpendicular to the axial illumination; operating the sensing unit to collect, at least, a reflectance data series as the ingestible device transits through the body, the reflectance data series comprising an axial reflectance data series and a radial reflectance data series, each of the axial reflectance data series and the radial reflectance data series including one or more reflectance values corresponding to the respective axial reflectance and radial reflectance detected by the sensing unit during at least a portion of the transit; and operating a processing module to identify the location using the reflectance data series, the processing module being in electronic communication with the sensing unit, the processing module being configured to: determine a quality of the environment external to the ingestible device based on the axial reflectance data series and the radial reflectance data series; and indicate the location based on the determined quality of the environment external to the ingestible device.

In at least some embodiments, determining the quality of the environment external to the ingestible device based on each of the axial reflectance data series and the radial reflectance data series may comprise: generating an axial standard deviation for the axial reflectance data series and a radial standard deviation for the radial reflectance data series; determining whether each of the axial standard deviation and the radial standard deviation satisfies a corresponding deviation threshold; and in response to determining the axial standard deviation and the radial standard deviation satisfy the deviation threshold, defining the quality of the environment as homogenous.

In at least some embodiments, the deviation threshold may comprise an axial deviation threshold for the axial reflectance data series and a radial deviation threshold for the radial reflectance data series, the radial deviation threshold having a different value from the axial deviation threshold.

In at least some embodiments, in response to determining that the axial standard deviation and the radial standard deviation satisfy the deviation threshold and prior to defining the quality of the environment as homogenous, the method may further comprise: generating an axial average from a portion of the axial reflectance data series and a radial average from a portion of the radial reflectance data series; determining whether the radial average is less than the axial average; and in response to determining the radial average is less than the axial average, defining the quality of the environment as homogenous.

In at least some embodiments, determining whether the radial average is less than the axial average may comprise determining whether the radial average is less than the axial average by a minimum difference value.

In at least some embodiments, generating the axial average from the portion of the axial reflectance data series and the radial average from the portion of the radial reflectance data series may comprise selecting a number of reflectance values from each of the axial reflectance data series and the radial reflectance data series, the number of reflectance values being selected from a most recent portion of the respective axial reflectance data series and the radial reflectance data series.

In at least some embodiments, the sensing unit may further comprise a temperature sensor for collecting a temperature data series as the ingestible device transits through the body; and prior to associating the quality of the environment as homogenous, the method may further comprise: determining whether a portion of the temperature data series includes a temperature change exceeding a temperature threshold; and in response to determining the portion of the temperature data series does not include the temperature change exceeding the temperature threshold, associating the quality of the environment as homogenous.

In at least some embodiments, the processing module may be operated to indicate the location is the small intestine in response to determining the quality of the environment external to the ingestible device is homogenous.

In some aspects, another ingestible device for identifying a location within the GI tract of a body is provided herein. The ingestible device may include a sensing unit configured to collect reflectance data, the sensing unit including: an axial optical sensing sub-unit operable to transmit an axial illumination towards an environment external to the ingestible device and to detect an axial reflectance from the environment resulting from the axial illumination; and a radial optical sensing sub-unit operable to transmit a radial illumination towards the environment external to the ingestible device and to detect a radial reflectance from the environment resulting from the radial illumination, the radial illumination being substantially perpendicular to the axial illumination; wherein a processing module is configured to: operate the sensing unit to collect, at least, a reflectance data series as the ingestible device transits through the body, the reflectance data series comprising an axial reflectance data series and a radial reflectance data series, each of the axial reflectance data series and the radial reflectance data series including one or more reflectance values corresponding to the respective axial reflectance and radial reflectance detected by the sensing unit during at least a portion of the transit; determine a quality of the environment external to the ingestible device based on the axial reflectance data series and the radial reflectance data series; and indicate the location based on the determined quality of the environment external to the ingestible device.

The processing module may be configured to perform at least one of the methods in accordance with the teachings herein.

In at least some embodiments, the processing module may be an external processing module and the device may further comprise a communication module in electronic communication with the external processing module.

In at least some embodiments, the processing module may be located within the device.

In some aspects, another method for identifying a location within the GI tract of a body is provided herein. The method includes: operating an axial optical sensing sub-unit to transmit an axial illumination towards an environment within the GI tract and to detect an axial reflectance from the environment resulting from the axial illumination; operating a radial optical sensing sub-unit to transmit a radial illumination towards the environment within the GI tract and to detect a radial reflectance from the environment resulting from the radial illumination, the radial illumination being substantially perpendicular to the axial illumination; and operating a processing module to identify the location using the detected axial reflectance and the detected radial reflectance, the processing module being configured to: determine a quality of the environment within the GI tract based on the detected axial reflectance and the detected radial reflectance; and indicate the location based on the determined quality of the environment within the GI tract.

In at least one embodiment, the method may further comprise collecting, at least, a reflectance data series over a period of time, the reflectance data series comprising an axial reflectance data series and a radial reflectance data series, each of the axial reflectance data series and the radial reflectance data series including one or more reflectance values corresponding to the respective axial reflectance and radial reflectance detected by the respective axial optical sensing sub-unit and the radial optical sensing sub-unit during the period of time.

In at least one embodiment, determining the quality of the environment within the GI tract based on the detected axial reflectance and the detected radial reflectance may comprise generating an axial standard deviation for the axial reflectance data series and a radial standard deviation for the radial reflectance data series; determining whether each of the axial standard deviation and the radial standard deviation satisfies a corresponding deviation threshold; and in response to determining the axial standard deviation and the radial standard deviation satisfy the deviation threshold, defining the quality of the environment as homogenous.

In at least one embodiment, the deviation threshold may comprise an axial deviation threshold for the axial reflectance data series and a radial deviation threshold for the radial reflectance data series, the radial deviation threshold having a different value from the axial deviation threshold.

In at least one embodiment, the method may further comprise, in response to determining that the axial standard deviation and the radial standard deviation satisfy the deviation threshold and prior to defining the quality of the environment as homogenous: generating an axial average from a portion of the axial reflectance data series and a radial average from a portion of the radial reflectance data series; determining whether the radial average is less than the axial average; and in response to determining the radial average is less than the axial average, defining the quality of the environment as homogenous.

In at least one embodiment, determining whether the radial average is less than the axial average may comprise determining whether the radial average is less than the axial average by a minimum difference value.

In at least one embodiment, generating the axial average from the portion of the axial reflectance data series and the radial average from the portion of the radial reflectance data series may comprise selecting a number of reflectance values from each of the axial reflectance data series and the radial reflectance data series, the number of reflectance values being selected from a most recent portion of the respective axial reflectance data series and the radial reflectance data series.

In at least one embodiment, the method may further comprise operating a temperature sensor to collect a temperature data series; and prior to associating the quality of the environment as homogenous, the method further comprises determining whether a portion of the temperature data series includes a temperature change exceeding a temperature threshold; and in response to determining the portion of the temperature data series does not include the temperature change exceeding the temperature threshold, associating the quality of the environment as homogenous.

In at least one embodiment, the processing module may be operated to indicate the location is the small intestine in response to determining the quality of the environment within the GI tract is homogenous.

In some aspects, a computer readable medium having a plurality of instructions executable on a processing module of a device for adapting the device to implement any of the methods of identifying a location within the GI track of a body as described is provided herein.

In some aspects, another method for determining a location of an ingestible device within a gastrointestinal tract of a body is provided herein. The method includes: transmitting a first illumination at a first wavelength towards an environment external to a housing of the ingestible device; detecting a first reflectance from the environment resulting from the first illumination, and storing a first reflectance value in a first data set, wherein the first reflectance value is indicative of an amount of light in the first reflectance; transmitting a second illumination at a second wavelength towards an environment external to the housing of the ingestible device, wherein the second wavelength is different than the first wavelength; detecting a second reflectance from the environment resulting from the second illumination, and storing a second reflectance value in a second data set, wherein the second reflectance value is indicative of an amount of light in the second reflectance; identifying a state of the ingestible device, wherein the state is a known or estimated location of the ingestible device; and determining a change in the location of the ingestible device within the gastrointestinal tract of the body by detecting whether a state transition has occurred, the state transition detected by comparing the first data set to the second data set.

In some embodiments, comparing the first data set to the second data set comprises taking a difference between the first reflectance value stored in the first data set, and the second reflectance value stored in the second data set.

In some embodiments, comparing the first data set to the second data set comprises integrating at least one of (i) the difference between reflectance values stored in the first data set and reflectance values stored in the second data set, or (ii) the difference between a moving average of the first data set and a moving average of the second data set.

In some embodiments, comparing the first data set and the second data set comprises taking a first mean from reflectance values stored in the first data set, taking a second mean from reflectance values stored in the second data set, and taking a difference between the first mean and the second mean.

In some embodiments, comparing the first data set and the second data set comprises incrementing a counter when the mean of the first data set less a multiple of the standard deviation of the first data set is greater than a mean of the second data set plus a multiple of the standard deviation of the second data set.

In some embodiments, the first wavelength is in at least one of a red and an infrared spectrum, and the second wavelength is in at least one of a blue and a green spectrum.

In some embodiments, the identified state is a stomach, and wherein when the comparing indicates that the first data set and the second data set have diverged in a statistically significant manner, a state transition has occurred, wherein the state transition is a pyloric transition.

In some embodiments, the identified state is a duodenum, and wherein when the comparing indicates that a difference between the first data set and the second data set is constant in a statistically significant manner, a state transition has occurred, wherein the state transition is a treitz transition.

In some embodiments, the first wavelength is in an infrared spectrum, and the second wavelength is in at least one of a green and a blue spectrum.

In some embodiments, the identified state is a jejunum, and wherein when the comparing indicates that the first data set and the second data set have converged in a statistically significant manner, a state transition has occurred, wherein the state transition is an ileocaecal transition.

In some embodiments, the first wavelength is in a red spectrum, and the second wavelength is in at least one of a green and a blue spectrum.

In some embodiments, the identified state is a caecum, and wherein when the comparing indicates that the first data set and the second data set have converged in a statistically significant matter, a state transition has occurred, wherein the state transition is a caecal transition.

In some embodiments, the method further comprises measuring a temperature change of the environment external to the housing of the ingestible device.

In some embodiments, the identified state is external to the body, and wherein the measured temperature change is above a threshold, a state transition has occurred, wherein the state transition is entering the stomach.

In some embodiments, the identified state is a large intestine, and wherein the measured temperature change is above a threshold, a state transition has occurred, wherein the state transition is exiting the body.

In some embodiments, the method further comprises: deactivating a function of the ingestible device for a predetermined period of time after detecting whether a state transition has occurred; reactivating the function of the ingestible device after the predetermined period of time; transmitting a third illumination at the first wavelength towards an environment external to a housing of the ingestible device; detecting a third reflectance from the environment resulting from the third illumination, and storing a third reflectance value in the first data set, wherein the third reflectance value is indicative of an amount of light detected by the ingestible device from the third reflectance; transmitting a fourth illumination at the second wavelength towards an environment external to the housing of the ingestible device; detecting a fourth reflectance from the environment resulting from the fourth illumination, and storing a fourth reflectance value in the second data set, wherein the fourth reflectance value is indicative of an amount of light detected by the ingestible device from the fourth reflectance; identifying the state of the ingestible device; and determining a change in the location of the ingestible device within the gastrointestinal tract of the body by detecting whether the state transition has occurred, the state transition detected by comparing the first data set to the second data set.

In some embodiments, the state of the ingestible device is selected from one of: external to the body; stomach; pylorus; small intestine; duodenum; jejunum; ileum; large intestine; caecum; and colon.

In some embodiments, the state transition is selected from one of: entering the body; entering the stomach; pyloric transition; treitz transition; ileocecal transition; caecal transition; and exiting the body.

In some aspects, another ingestible device is provided herein a housing defined by a first end, a second end opposite from the first end, and a radial wall extending longitudinally from the first end to the second end; a sensing unit inside the housing, the sensing unit comprising: a first optical sensing sub-unit configured to transmit a first illumination towards an environment external to the housing at a first wavelength, and to detect a first reflectance from the environment resulting from the first illumination; a second optical sensing sub-unit configured to transmit a second illumination towards an environment external to the housing at a second wavelength, wherein the second wavelength is different than the first wavelength, and to detect a second reflectance from the environment resulting from the second illumination; and a processing module located within the ingestible device configured to: store a first reflectance value in a first data set, wherein the first reflectance value is indicative of an amount of light detected by the device from the first reflectance; store a second reflectance value in a second data set, wherein the second reflectance value is indicative of an amount of light detected by the device from the second reflectance; identify a state of the device, wherein the state is a known or estimated location of the ingestible device; and determine a change in the location of the ingestible device within the gastrointestinal tract of the body by detecting whether a state transition has occurred, the state transition detected by comparing the first data set to the second data set.

In some embodiments, the ingestible device may further be defined according to any one of the teachings herein.

In some embodiments, another system for determining a location of an ingestible device within a gastrointestinal tract of a body is provided herein. The system comprises means for transmitting a first illumination at a first wavelength towards an environment external to a housing of the ingestible device; means for detecting a first reflectance from the environment resulting from the first illumination, and means for storing a first reflectance value in a first data set, wherein the first reflectance value is indicative of an amount of light in the first reflectance; means for transmitting a second illumination at a second wavelength towards an environment external to the housing of the ingestible device, wherein the second wavelength is different than the first wavelength; means for detecting a second reflectance from the environment resulting from the second illumination, and means for storing a second reflectance value in a second data set, wherein the second reflectance value is indicative of an amount of light in the second reflectance; means for identifying a state of the ingestible device, wherein the state is a known or estimated location of the ingestible device; and means for determining a change in the location of the ingestible device within the gastrointestinal tract of the body by detecting whether a state transition has occurred, the state transition detected by comparing the first data set to the second data set.

In some embodiments, the system may be further defined according to any one of the teaching herein.

In some aspects, another method for sampling the gastrointestinal tract with an ingestible device is provided herein. The method includes transmitting a first illumination at a first wavelength towards an environment external to a housing of the ingestible device; detecting a first reflectance from the environment resulting from the first illumination; transmitting a second illumination at a second wavelength towards an environment external to the housing of the ingestible device; detecting a second reflectance from the environment resulting from the second illumination; determining a location of the ingestible device within the gastrointestinal tract of the body based on the first reflectance and the second reflectance; and sampling the gastrointestinal tract when the determined location matches a predetermined location.

In some embodiments, sampling the gastrointestinal tract comprises moving a portion of the housing of the ingestible device from an orientation that does not allow a sample from the gastrointestinal tract to enter a sample chamber, to an orientation that allows the sample to enter the sample chamber.

In some embodiments, the method further comprises determining an amount of time after the sampling the gastrointestinal tract; and resampling the gastrointestinal tract when the determined amount of time is greater than a threshold value.

In some embodiments, the method further comprises determining a second location of the ingestible device within the gastrointestinal tract based on a detected third reflectance; and resampling the gastrointestinal tract when the determined location matches a second predetermined location.

In some embodiments, resampling the gastrointestinal tract comprises moving a portion of the housing of the ingestible device from an orientation that does not allow a second sample from the gastrointestinal tract to enter a second sample chamber, to an orientation that allows the second sample to enter the second sample chamber.

In some aspects, another ingestible device is provided herein. The ingestible device includes a housing defined by a first end, a second end opposite from the first end, and a radial wall extending longitudinally from the first end to the second end; a sampling chamber located proximal to the housing; a sensing unit inside the housing, the sensing unit comprising: a first optical sensing sub-unit configured to transmit a first illumination towards an environment external to the housing at a first wavelength, and to detect a first reflectance from the environment resulting from the first illumination; a second optical sensing sub-unit configured to transmit a second illumination towards an environment external to the housing at a second wavelength, and to detect a second reflectance from the environment resulting from the second illumination; a processing module located within the ingestible device configured to: determine a location of the ingestible device within the gastrointestinal tract of the body based on the first reflectance and the second reflectance; and sampling the gastrointestinal tract when the identified location matches a predetermined location by actuating at least one of a portion of the housing and the sampling chamber.

In some embodiments, the ingestible device may be further defined according to any one of the teaching herein.

In some aspects, another system for sampling the gastrointestinal tract with an ingestible device is provided herein. The system includes means for transmitting a first illumination at a first wavelength towards an environment external to a housing of the ingestible device; means for detecting a first reflectance from the environment resulting from the first illumination; means for transmitting a second illumination at a second wavelength towards an environment external to the housing of the ingestible device; means for detecting a second reflectance from the environment resulting from the second illumination; means for determining a location of the ingestible device within the gastrointestinal tract of the body based on the first reflectance and the second reflectance; and means for sampling the gastrointestinal tract when the determined location matches a predetermined location.

In some embodiments, the system may be further defined according to any one of the teachings herein.

In some aspects, another method for releasing a substance into the gastrointestinal tract with an ingestible device is provided herein. The method includes transmitting a first illumination at a first wavelength towards an environment external to a housing of the ingestible device; detecting a first reflectance from the environment resulting from the first illumination; transmitting a second illumination at a second wavelength towards an environment external to the housing of the ingestible device; detecting a second reflectance from the environment resulting from the second illumination; determining a location of the ingestible device within the gastrointestinal tract of the body based on the first reflectance and the second reflectance; and releasing the substance into the gastrointestinal tract when the determined location matches a predetermined location.

BRIEF DESCRIPTION OF THE DRAWINGS

The above and other objects and advantages will become apparent with consideration of the following detailed description, taken in conjunction with the accompanying drawings, in which like reference characters refer to like parts throughout, and in which:

FIG. 1A is a view of an example embodiment of an ingestible device.

FIG. 1B is an exploded view of the ingestible device of FIG. 1A.

FIG. 2D is a top view of a circuit design of a flexible PCB that may be used in the ingestible device of FIG. 1A.

FIG. 2E is a bottom view of the circuit design of FIG. 2D.

FIGS. 3A and 3B are diagrams of an example sensor configuration for an ingestible device.

FIGS. 4A and 4B are diagrams of another example sensor configuration for an ingestible device.

FIGS. 5A and 5B are diagrams of a further example sensor configuration for an ingestible device.

FIGS. 6A and 6B are diagrams of yet another example sensor configuration for an ingestible device.

FIGS. 7A to 7C illustrate diagrams of the ingestible device of FIG. 3A in an example operation.

FIGS. 10A to 10C are diagrams of the ingestible device of FIG. 3A during an example transit through an individual's gastrointestinal (GI) tract.

FIGS. 11A to 11C are diagrams of the ingestible device of FIG. 4A during an example transit through an individual's GI tract.

FIGS. 12A to 12C are diagrams of the ingestible device of FIG. 5A during an example transit through an individual's GI tract.

FIGS. 13A to 13C are plots illustrating data collected during example operations of the ingestible device of FIG. 3A.

FIG. 20 is a simplified top view and side view of the device in FIG. 19.

DESCRIPTION

Figure 2A:
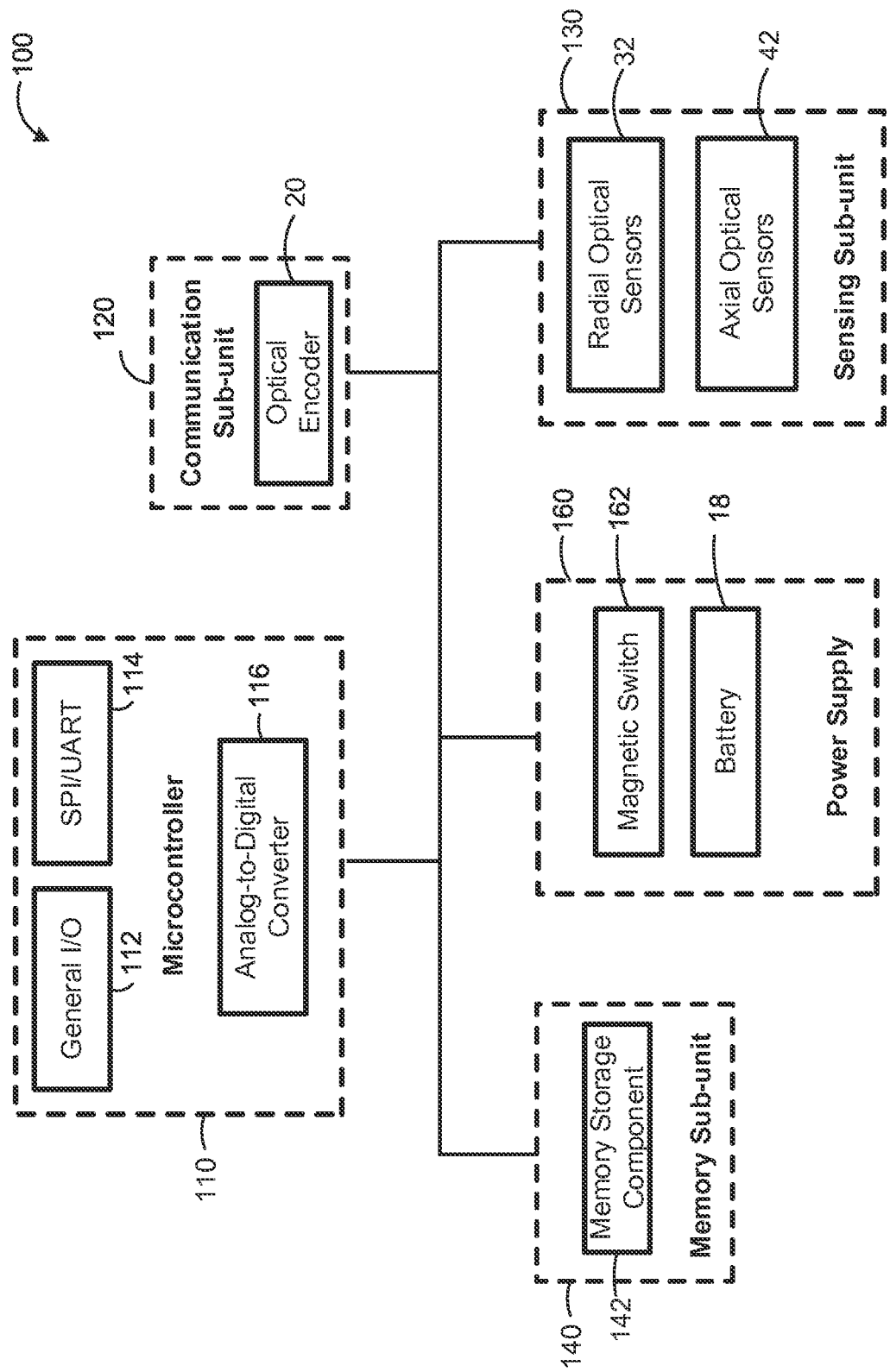
FIG. 2A is an example block diagram of the electrical components that may be used for the ingestible device of FIG. 1A.

Various systems, devices, and methods are described herein to provide an example of at least one embodiment for the claimed subject matter. No embodiment limits any claimed subject matter and any claimed subject matter may cover systems, devices, and methods that differ from those described herein. It is possible that the claimed subject matter are not limited to systems, devices, and methods having all of the features of any one systems, devices, and methods described herein or to features common to multiple or all of the systems, devices, and methods described herein. It may be possible that a system, device, or method described herein is not an embodiment of any claimed subject matter. Any subject matter disclosed in systems, devices, and methods described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that, for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used herein, the term "coupled" indicates that two elements can be directly coupled to one another or coupled to one another through one or more intermediate elements.

As used herein, the term "body" refers to the body of a patient, a subject or an individual who receives the ingestible device. The patient or subject is generally a human or other animal.

The various embodiments described herein generally relate to an ingestible device for identifying one or more locations within the gastrointestinal (GI) tract and, in some embodiments, for collecting data and/or releasing substances including medicaments and therapeutics at the identified location. As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts.

As used herein, the term "reflectance" refers to a value derived from light emitted by the device, reflected back to the device, and received by a detector in or on the device. For example, in some embodiments this refers to light emitted by the device, wherein a portion of the light is reflected by a surface external to the device, and the light is received by a detector located in or on the device.

As used herein, the term "illumination" refers to any electromagnetic emission. In some embodiments, an illumination may be within the range of Infrared Light (IR), the visible spectrum and ultraviolet light (UV), and an illumination may have a majority of its power centered at a particular wavelength in the range of 100 nm to 1000 nm. In some embodiments, it may be advantageous to use an illumination with a majority of its power limited to one of the infrared (750 nm-1000 nm), red (620 nm-750 nm), green (495 nm-570 nm), blue (450 nm-495 nm), or ultraviolet (100 nm-400 nm) spectrums. In some embodiments a plurality of illuminations with different wavelengths may be used.

Referring now to FIG. 1A, shown therein is a view of an example embodiment of an ingestible device 10 in which a portion of the housing 12 of the ingestible device 10 has been removed. The ingestible device 10 may be used for autonomously identifying a location within the body, such as a portion of the gastrointestinal tract. In some embodiments, the ingestible device 10 can discern whether it is located in the stomach, the small intestine, or the large intestine. In some embodiments the ingestible device may also be able to discern what portion of the small intestine it is located in, such as the duodenum, the jejunum or the ileum. The ingestible device 10 may generally be in the shape of a capsule, like a conventional pill. Accordingly, the shape of the ingestible device 10 provides for easy ingestion and is familiar to healthcare practitioners and patients.

Unlike a conventional pill, the ingestible device 10 is designed to withstand the chemical and mechanical environment of the GI tract (e.g., effects of muscle contractile forces and concentrated hydrochloric acid in the stomach). However, unlike other devices that are intended to stay inside a patient's body (e.g., medical implants), the ingestible device 10 may be designed to travel temporarily within the body. Accordingly, the regulatory rules governing the materials and manufacture of the ingestible device 10 may be less strict than those for the devices that are intended to stay inside the body. Nevertheless, because the ingestible device 10 enters the body, the materials used to manufacture the ingestible device 10 are generally selected to at least comply with the standards for biocompatibility (e.g., ISO 10993). Furthermore, components inside the ingestible device 10 are free of any restricted and/or toxic metals and are lead-free pursuant to the Directive 2002/95/EC of the European Parliament, which is also known as the Restriction of Hazardous Substances (RoHS).

There is a broad range of materials that may be used for manufacturing the ingestible device 10. Different materials may be used for each of the different components of the ingestible device 10. Examples of these materials include, but are not limited to, thermoplastics, fluoropolymers, elastomers, stainless steel and glass complying with ISO 10993 and USP Class VI specifications for biocompatibility; and any other suitable materials and combinations thereof. In certain embodiments, these materials may further include liquid silicone rubber material with a hardness level of 10 to 90 as determined using a durometer (e.g., MED-4942™ manufactured by NuSil™), a soft biocompatible polymer material such as, but not limited to, polyvinyl chloride (PVC), polyethersulfone (PES), polyethylene (PE), polyurethane (PU) or polytetrafluoroethylene (PTFE), and a rigid polymer material coated with a biocompatible material that is soft or pliable (e.g., a poly(methyl methacrylate) (PMMA) material coated with silicone polymer). Use of different materials for different components may enable functionalization of certain surfaces for interaction with proteins, antibodies, and other biomarkers. For example, Teflon® may be used as a material in the ingestible device 10 for movable components in order to reduce friction between these components. Other example materials may include other materials commonly used in microfabrication, such as polydimethylsiloxane (PDMS), borosilicate glass, and/or silicon. Although we may refer to specific materials being used to construct the device for illustrative purposes, the materials recited are not intended to be limiting, and one skilled in the art may easily adapt the device to use any number of different materials without affecting the overall operation or functionality of the device.

In some embodiments, the housing 12 of the ingestible device 10 may be manufactured from a type of plastic, such as a photosensitive acrylic polymer material or an inert polycarbonate material. The housing 12 may also be formed using material that can be sterilized by chemicals.

The housing 12 may be formed by coupling two enclosure portions together. For example, the two enclosure portions can be mated and fused together with an adhesive material, such as a cyanoacrylate variant. The housing 12, in effect, protects the interior of the ingestible device 10 from its external environment and also protects the external environment (e.g., the gastrointestinal tract) from components inside the ingestible device 10.

Furthermore, the ingestible device 10 may include one or more additional layers of protection. The additional protection may protect a patient or individual against adverse effects arising from any structural problems associated with the housing 12 (e.g., the two enclosure portions falling apart or a fracture developing in the housing 12). For example, a power supply inside the ingestible device 10 may be coated with an inert and pliable material (e.g., a thin layer of silicone polymer) so that only electrical contacts on the power supply are exposed. This additional protection to the power supply may prevent chemicals inside the ingestible device 10 from seeping into the patient's body.

In some embodiments, a surface of the ingestible device 10 and surfaces of the different components in the ingestible device 10 may receive different treatments that vary according to an intended use of the ingestible device 10. For example, the surface of the ingestible device 10 may receive plasma activation for increasing hydrophilic behavior. In another example, for minimizing cross-contamination in the collected samples and/or substances for release, certain storage components that may come into contact with these samples and/or substances may receive hydrophilic treatment while certain other components may receive hydrophobic treatments.

The components of the ingestible device 10 may be too small and complex for fabrication with conventional tools (e.g., lathe, manual milling machines, drill-press, and the like) but too large for efficient construction using microfabrication techniques. Fabrication techniques that fall between the conventional and microfabrication techniques may be used which include, but are not limited to, 3D printing (e.g., Multi jet Modeling (MJM) of 3D mechanical computer-aided design (CAD). Software packages by SolidWorks™ and/or Alibr™ are examples of CAD software that may be used to design certain components of the ingestible device 10, although any suitable CAD software may be used.

In some embodiments, components of the ingestible device 10 may be fabricated using different conventional manufacturing techniques such as injection molding, computer numerical control (CNC) machining and by using multi-axial lathes. For example, the housing 12 of the ingestible device 10 may be fabricated from CNC machined polycarbonate material and the storage component may be fabricated by applying a biocompatible material, such as silicone polymer, to a 3D-printed mold or cast.

Silicone polymer can provide certain advantages to the fabrication process of the ingestible device 10. For instance, components in the ingestible device 10 that are formed using the silicone polymer material can be fabricated using conventional methods, such as molding techniques. Silicone polymer material is also a pliable material. Therefore, components of the ingestible device 10 that are formed from silicone polymer material can accommodate a range of design deviations during the manufacturing stage and can also be adapted for compression fitting.

Referring still to FIG. 1A, the ingestible device 10 is illustrated in accordance with an example embodiment. The ingestible device 10 includes the housing 12 for providing an enclosure for various electronic and mechanical components. The housing 12 includes a first end portion 16a, a second end portion 16b, and a radial wall 14 extending from the first end portion 16a to the second end portion 16b.

The radial wall 14 can be formed from one or more components. In the example of FIG. 1A, the radial wall includes a first wall portion 14a, a second wall portion 14b and a connecting wall portion 14c for connecting the first wall portion 14a with the second wall portion 14b. Other configurations of the radial wall 14 may be used depending on the application of the ingestible device 10.

Referring now to FIG. 1B, shown therein is an exploded view of the components of the ingestible device 10 in one example embodiment. As shown in FIGS. 1A and 1B, enclosed within the first wall portion 14a are a printed circuit board (PCB) 30, a battery 18, a sensing sub-unit 32, 42, and a communication sub-unit 120. The various components within the ingestible device 10 are described with reference to FIGS. 2A to 2E.

FIG. 2A is a block diagram 100 of an example embodiment of electrical components that may be used for the ingestible device 10. As shown in the block diagram 100, the ingestible device 10 may include a microcontroller 110, a communication sub-unit 120, a sensing sub-unit 130, a power supply 160, and a memory sub-unit 140. At least some of the electronic components can be embedded on the PCB 30.

In some embodiments, the microcontroller 110 includes programming, control and memory circuits for holding and executing firmware or software, and coordinating all functions of the ingestible device 10 and the other peripherals embedded on the PCB 30. For example, the microcontroller 110 may be implemented using a 32-bit microcontroller, such as the STM32 family of microcontrollers from STMicroelectronics™, although any suitable microcontroller may be used.

The microcontroller 110 provided in FIG. 2A may include a general input/output (I/O) interface 112, an SPI or a Universal Asynchronous Receiver/Transmitter (UART) interface 114, and an Analog-to-Digital Converter (A/D Converter) 116. The microcontroller 110 may consider the A/D Converter 116 to be a peripheral device.

The general I/O interface 112 includes a fixed number of general input/output pins (GPIOs). These GPIOs may be grouped into groups of two or three pins for implementing a variety of communication protocols, such as for example Single-Wire Interface (SWI), a two-wire interface (e.g., an Inter-Integrated Circuit or I$^2$C) and/or a serial peripheral interface (SPI). The groups of GPIOs that are delegated to these communication protocols may serve as a bus for connecting the microcontroller 110 with one or more peripheral devices.

Using any of the above listed communication protocols, or any other suitable communication protocol, the microcontroller 110 may send a series of requests to addresses associated with specific groups of GPIOs for detecting which peripheral devices, if any, are present on the bus. If any of the peripheral devices are present on the bus, the peripheral device that is present returns an acknowledgement signal to the microcontroller 110 within a designated time frame. If no response is received within this designated time frame, the peripheral device is considered absent.

The A/D Converter 116 can be coupled with any of the sensors in the sensing sub-unit 130. In some embodiments, the ingestible device 10 can communicate by receiving and/or transmitting infrared light, in which case an infrared (IR) sensitive phototransistor and a resistor coupled to the A/D converter 116 are included in the communication sub-unit 120. Additionally, in some embodiments ingestible device 10 may include an infrared (IR) light emitting diode (LED) coupled to the microcontroller 110 to communicate signals outside of the device.

In some embodiments, the communication sub-unit 120 can receive operating instructions from an external device, such as a base station (e.g., an infrared transmitter and/or receiver on a dock). The base station may be used for initially programming the ingestible device 10 with operating instructions and/or communicating with the ingestible device 10 during operation in real-time or after the ingestible device 10 is retrieved from the body. In some embodiments, the communication sub-unit 120 doesn't receive any operating instructions from an external device, and instead the ingestible device 10 operates autonomously in vivo.

In some embodiments, the communication sub-unit 120 can include an optical encoder 20, such as an infrared emitter and receiver. The IR emitter and receiver can be configured to operate using modulated infrared light, i.e. light within a wavelength range of step 850 nm to 930 nm. Furthermore, the IR receiver may be included in the ingestible device 10 for receiving programming instructions from the IR transmitter at the base station and the IR transmitter may be included in the ingestible device 10 for transmitting data to the IR receiver at the base station. Bidirectional IR communication between the ingestible device 10 and the base station can therefore be provided. It will be understood that other types of optical encoders or communication sub-units can be used in some embodiments; for example, some communication sub-units may utilize Bluetooth, radio frequency (RF) communications, near field communications, and the like, rather than (or in addition to) optical signals.

The sensing sub-unit 130 can include various sensors to obtain in vivo information while the ingestible device 10 is in transit inside the body. Various sensors, such as radial sensors 32 and axial sensors 42, can be provided at different locations of the ingestible device 10 to help identify where the ingestible device 10 may be within the body. In some embodiments, the data provided by the sensors 32, 42 can be used for triggering an operation of the ingestible device 10. For example, in some embodiments the ingestible device 10 may be adapted to include a sampling chamber capable of taking samples from the gastrointestinal tract from the area surrounding the device, and data provided by sensors 32, 42 may trigger the device to obtain a sample. Each sensor 32, 42 can include an illuminator, 32$i$ and 42$i$, and a detector, 32$d$ and 42$d$. The sensors 32, 42 are described further with reference to FIGS. 3A to 8C. As another example, in some embodiments the ingestible device 10 may be adapted to deliver a substance, including medicaments and therapeutics, and data provided by the sensors 32, 34 may trigger the device to deliver the substance.

The memory sub-unit 140 can be provided with a memory storage component 142, such as a flash storage, EEPROM, and the like. The memory sub-unit 140 can be used to store the instructions received from the base station and to store various other operational data, such as transit data and sensor data collected by the sensing sub-unit 130. In some embodiments, the microcontroller 110 can operate to execute the instructions stored at the memory sub-unit 140, which may involve operating other components of the ingestible device 10, such as the sensing sub-unit 130, the communication sub-unit 120 and the power supply 160.

In some embodiments, the power supply 160 can include one or more batteries 18 formed from different chemical compositions, such as lithium polymer, lithium carbon, silver oxide, alkaline, and the like. This can be helpful in accommodating the different power requirements of the various components in the ingestible device 10. In some embodiments, the power supply 160 may include a silver oxide battery cell for supplying power to the various components in the ingestible device 10. The battery cells that supply power to the power supply 160 may operate at 1.55V. For example, a silver oxide coin cell type battery, such as those manufactured by Renata™, may be used since the silver oxide coin cell battery has discharge characteristics that suit the operation of the ingestible device 10. In some embodiments, other types of battery cells may be used.

In some embodiments, it is possible for the power supply 160 to include one or more battery cells. For example, multiple coin cells may be used to provide higher voltage for the operation of the ingestible device. It may also be possible for the power supply 160 to include one or more different types of battery cells.

Also, the power supply 160 may be split into one or more cell groups to prevent a temporary interruption or change at the power supply 160 from affecting the overall operation of the ingestible device 10. For example, an example power supply 160 can include three cells and each cell is operable to provide 1.55 volts. In one example embodiment, the three cells can be provided as one cell group operable to provide 4.65 volts as the full voltage. A voltage regulator may control the voltage that is provided by the cell group. The voltage regulator may operate to provide a regulated voltage, such as 3.3 volts, to the microcontroller 110, while operating to provide the full voltage to the sensing sub-unit 130. In another example embodiment, the three cells can be provided as two different cell groups, with a first cell group including two cells and a second cell group including one cell. The first cell group, therefore, can provide 3.1 volts while the second cell group can be provide 1.55 volts. The first cell group may be operable to provide 3.1 volts to the microcontroller 110 to prevent voltage variations. The first cell group and the second cell group can then be combined to provide 4.65 volts to the sensing sub-unit 130.

The power supply 160 may, in some embodiments, include a magnetic switch 162 for operating as an 'ON'/ 'OFF' mechanism for the ingestible device 10. When exposed to a strong magnetic field, the magnetic switch 162 can be maintained in an 'OFF' position in which the ingestible device 10 is not activated. The strong magnetic field can effectively stop current flow in the ingestible device 10, causing an open circuit to occur. For example, this may prevent the ingestible device 10 from consuming energy and discharging the battery 18 before being administered to a patient. However, when the magnetic switch 162 is no longer exposed to a strong magnetic field, the magnetic switch 162 may switch to an 'ON' position to activate the ingestible device 10. Current may then flow through the electrical pathways in the ingestible device 10 (e.g., pathways on the PCB 30).

In some embodiments, an MK24 reed sensor from MEDER™ Electronics may be used as the magnetic switch 162, although any suitable magnetic switch may be used. For example, in some embodiments, the magnetic switch 162 may be a magnetically actuated, normally closed, Single-Pole Single Throw (SPST-NC) switch. In some embodiments, a micro-electromechanical system (MEMS) magnetic switch, such as one manufactured by MEMSCAP™, may be used as the magnetic switch 162. In some embodiments, the magnetic switch 162 may be a Hall effect sensor.

In some embodiments, the power supply 160 may be removed from the ingestible device 10 to be recharged by recharging circuitry that is external to the ingestible device 10. In some embodiments, the power supply 160 may be recharged while in the ingestible device 10 when recharging circuitry is included on the PCB 30; for example, by providing circuitry that allows the ingestible device 10 to be inductively coupled to a base station and charged wirelessly.

Figure 2B:
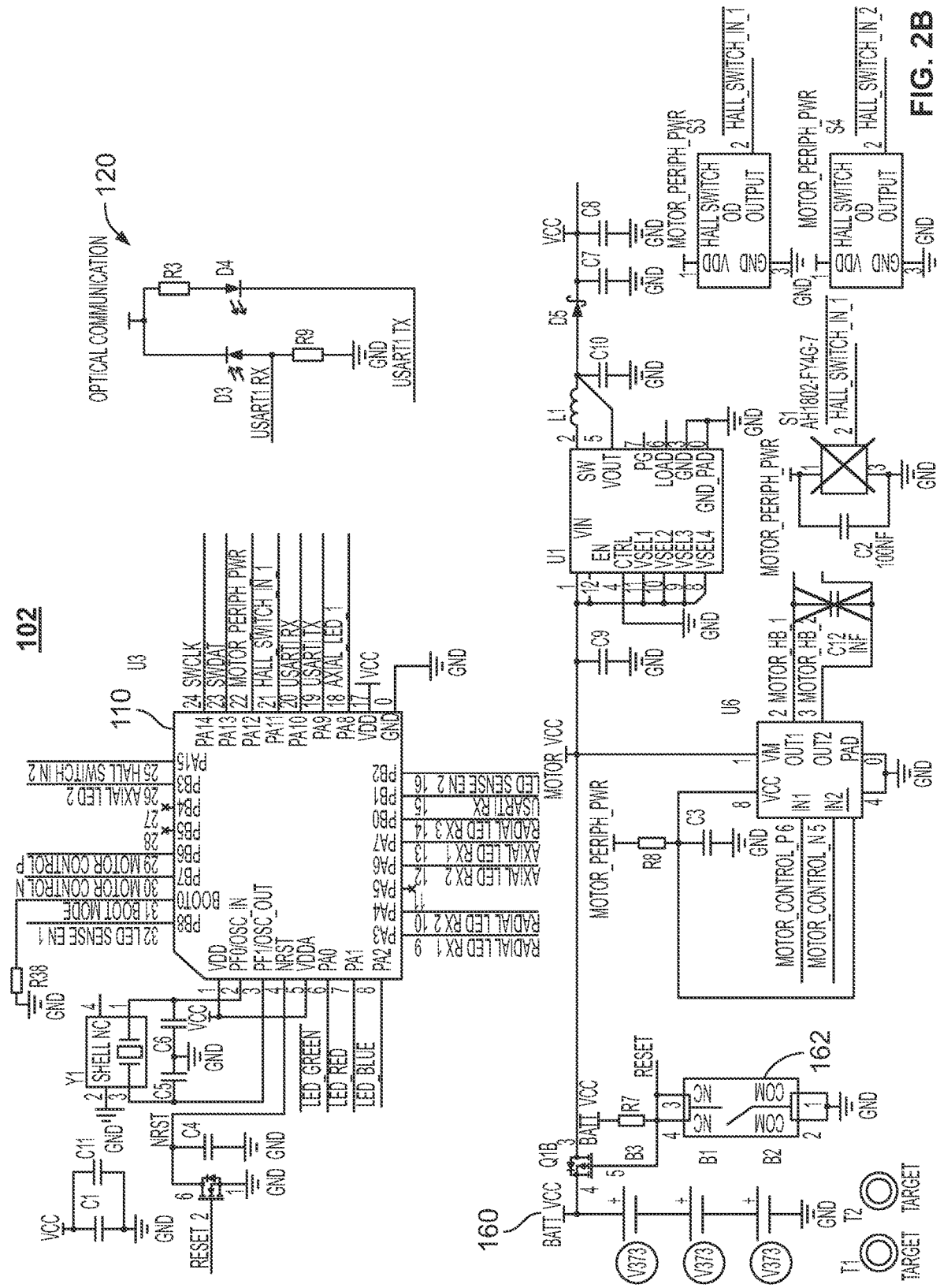
FIGS. 2B and 2C are an example embodiment of a circuit design that may be used in the ingestible device of FIG. 1A.
Figure 2C:
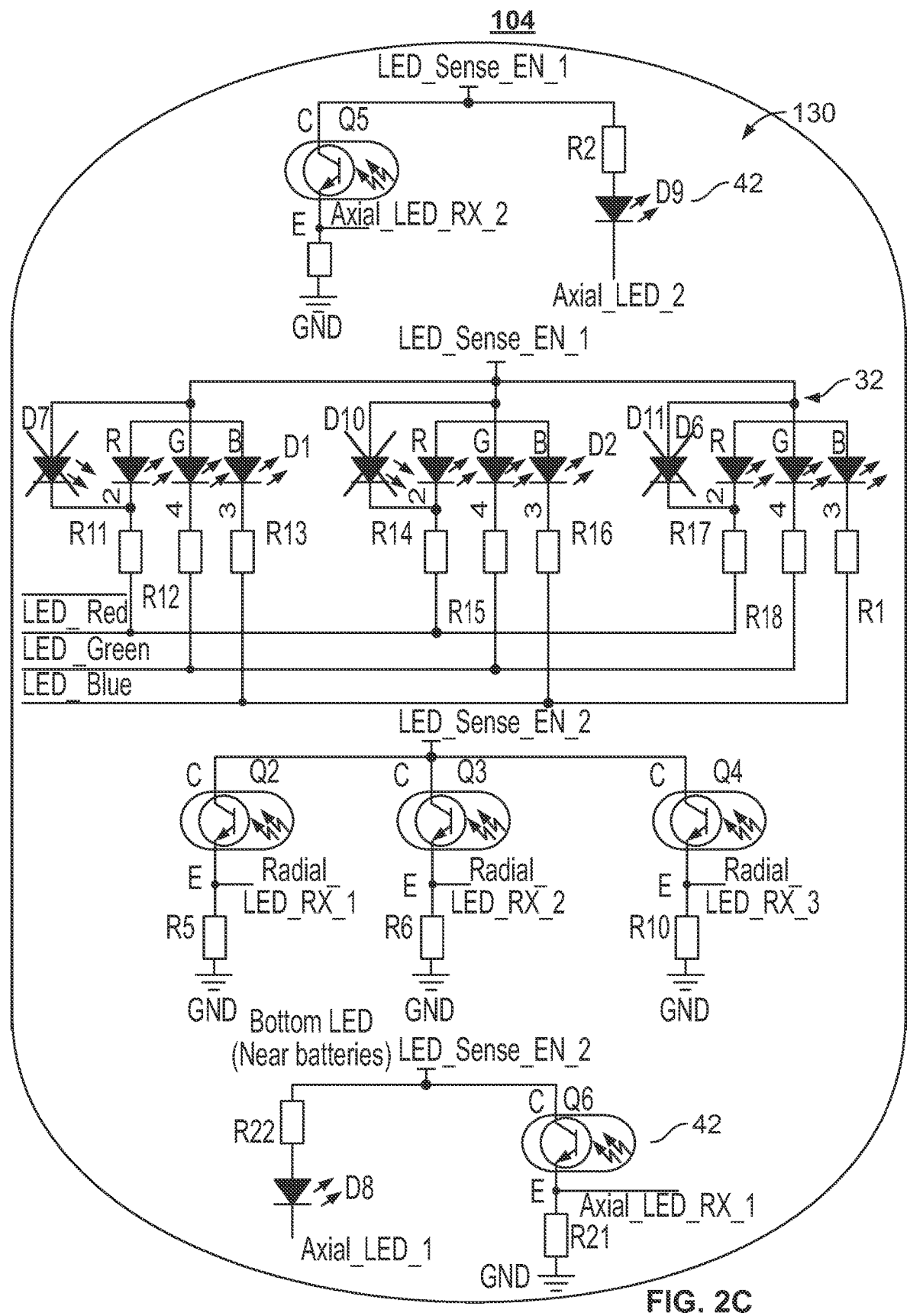

FIG. 2B is an example circuit design 102 of some of the electrical components of the ingestible device 10. It will be understood that the circuit design 102 is merely an example and other configurations and designs may similarly be used. FIG. 2C is an example circuit design 104 of the sensing sub-unit 130.

As noted above, some of the electronic components may be embedded on the PCB 30. FIGS. 2D and 2E illustrate a top view 106t and a bottom view 106b, respectively, of a circuit design of a flexible PCB 30.

The PCB 30 may consist of flexible printed circuits. Flexible printed circuits may maximize the utilization of space within the ingestible device 10 by enabling easier conformation to the dimensional constraints of the ingestible device 10. Increased flexibility allows more twisting, bending, and shaping of the PCB or certain parts of the PCB, ultimately leading to a smaller pill that is more robust to vibrational or torsional forces.

The PCB 30 in this example includes the communication sub-unit 120, the microcontroller 110, the sensing sub-unit 130, and other peripheral components that are described below. Electronic components located on the PCB 30 are electrically coupled to other components with one or more electronic signal pathways, traces or tracks.

The flexible PCB 30 may be fabricated using a combination of a flexible plastic material and a rigid material, such as a woven fiberglass cloth material, or any other suitable material. The resulting flexible PCB 30 can therefore exhibit both a flexible quality and a rigid quality. The flexible quality of the flexible PCB 30 enables the electronic components located on the flexible PCB 30 to conform to the dimensional constraints of the ingestible device 10. In particular, as generally illustrated in FIG. 1A, the flexible PCB 30 can be inserted into the first wall portion 14a. At the same time, the rigid quality of the flexible PCB 30 enables reinforcement of areas that may be susceptible to high levels of physical stress. For example, in some embodiments, contact terminals, such as 218b, 218b, that are used for connecting the flexible PCB 30 to the power supply 160 may have added reinforcement.

As illustrated in FIGS. 2D and 2E, the flexible PCB 30 includes one or more separate, but connected, segments. For example, the flexible PCB 30 may include a main PCB segment 202 and one or more smaller PCB segments 204 such as smaller PCB segments 204a and 204b. The smaller PCB segments 204 can be directly or indirectly connected to the main PCB segment 202. The main PCB segment 202 may be rolled into a generally cylindrical shape to conform to the structural dimension of the ingestible device 10.

As shown in FIG. 1B, the smaller PCB segments 204a and 204b may be folded into one or more overlapping layers and fitted into the ingestible device 10. In some embodiments, the smaller PCB segments 204a and 204b can be layered around the battery 18. It will be understood that the flexible PCB 30 may have different configurations, such as different shapes and sizes, and/or a different number of segments.

The electronic components can be located on any one of the main PCB segment 202 or the smaller PCB segments 204a and 204b. For example, as illustrated in FIGS. 2D and 2E, the main PCB segment 202 can include the microcontroller 110, the magnetic switch 162 and the radial sensors 32. The smaller PCB segment 204a can include the optical encoder 20 and the axial sensors 42. The smaller PCB segments 204a and 204b can also include respective power supply contact terminals 218a and 218b for engaging the battery 18. In some embodiments, other arrangements of these components on the flexible PCB 30 are possible.

Referring again to FIG. 1A, the first end portion 16a generally encloses the components at the first wall portion 14a of the ingestible device 10. The first end portion 16a and the first wall portion 14a may be fabricated with optically and radio translucent or transparent material. This type of material allows for transmission and reception of light, such as by the sensors 32, 42. In some embodiments, the first end portion 16a and the first wall portion 14a may be fabricated from plastic.

In some embodiments, the sensing sub-unit 130 can be oriented or provided with respect to the housing 12 in order to reduce any internal reflections resulting from an output of the sensing sub-unit 130. For example, the sensing sub-unit 130 can be oriented at a certain angle with respect to a circumference of the housing 12 so that minimal internal reflections are caused by the housing 12 when the output of the sensing sub-unit 130 reaches the housing 12. In some embodiments, a transition medium, such as certain oil-based substances, can be provided between the sensing sub-unit 130 and the housing 12 so that a refractive index of the transition medium and the sensing sub-unit 130 can match the refractive index of the housing 12, reducing reflections and scattering. In some embodiments the illuminator and detector of each sensor (e.g., the illuminator 32i and the detector 32d of the sensor 32) may be physically separated around the circumference of the device. For example, in the embodiments discussed in FIGS. 8A-8C, 19 and 20, separating the illuminator 32i and the detector 32d may further reduce internal reflections.

In some embodiments, the sensing sub-unit 130 includes an axial sensing sub-unit 42 and a radial sensing sub-unit 32 at different locations of the ingestible device 10 to help estimate the location of the ingestible device 10 within the body. The ingestible device 10, 300 moves within the body at variable speeds. Within the gastrointestinal tract, for example, the varying size, shape, and environments of the different tract segments can make location identification difficult.

Referring now to FIGS. 3A and 3B, shown therein are diagrams of an example ingestible device 300. FIGS. 3A and 3B generally illustrate an example configuration of the sensors 332, 342 with respect to certain components of the housing 12. FIG. 3A is a cross-sectional view 300A of the ingestible device 300 and FIG. 3B is a three-dimensional side view 300B of the ingestible device 300.

The axial sensing sub-unit 42 is located proximally to at least one of the first end portion 16a and the second end portion 16b. As shown in FIG. 3A, the axial sensor 342 is located proximally to the first end portion 16a. It will be understood that, depending on the structure of the ingestible device 300, the axial sensor 342 may be located proximally to the second end portion 16b instead. The radial sensing sub-unit 32 is generally located proximally to the radial wall 14. For example, as shown in FIGS. 3A and 3B, the radial sensor 332 is located proximally to a portion of the radial wall 14.

An examplary transit of the ingestible device 300 is shown in FIGS. 10A to 10C. The transit of the ingestible device 300 through a stomach 452, a small intestine 454 and then, a large intestine 456 is shown generally at 450A, 450B and 450C, respectively. The movement of the ingestible device 300 varies substantially depending on its location. The stomach 452, as shown in FIG. 10A, is a large, open and cavernous organ, and therefore the ingestible device 300 can have a relatively greater range of motion. On the other hand, the small intestine 454, as shown in FIG. 10B, has a tube-like structure and the ingestible device 300 is generally limited to longitudinal motion. The large intestine 456, similar to the stomach 452, is a large and open structure, and the ingestible device 300 can have a relatively greater range of motion as compared to its transit through the small intestine 454. By providing the axial sensing sub-unit 42 and the radial sensing sub-unit 32, different degrees and types of reflectance data are available depending on the shape and/or size of the transit location. The varying reflectance data is further described in FIGS. 13A, 13B and 13C.

In some embodiments, each axial sensor 342 and each radial sensor 332 can include an illuminator for directing an illumination towards an environment external to the housing 12 and a detector for detecting reflectance from the environment resulting from the illumination. The illumination can include any electromagnetic emission within the range of Infrared Light (IR), the visible spectrum and ultraviolet light (UV). An example operation of the sensors 342, 332 is described below with reference to FIGS. 7A to 7C.

FIGS. 7A to 7C illustrate the operation of axial sensor 342 and radial sensor 332 in different environments. In each of FIGS. 7A to 7C, the illuminators and detectors of the sensors 332 and 342 are shown for the ingestible device 300. The axial sensor 342 includes an axial illuminator 342i for transmitting axial illumination to the external environment and an axial detector 342d for detecting the axial reflectance from the external environment (i.e., external to the ingestible device 300). The axial reflectance may result from different illuminations, depending on the external environment.

Similarly, the radial sensor 332 includes a radial illuminator 332i for transmitting radial illumination to the external environment and a radial detector 332d for detecting the radial reflectance from the external environment. Similar to the axial reflectance, the radial reflectance may result from different illuminations, depending on the external environment. For example, in some embodiments there may be a plurality of radial illuminations, and the radial reflectance detected may result from the plurality of radial illuminations reflecting from the external environment and scattering in multiple directions. As shown in FIGS. 7A to 7C, the position of the radial illuminator 332i is such that the resulting radial illumination is in a different direction from the axial illumination generated by the axial illuminator 342i. In some embodiments, the radial illumination is substantially perpendicular to the axial illumination.

FIG. 7A illustrates a transit of the ingestible device 300 through an opaque liquid 410. The opaque liquid 410 is in contact with the radial wall 14 of the ingestible device 300, similar to the way opaque fluid within a large intestine (e.g., the large intestine 456 of FIG. 10C) may be in contact with the ingestible device 300 as it transits through a gastrointestinal tract under certain conditions. Therefore, the radial illumination transmitted by the radial illuminator 332i is nearly entirely internally reflected and detected by the radial detector 332d, resulting in a relatively large reflectance being detected. In this example, the axial detector 342d does not detect any reflectance because no substance or tissue is provided in front of the axial illuminator 342i.

FIG. 7B illustrates a transit of the ingestible device 300 near a tissue 412. The radial illumination transmitted by the radial illuminator 332i is partially reflected (and partially absorbed by the tissue 412) and detected by the radial detector 332d, similar to the way a radial illumination may interact with the tissue of a small intestine (e.g., the small intestine 454 of FIG. 10B) or other organs under conditions. Similar to FIG. 7A, the axial detector 342d in this example also does not detect any reflectance because no substance or tissue is provided within a range of the axial detector 342d. The amount of illumination reflected and absorbed by the tissue 412 may depend on the wavelength of the illumination. For example, red tissue may reflect illumination with a wavelength in the red spectrum (i.e., 620 nm-750 nm) well, resulting in a relatively high reflectance being detected by the ingestible device 300. In contrast, an illumination with a wavelength in the green spectrum (495 nm-570 nm) or blue spectrum (450 nm-495 nm) may be absorbed by the tissue, resulting in a relatively lower reflectance being detected by the ingestible device 300. In some embodiments, a plurality of radial or axial illuminations with different respective wavelengths may be used to help identify the location of the ingestible device 300 within a gastrointestinal tract, given that that different organs and portions of the gastrointestinal tract have different reflection properties.

FIG. 7C illustrates a transit of the ingestible device 300 through clear liquid with particulates 414. This type of environment may be similar to the environment found in a stomach (e.g., the stomach 452 of FIG. 10A) under certain conditions. As shown, the axial illumination and the radial illumination are reflected by the particulates 414a to 414d within the range of the respective axial illuminator 342i and radial illuminator 332i. It is also possible for some of the illumination to be reflected from one particulate to another, such as from particulate 414c to particulate 414b. The reflectance detected by each of the axial detector 342d and the radial detector 332d may not be limited to illumination generated by the respective axial illuminator 342i and radial illuminator 332i. It is possible for the axial detector 342d to detect a reflectance resulting from a radial illumination. Similarly, it is possible for the radial detector 332d to detect a reflectance resulting from an axial illumination. In some embodiments, it is possible to reduce this effect by having axial sensor 342 and radial sensor 332 use illumination with two different wavelengths. For example, if the radial sensor 332 has an illuminator 332i and a detector 332d that transmit and detect wavelengths in the red spectrum, and the axial sensor 342 has an illuminator 342i and a detector 342d that transmit and detect wavelengths in the infrared spectrum, the effect of the axial illuminator 342i on the radial detector 332d is reduced.

Various embodiments of the sensors 32, 42 are described below with reference to FIGS. 4A to 8C.

Referring now to FIGS. 4A and 4B, shown therein are diagrams of another example ingestible device 302. FIG. 4A is a cross-sectional view 302A of the ingestible device 302 and FIG. 4B is a three-dimensional side view 302B of the ingestible device 302. The ingestible device 302 includes an axial sensing sub-unit 42 having two axial sensors 342 and 344, and a radial sensing sub-unit 32 having two radial sensors 332 and 334.

As described with reference to FIGS. 3A and 3B, the axial sensor 342, or the first axial sensor, is located proximally to the first end portion 16a. The axial sensor 344, or the second axial sensor, is located proximally to the second end portion 16b. As shown in FIGS. 4A and 4B, the first axial sensor 342 and the second axial sensor 344 are located substantially opposite from each other with respect to the housing 12. The first axial illumination generated by the first axial sensor 342 will therefore be in a substantially opposite axial direction from the second axial illumination generated by the second axial sensor 344.

The radial sensor 332 of the ingestible device 302, or the first radial sensor, is located proximally to a first wall portion of the radial wall 14, while the radial sensor 334, or the second radial sensor, is located proximally to a second wall portion. As shown in FIGS. 4A and 4B, the first wall portion is spaced from the second wall portion by approximately 180 degrees along the circumference of the radial wall 14. The first radial illumination and the second radial illumination generated by the respective first radial sensor 332 and second radial sensor 334 are in different radial directions. As a result, the first radial illumination and the second radial illumination are transmitted in substantially opposite directions.

Generally, in embodiments in which the radial sensing sub-unit 32 is composed of two or more radial sensors 332, 334, the radial sensors 332 and 334 can be spaced along the circumference of the radial wall 14 by at least 60 degrees so that the resulting first radial illumination and the second radial illumination are in generally different radial directions from each other. Also, the separation between the radial sensor 332 and the radial sensor 334 can help to minimize internal reflections.

When more sensors are provided in the ingestible devices 10, 300, 302, more reflectance data will become available. As described with reference to FIGS. 10A to 12C, the reflectance data can increase the accuracy with which the in vivo location of the ingestible devices 10, 300, 302 can be identified.

Referring now to FIGS. 5A and 5B, shown therein are diagrams of another example ingestible device 304. FIG. 5A is a cross-sectional view 304A of the ingestible device 304 and FIG. 5B is a three-dimensional side view 304B of the ingestible device 304. Similar to the ingestible device 300, the ingestible device 304 includes an axial sensing sub-unit 42 having one axial sensor 342. However, unlike the ingestible devices 300 and 302, the radial sensing sub-unit 32 of the ingestible device 304 includes four radial sensors 332, 334, 336 and 338.

Figure 14A:
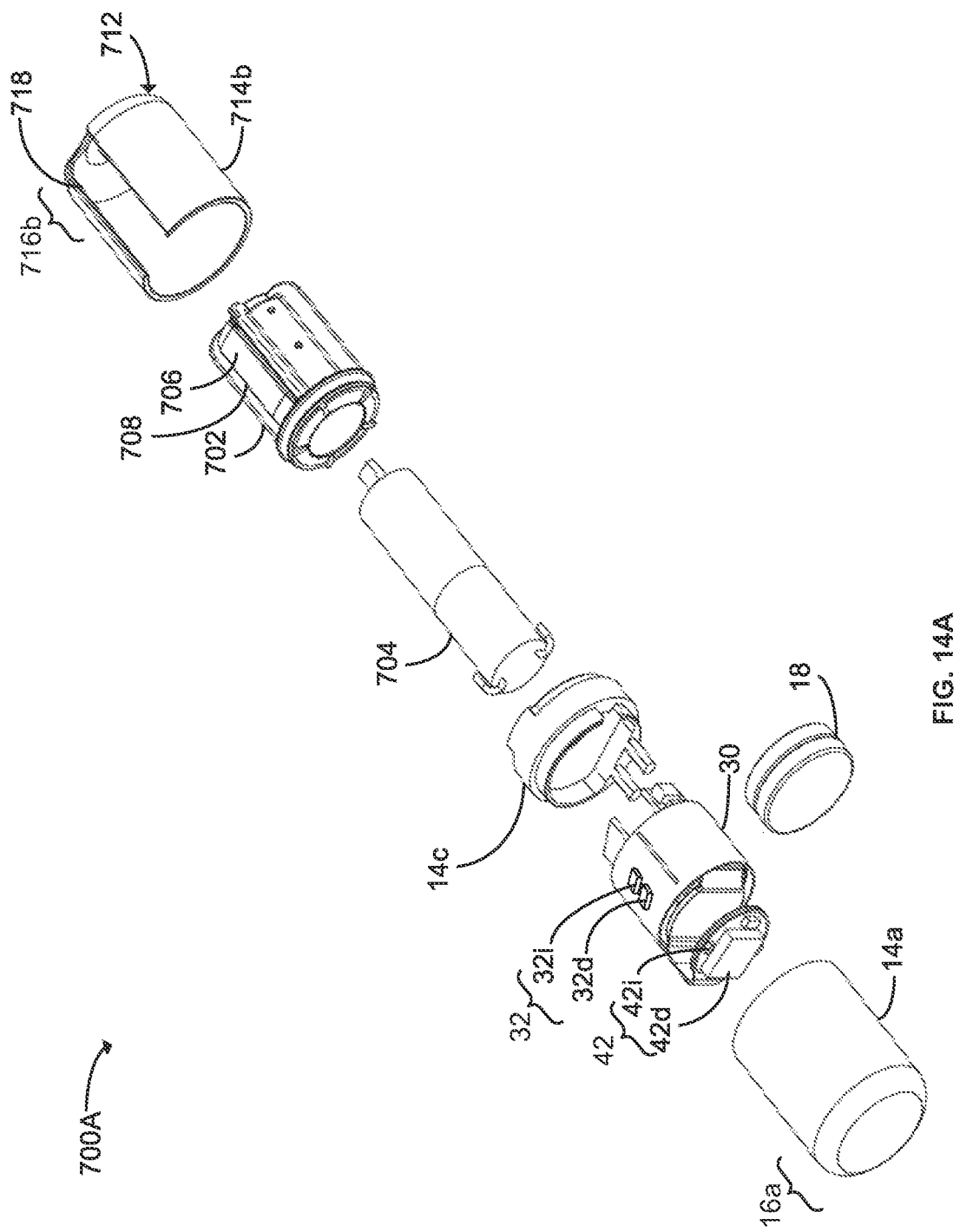
FIG. 14A is an exploded view of another example embodiment of an ingestible device.
Figure 14B:
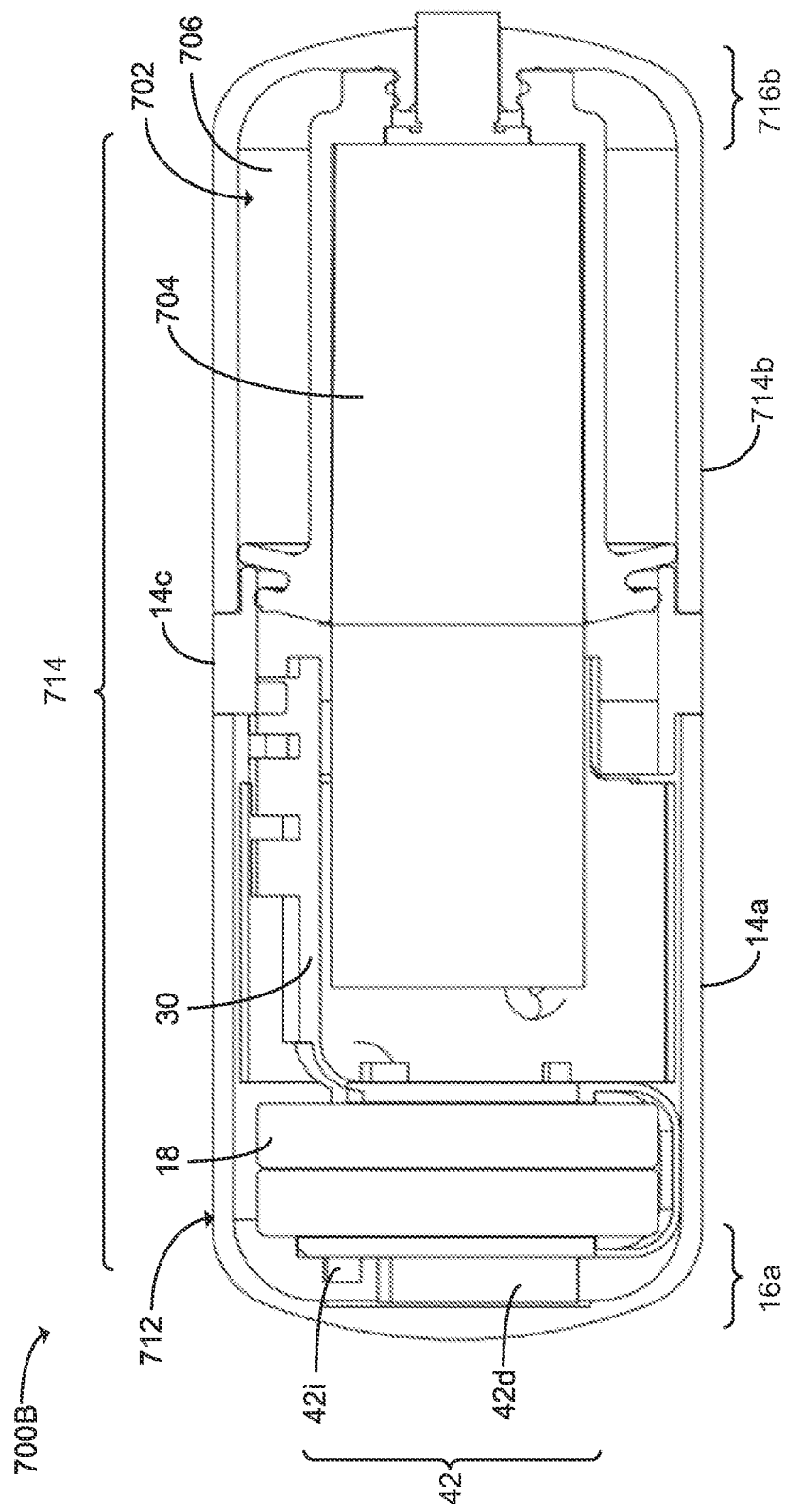
FIG. 14B is a cross-sectional view of the ingestible device of FIG. 14A.
Figure 25:
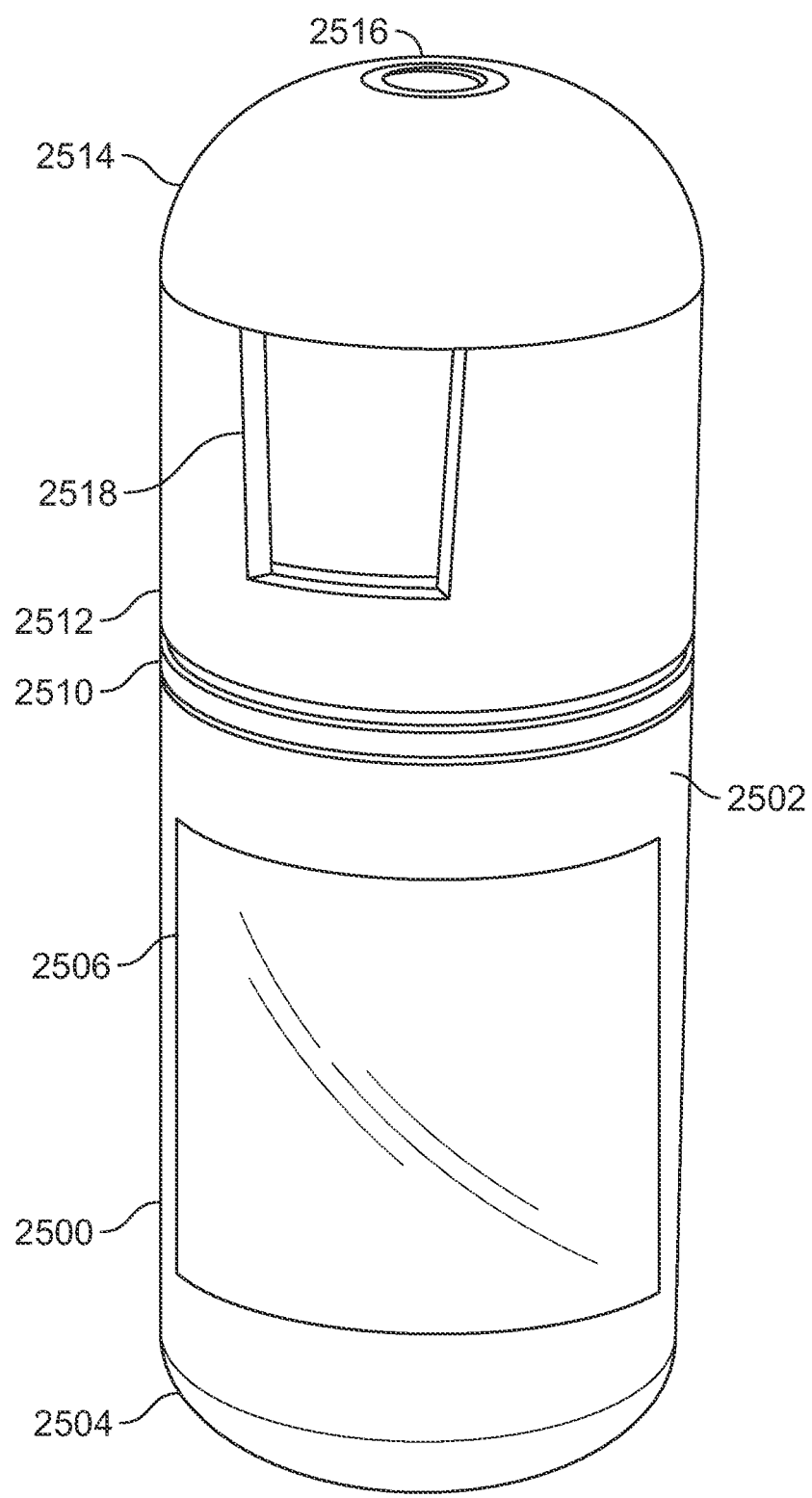
FIG. 25 is an external view of another embodiment of the ingestible device that may be used for sampling the gastrointestinal tract or releasing medicament.

As noted, the radial sensors 332, 334, 336 and 338 are generally provided so that they are spaced along the circumference of the radial wall 14 by at least 60 degrees. In the ingestible device 304, the radial sensors 332, 334, 336 and 338 may be positioned substantially equidistant from each other along the circumference of the radial wall 14. It is noted, that similar to the ingestible device 300, but unlike the ingestible device 302, the ingestible device 304 has a single axial sensor 342 near the first end portion 16a. In some embodiments, an ingestible device (e.g., the ingestible devices 300, 304) may have a sampling chamber located proximal to the second end portion 16b, substantially opposite from the location of the axial sensor 342. This embodiment is illustrated in FIGS. 14A, 14B, and 25. In some embodiments, an ingestible device (e.g., the ingestible devices 700, 2500) may have a chamber for storing a substance that is delivered to the gastrointestinal tract. These embodiments are illustrated in FIGS. 14A-14B and FIG. 25.

Referring now to FIGS. 6A and 6B, shown therein are diagrams of another example ingestible device 306. FIG. 6A is a cross-sectional view 306A of the ingestible device 306 and FIG. 6B is a three-dimensional side view 306B of the ingestible device 306. The ingestible device 306 includes an axial sensing sub-unit 42 having two axial sensors 342 and 344, similar to the ingestible device 302 of FIGS. 4A and 4B, and a radial sensing sub-unit 32 having four radial sensors 332, 334, 336 and 338, similar to the ingestible device 304 of FIGS. 5A and 5B.

Figure 8A:
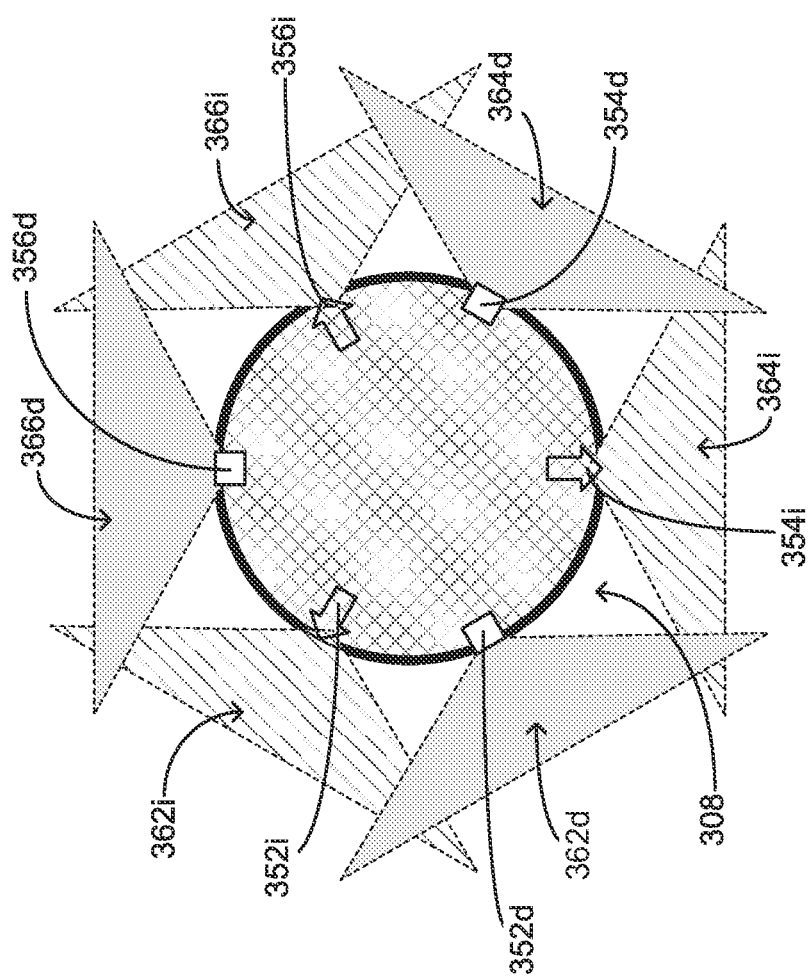
FIG. 8A is a cross-sectional view of an example embodiment of an ingestible device showing regions for transmitted and detected light that may be possible during operation.

Referring now to FIG. 8A, shown therein is a cross-sectional view of another example embodiment of an ingestible device 308. For ease of exposition, the axial sensing sub-unit 42 of the ingestible device 308 is not shown in FIG. 8A. The radial sensing sub-unit 32 includes three radial sensors 352, 354 and 356. In the ingestible device 308, the illuminator and detector of each of the respective radial sensors 352, 354 and 356 are separated from each other by approximately 60 degrees. With this configuration, each of the radial illuminators 352i, 354i and 356i has a respective illumination region 362i, 364i and 366i of approximately 120 degrees with respect to the circumference of the radial wall 14. Similarly, each of the radial detectors 352d, 354d and 356d has a respective detection region 362d, 364d and 366d of approximately 120 degrees with respect to the circumference of the radial wall 14.

The separation between the radial sensors 352, 354 and 356 can help to minimize internal reflections. For example, when the radial sensors 352, 354 and 356 in the ingestible device 308 are separated from each other by approximately 60 degrees, the radial sensors 352, 354 and 356 are generally equidistant from each other along the circumference of the ingestible device 308 and are also separated from each other at a maximum distance. As a result, internal reflection at the interface of the housing 12 can be minimized.

Figure 8B:
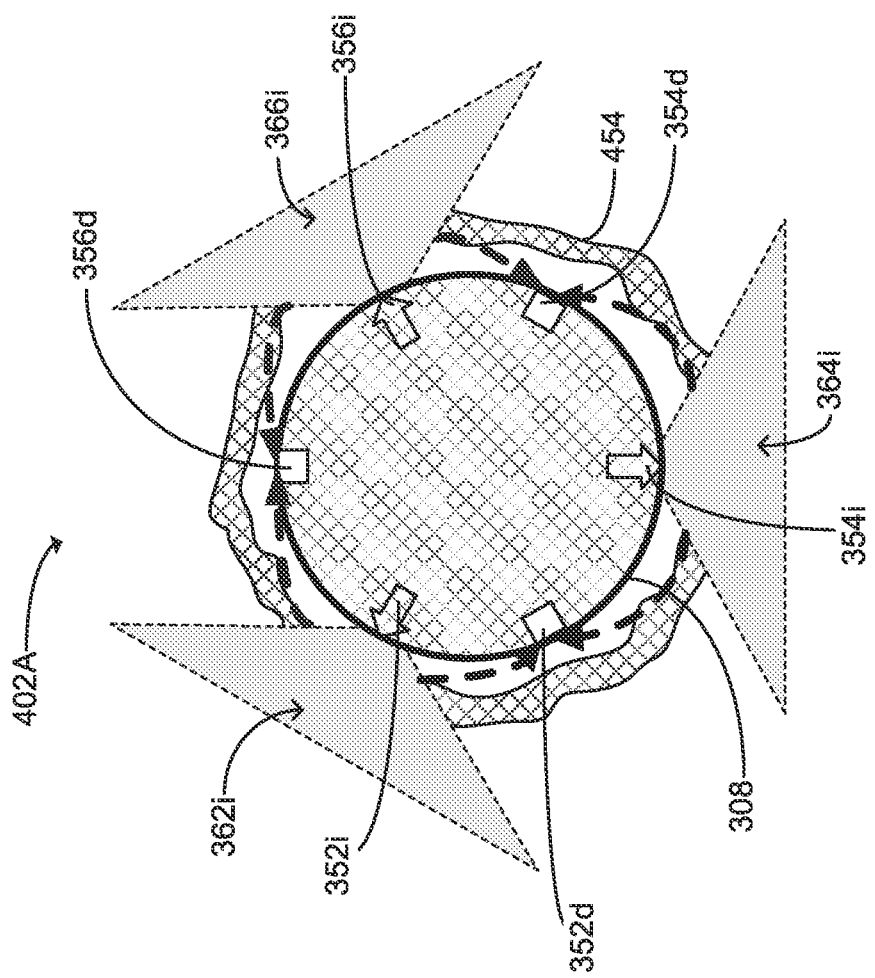
FIGS. 8B and 8C are diagrams of the ingestible device of FIG. 8A in an example operation.
Figure 8C:
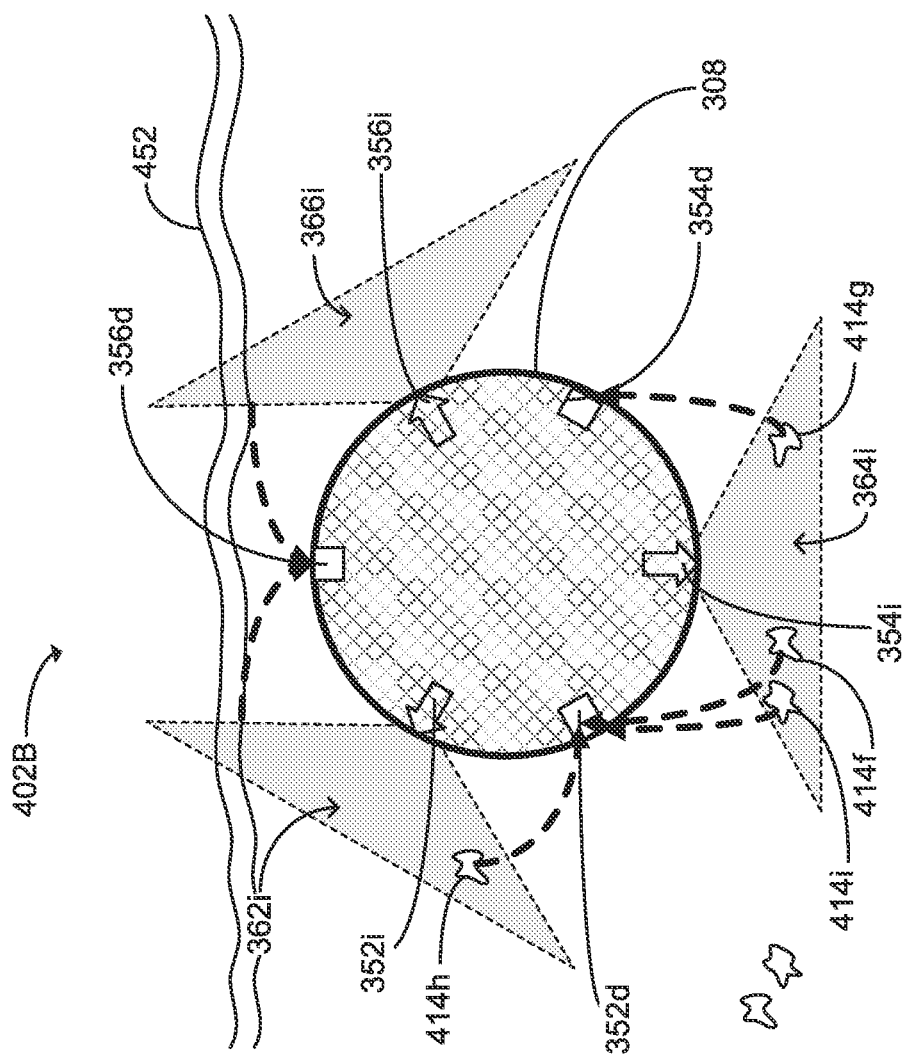

FIGS. 8B and 8C illustrate example operations of the radial sensors 352, 354 and 356 in different environments. FIG. 8B illustrates, at 402A, the ingestible device 308 transiting through the small intestine 454. Due to the tubular structure of the small intestine 454, the wall of the small intestine 454 closely surrounds the ingestible device 308. FIG. 8C illustrates, at 402B, the ingestible device 308 transiting through a larger space, such as the stomach 452. By physically separating the radial illuminators 352i, 354i and 356i and the radial detectors 352d, 354d and 356d in the fashion shown in FIG. 8A, a more variable reflectance can be detected as shown in FIGS. 8B and 8C.

For the ingestible devices 10, 300, 302, 304, 306 and 308 described herein, the axial sensing sub-unit 42 can include one or more axial sensors. At least one of the axial sensors may have an infrared Light-Emitting Diode (IR-LED) as an illuminator, and a detector sensitive to illumination in the infrared spectrum. The radial sensing sub-unit 32 can also include one or more radial sensors. The radial sensors may, in some embodiments, include a yellow-green LED emitting light having a wavelength of approximately 571 nm as an illuminator. In some embodiments, the radial sensors may comprise a green LED emitting light having a wavelength of approximately 517 nm and a red LED emitting light having a wavelength of approximately 632 nm. In some embodiments, the radial sensors may include an RGB LED package capable of emitting illumination at a plurality of different wavelengths.

When the radial sensors include the RGB LED package, the ingestible device 10 can sequentially emit different wavelengths. Certain tissues and fluids may have a different absorption rate for different wavelengths of illumination. With the use of the RGB LED, a larger range of reflectance data can be collected and analyzed.

For example, the RGB LED package can transmit a red illumination with a wavelength at approximately 632 nm and detect the reflectance resulting from the red illumination. The RGB LED package can then transmit a green illumination with a wavelength at approximately 518 nm, and detect the reflectance resulting from the green illumination. The RGB LED package can then transmit a blue illumination with a wavelength at approximately 465 nm and detect the reflectance resulting from the blue illumination. To determine the corresponding location of the ingestible device 10 based on the reflectance data collected by the RGB LED package at the various frequencies, the microcontroller 110 and/or an external processing module can compare each reflectance data series with each other. It may be possible that certain one or more portions of a reflectance data series at a particular wavelength may not be considered. Embodiments that determine the location of the device by comparing reflectance data from different wavelengths are illustrated in FIGS. 19-24.

The detected reflectance from each of the different types of illumination can be stored in the memory sub-unit 140 for later processing by the microcontroller 110. Additionally, in some embodiments this processing may be done by an external processing module.

In some embodiments, the axial sensors and radial sensors may include collimated light sources. The collimated light sources can orient reflective light in order to maximize reflectance from certain external environments, such as anatomies that are circular in shape. For example, the illumination may be provided by collimated light sources, which may be provided using LED binning or supplemental lenses, or by a combination of collimated and non-collimated light sources.

In some embodiments, after the sensing sub-unit 130 of the various ingestible devices 10, 300, 302, 304 and 306 described herein collects the reflectance data, the communication sub-unit 120 may transmit the detected radial and axial reflectance data to an external processing module. In some embodiments a device processing module (not shown) is provided in the ingestible devices 10, 300, 302, 304 and 306, and the reflectance data can be provided to the device processing module for processing. A processing module, regardless of whether it is, can then identify the location of the respective ingestible devices 10, 300, 302, 304 and 306 according to the methods described herein. In some embodiments, the microcontroller 110 may function as the processing module.

The processing module, as noted, may be the microcontroller 110 provided on the PCB 30, or an external processing module. When the detected data is to be provided to the external processing module for analysis, the communication sub-unit 120 may store the detected data in the memory sub-unit 140 and provide the detected data to the external processing module later (e.g., after the ingestible device 10, 300, 302, 304 and 306 exits from the body), or the communication sub-unit 120 may provide the detected data in real time using wireless communication components, such as a radio-frequency (RF) transmitter. However, it should be noted that some or all of the processing used to determine the location of the device may be performed by the microcontroller 110 within the device.

As described, the reflectance data collected by the sensing sub-unit 130 can be used to estimate an in vivo location of the ingestible device 10. As described with reference to FIGS. 9 to 12C, the axial reflectance data and radial reflectance data may be used to identify the different organs and/or transit points. For example, the level of the axial reflectance and the radial reflectance can be indicative of the type of the external environment.

Also, different materials can have different refractive indexes and so, the resulting light absorption characteristics can vary. For example, fluids tend to have a relatively lower refractive index than tissues. Depending on the type of organ, different materials may be present. In the stomach, for instance, some liquid and food particles may be present. On the other hand, in the small intestine, there is limited liquid but there may be air bubbles or gases. Based on the reflectance data, the processing module can determine certain characteristics of the environment in which the reflectance data was detected.

Figure 9A:
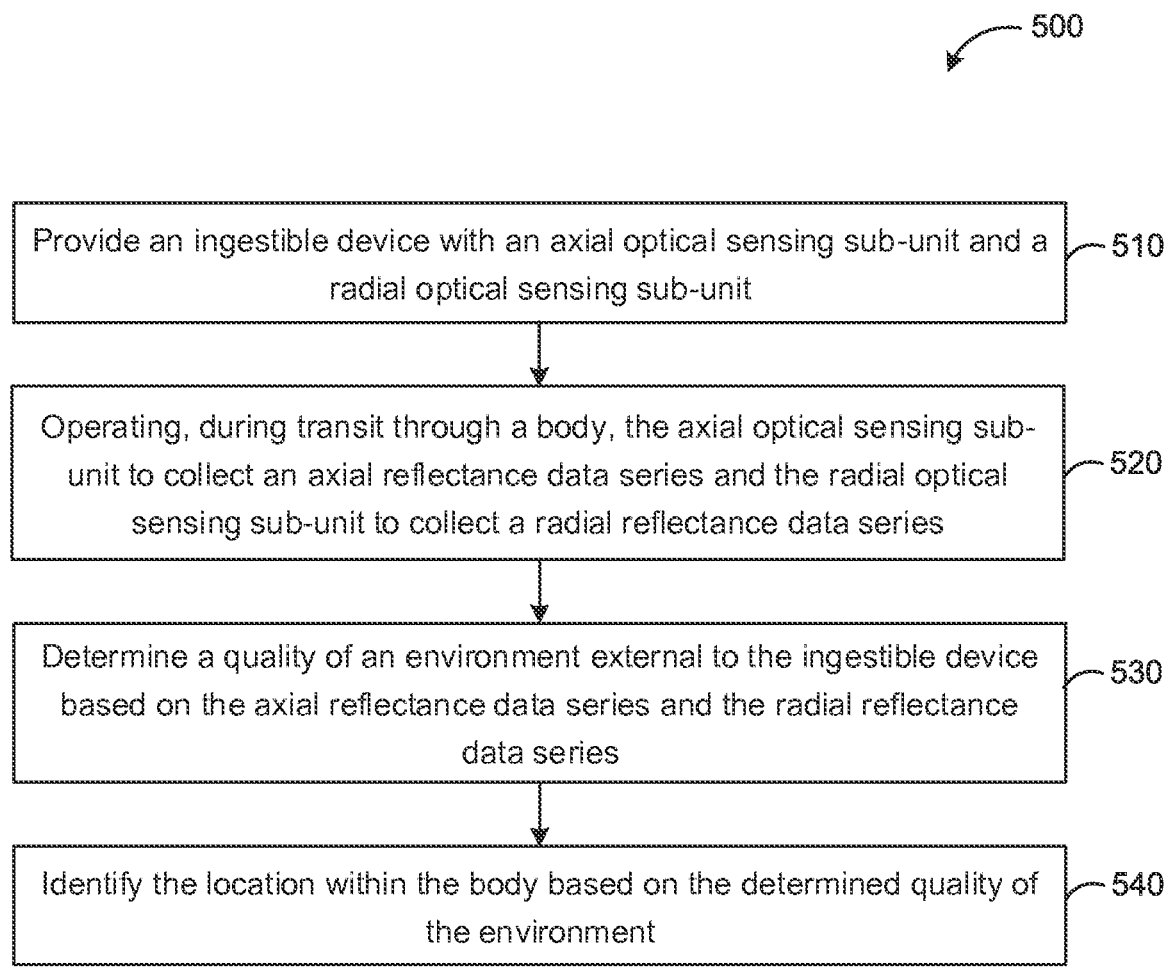
FIG. 9A is a flowchart of an example embodiment of a method of operation for the ingestible device described herein.

Reference is now made to FIG. 9A, which is a flowchart of an example method 500 of operation for the ingestible devices 10, 300, 302, 304, 306 and 308 or another embodiment thereof described herein. To illustrate the operation of the ingestible devices 10, 300, 302, 304, 306 and 308, reference is also made to FIGS. 10A to 12C.

At step 510, any of the ingestible devices described herein, such as 10, 300, 302, 304, 306 and 308, can be provided. As noted, the sensing sub-unit 130 can transmit illumination and collect reflectance data resulting from interaction by the illumination with the external environment.

The ingestible device 10, 300, 302, 304, 306 and 308 can be ingested by an individual and can then transit through the body of the individual. An example transit of each of the ingestible devices 300, 302, 304 and 306 within a portion of the GI tract is shown in FIGS. 10A to 12C.

At step 520, the sensing sub-unit 130 is operated to collect a reflectance data series as the ingestible device 10, 300, 302, 304, 306 and 308 transits through the body.

The reflectance data series can include an axial reflectance data series and a radial reflectance data series. Each of the axial reflectance data series and the radial reflectance data series can include one or more reflectance values that indicate a respective axial reflectance and radial reflectance detected by the sensing sub-unit 130 during at least a portion of the transit. The processing module may, in some embodiments, receive the reflectance data series in real time and operate to identify the in vivo location in real time and so, the processing module will only have access to a portion of the reflectance data series. In some embodiments, the processing module may receive the reflectance data after the ingestible device 10, 300, 302, 304, 306 and 308 has exited the body and so, the complete reflectance data series is available to the processing module.

FIGS. 10A to 10C generally illustrate the transit of the ingestible device 300 through the stomach 452, the small intestine 454 and then, the large intestine 456.

The stomach 452, as shown at 450A, is a relatively large space. The ingestible device 300, therefore, can move along all axes. The motion of the ingestible device 300 can cause high deviations in the reflectance data series. Also, the content of the stomach 452 may include relatively clear liquid but also particulates if the individual has not fasted, or not fasted sufficiently in advance of ingesting the ingestible device 300. Therefore, certain reflectance data may be caused by the presence of the particulates.

In the example of FIG. 10A, the ingestible device 300 is rotated several times as it transits through the stomach 452. It will be understood that the path and orientation of the ingestible device 300 are merely examples and that other paths and orientations are possible. At position "I", both the axial sensor 342 and the radial sensor 332 are facing a wall of the stomach 452 but at different distances. The resulting reflectance detected by the axial sensor 342 and the radial sensor 332 will likely vary due to the different absorption amounts caused by the different distances. The axial reflectance and the radial reflectance will result from interaction with, possibly, the wall of the stomach 452 and particulates 414 within the stomach 452. The axial sensor 342 is also likely to detect reflectance resulting from illumination generated by the radial sensor 332, and vice versa. The axial and radial reflectance values can vary with the contents that may be present within the stomach 452. If the individual has fasted sufficiently, there may be a fewer amount of particulates 414 in the stomach 452 and so, the resulting reflectance values may be relatively low.

At position "II", the axial sensor 342 faces a wall of the stomach 452 in closer proximity than at position "I". The axial sensor 342 will detect a high reflectance value from the wall of the stomach 452 due to the close proximity to the wall of the stomach. The radial sensor 332 does not directly face a wall of the stomach 452. However, because the radial sensor 332 is exposed to the contents of the stomach 452, the radial sensor 332 will detect reflectance resulting from the presence of any particulates 414 within the stomach 452.

The axial and radial reflectance detected by the axial sensor 342 and the radial sensor 332 at position "III" is similar to the reflectance detected at position "I". The values may vary due to different absorption amounts due to the content of the stomach 452.

At position "IV", however, the ingestible device 300 begins to transit through the pylorus, which is a much more narrow structure compared to the stomach 452. As shown in FIG. 10A, the axial sensor 342 faces towards the small intestine 454 and therefore, will continue to detect reflectance resulting from contents that may be present in the small intestine 454. The radial sensor 332, however, is in close contact with the pylorus wall, and will detect a high reflectance value resulting from illumination of the pylorus wall. Due to the close contact between the pylorus wall and the radial sensor 332, the axial sensor 342 will detect very little, if any, reflectance resulting from illumination transmitted by the radial sensor 332.

FIG. 10B illustrates the transit of the ingestible device 300 through the small intestine 454. As noted, the small intestine 454 has a tubular structure and therefore, the ingestible device 300 is restricted to longitudinal and rotational motion along its longitudinal axis. Also, the small intestine 454 generally includes limited liquid but may include a wet mucus layer and air bubbles or gas.

The axial reflectance and radial reflectance detected by the ingestible device 300 at positions "V" and "VI" are similar to the reflectance detected at position "IV". The axial sensor 342 faces one end of the small intestine 454 and will detect reflectance resulting from particulates 414, if present, or bends in the small intestine 454. The radial sensor 332, however, is in close contact with the wall of the small intestine 454, and will detect a high reflectance value resulting from illumination of the wall of the small intestine 454. Due to the close contact between the wall of the small intestine 454 and the radial sensor 332, the axial sensor 342 will detect very little, if any, reflectance resulting from illumination transmitted by the radial sensor 332.

After the ingestible device 300 transits through the small intestine 454, the ingestible device 300 enters the large intestine 456. Generally, the large intestine 456 is characterized by opaque brown contents due to the presence of fecal matter. The opaque contents may include liquids and/or solids. Depending on the type of illumination being generated, the reflectance detected at positions "VII", "VIII" and "IX" will vary. For example, it is possible that the reflectance detected at positions "VII", "VIII" and "IX" may be mostly internal reflectance when the illumination is within the visible spectrum (as shown in FIG. 7A in respect of the radial sensor 332). When the illumination is an IR illumination or a green illumination, the reflectance detected at positions "VII", "VIII" and "IX" may be associated with fairly high values due to the brown color of the content.

The transit of the ingestible device 302 through the stomach 452, the small intestine 454 and then, the large intestine 456 is described with reference to FIGS. 11A to 11C. As illustrated in FIGS. 4A and 4B, the ingestible device 302 includes two radial sensors 332 and 334 and two axial sensors 342 and 344. Additional reflectance values can be detected, accordingly.

Referring first to FIG. 11A, the reflectance values detected by the sensors 332, 334, 342 and 344 in the ingestible device 302 at position "I" is similar to the reflectance values detected by the sensors 332 and 342 in the ingestible device 300. The axial sensors 342, 344 and the radial sensors 332, 334 are generally exposed to the contents, if any, within the stomach 452.

At position "II", the first axial sensor 342 detects a different first axial reflectance than the second axial reflectance detected by the second axial sensor 344. The first axial sensor 342 is in close proximity with the wall of the stomach 452 whereas the second axial sensor 344 is farther away from a wall of the stomach 452. The first axial sensor 342 will therefore detect a high reflectance value due to the proximity to the wall of the stomach but the second axial sensor 344 will detect a reflectance value only depending on the type of contents present in the stomach 452. Based on a comparison of the largely varying first axial reflectance and second axial reflectance, the processing module can determine that the ingestible device 302 has not arrived at the small intestine 454.

At position "III", the second radial sensor 334 will detect a high reflectance value due to its proximity to the wall of the stomach 452. However, the first radial sensor 332, as described with reference to FIG. 10A, detects a reflectance value that varies with the amount of particulates 414. Again, the processing module can determine that the ingestible device 304 has not arrived at the small intestine 454.

As the ingestible device 302 moves into the pylorus, the first and second radial sensors 332 and 334 begin to detect a high reflectance value due to the close contact with the pylorus wall. The processing module can determine from the radial reflectance values that a transition may be occurring. The reflectance values detected by the first axial sensor 342 and the second axial sensor 344 will continue to depend on the contents of the small intestine 454 and the stomach 452, respectively, due to their orientation.

FIG. 11B illustrates the transit of the ingestible device 302 through the small intestine 454. The radial reflectance values detected by the ingestible device 302 will generally be similar to the radial reflectance values detected by the ingestible device 300 in FIG. 10B since the radial sensors 332 and 334 are in close proximity to the wall of the small intestine 454. The axial reflectance values detected by the axial sensors 342 and 344 will again vary depending on the contents that may be present in the small intestine 454.

As noted, the large intestine 456 is characterized by opaque brown contents. Therefore, the reflectance detected at positions "VII", "VIII" and "IX" as the ingestible device 302 travels through the large intestine 456, an example of which is shown in FIG. 11C, may be mostly internal reflectance when the illumination is within the visible spectrum, and may include high reflectance values when the illumination is an IR illumination or a green illumination due to the brown color.

Another example transit through the GI tract is now described for the ingestible device 304 with reference to FIGS. 12A to 12C. The ingestible device 304 includes four radial sensors 332, 334, 336 and 338 (as shown in FIGS. 5A and 5B) and an axial sensor 342.

The axial reflectance values detected in the example shown in FIGS. 12A to 12C are generally similar to the axial reflectance values detected in the example shown in FIGS. 10A to 10C. Accordingly, the axial reflectance values will not be described again with reference to FIGS. 12A to 12C. It is possible, in certain locations within the GI tract, that the axial sensor 342 may detect a greater amount of reflectance resulting from illumination generated from one of the radial sensors 332, 334, 336 and 338.

In FIG. 12A, the radial reflectance values detected by the radial sensors 332, 334, 336 and 338 at positions "I" and "II" will generally be similar to the radial reflectance values detected by the ingestible devices 300 and 302 in FIGS. 10A and 11A, respectively. The radial reflectance values detected by radial sensors 336 and 338 will vary depending on the width of the stomach 452. At position "III", the radial reflectance value detected by the radial sensors 336 and 338 will be similar to the radial reflectance detected by the radial sensor 332. From the radial reflectance values collected at positions "I", "II" and "III", the processing module can therefore determine that the ingestible device 304 has not entered the small intestine 454 since the radial reflectance data from the various radial sensors 332, 334, 336 and 338 are likely inconsistent values due to their dependence on the contents of the stomach 452 and their changing orientations.

Like the transit of the ingestible devices 300 and 302 shown in FIGS. 10A and 11A, the radial reflectance values collected at position "IV" will also indicate a pyloric transit is occurring. In the example shown in FIG. 12, since four different radial sensors 332, 334, 336 and 338 are in the ingestible device 304, a greater amount of reflectance values is provided and so, the processing module can more easily determine that transit to the small intestine 454 is occurring. Similarly, the transit of the ingestible device 304 through the small intestine 454 in FIG. 12B generates similar radial reflectance values as the configurations of the sensing sub-unit 130 of FIGS. 10B and 11B. However, as noted, the ingestible device 304 provides a greater amount of reflectance values and therefore, more reliable location detection.

Finally, as noted, the transit of the ingestible device 304 through the large intestine 456 may result in mostly internal reflectance due to the presence of mostly opaque contents in the large intestine 456 when the illumination is within the visible spectrum, and may result in high reflectance values when the illumination is an IR illumination or a green illumination due to the brown color.

In some embodiments, the sensing sub-unit 130 can include a temperature sensor. The temperature sensor can operate to collect a temperature data series as the ingestible device 10 transits through the body. The temperature sensor may operate while the sensors 32, 42 are in operation, or may operate in response to a trigger provided by the microcontroller 110 or by an external device (e.g., the base station) via the communication sub-unit 120. In some embodiments, the temperature may be used to determine when an ingestible device has entered or exited the gastrointestinal tract. For example, upon entering the stomach from an environment external to the body, the temperature measured by the ingestible device 10 may reflect a value close to body temperature. Similarly, upon naturally exiting the body, the temperature measured by ingestible device 10 may change to ambient room temperature.

Temperature values may be used, in some embodiments, in determining an in vivo location of the ingestible device 10. Temperature values in the stomach 452 can vary due to liquids and/or foods that may have been ingested. For example, a large drop in temperature values can generally indicate that the ingestible device 10 is still inside the stomach 452.

Referring again to FIG. 9A, at step 530, a processing module can determine a quality of the environment external to the ingestible device 10 using the reflectance data series collected by the sensing sub-unit 130. The reflectance data series will include an axial reflectance data series including axial reflectance values and a radial reflectance data series including radial reflectance values. Example reflectance data series are described with reference to FIGS. 13A to 13C.

The different segments of the GI tract are generally associated with different characteristics. The quality of the environment within the stomach 452 is generally inconsistent since the environment varies with particulates 414 that may or may not be present. The large space in the stomach 452 also allows for constant motion by the particulates 414 and the ingestible device 10, which further increases the variability of the environment of the stomach 452. The small intestine 454, on the other hand, is a more narrow space and typically includes consistent content types. Therefore, the small intestine 454 can be associated with a relatively homogenous quality. The large intestine 456, similar to the stomach 452, is a larger space than the small intestine 454 and therefore, allows for more variable motion by its contents and the ingestible device 10.

FIG. 13A is a plot 600A illustrating a reflectance data series collected by the ingestible device 300 of FIG. 3A during a transit through a GI tract of a subject. The y-axis of the plot 600A is provided as raw ADC values that represent the reflectance values and the x-axis of the plot 600A is provided in terms of time (hours). The plot 600A shows a radial reflectance data series 602A collected by the radial sensor 332 and an axial reflectance data series 604A collected by the axial sensor 342.

Between 0 to 3 hours, or during a transit period 610A, the radial reflectance data series 602A is particularly radical. As described with reference to FIG. 10A, the ingestible device 300 is likely transiting through the stomach 452 during the transit period 610A since the stomach 452 provides a large space for the ingestible device 300 to move and therefore, the resulting reflectance data series is likely to be largely varied.

At approximately 3 hours, or at transit point 620A, the reflectance data series decreases in value. Between 3 hours to approximately 7 hours, or during transit period 612A, the reflectance data series appears to be relatively stable. The decrease in the reflectance values at the transit point 620A and relatively consistent reflectance values thereafter until transit point 622A which generally indicates transit within the small intestine 454.

A transit time through the small intestine 454 of a healthy adult is approximately four hours in length. Also, as described with reference to FIG. 10B, the reflectance data series collected by the ingestible device 300 as it transits through the pylorus to the small intestine 454 increases in stability. In particular, the radial reflectance data series 602A is likely to include consistently high reflectance values as the ingestible device 300 transits through the small intestine 454 due to the close proximity to the wall of the small intestine 454.

The transit point 622A is at approximately 7 hours after the ingestible device 300 entered the GI tract. As shown in the plot 600A, a substantial spike occurs at the transit point 622A and the reflectance data series continues at approximately the increased value thereafter during a transit period 614A. During the transit of the ingestible device 300 through the large intestine 456, as described with reference to FIG. 10C, the axial sensor 342 and radial sensor 332 may detect mostly internal reflectance due to the content of the large intestine 456 being mostly opaque brown contents when the illumination is within the visible range. Accordingly, the transit point 622A likely indicates a transit into the large intestine 456.

Figure 13B:
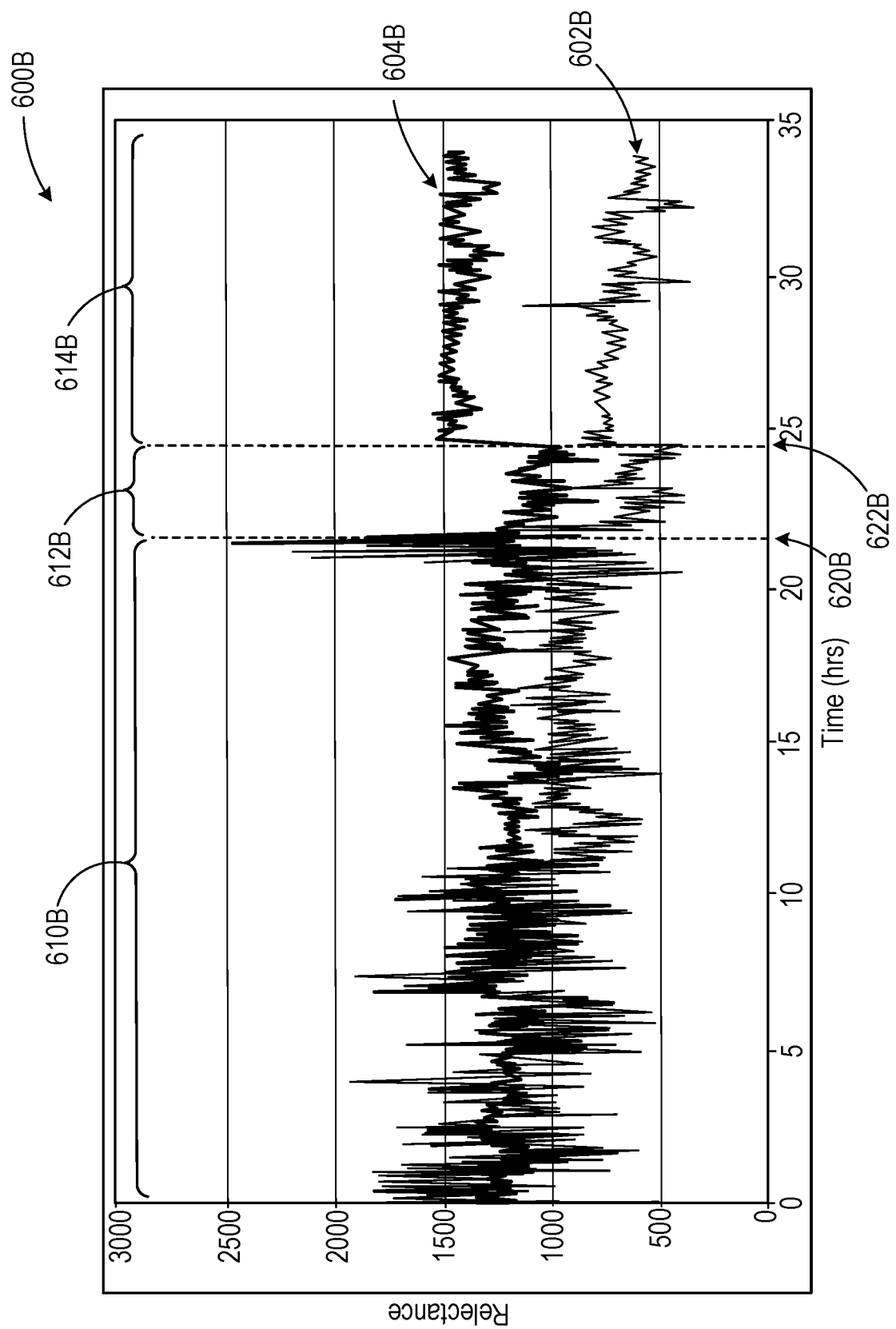

FIG. 13B is another plot 600B illustrating a reflectance data series collected by the ingestible device 300 of FIG. 3A during another transit through the GI tract of a subject. The plot 600B shows a radial reflectance data series 602B collected by the radial sensor 332 and an axial reflectance data series 604B collected by the axial sensor 342.

Similar to the reflectance data series shown in plot 600A, the plot 600B illustrates a transit point 620B between the stomach 452 and the small intestine 454, and a transit point 622B between the small intestine 454 and the large intestine 456. The transit period 612B through the small intestine 454 is approximately four hours, which is typical for a healthy adult. However, the transit period 610B through the stomach 452 is substantially longer than the transit period 610A. The variation between the transit periods 610A and 610B can be a result of various factors, such as, but not limited to, whether the individual fasted sufficiently before ingesting the device 300 and other possible events.

Figure 13C:
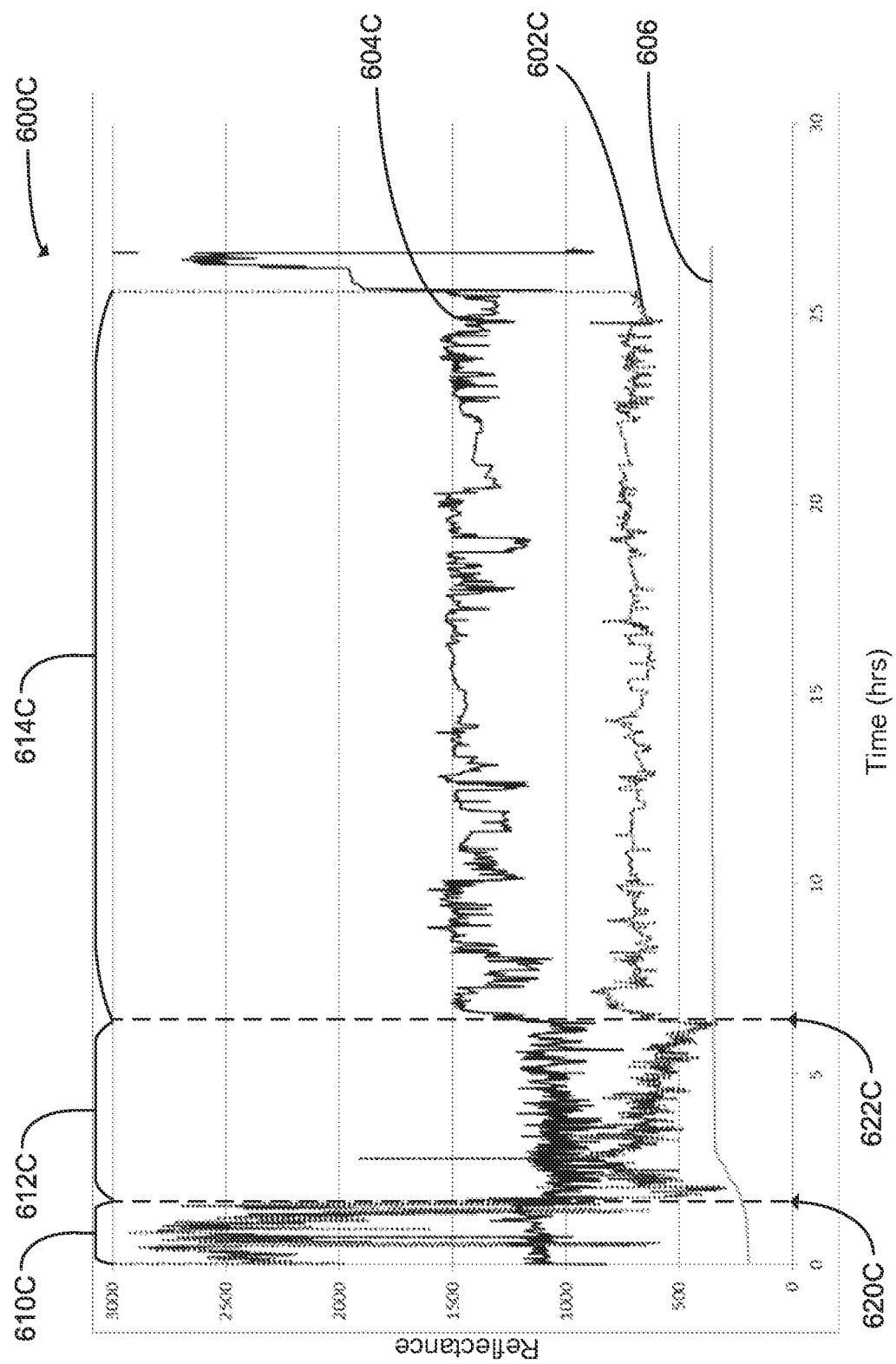

FIG. 13C shows another plot 600C illustrating a reflectance data series collected by the ingestible device 300 of FIG. 3A during another transit through the GI tract of a subject. The plot 600C shows a radial reflectance data series 602C collected by the radial sensor 332 and an axial reflectance data series 604C collected by the axial sensor 342. Unlike the plots 600A and 600B, the plot 600C also includes a temperature data series 606.

As shown approximately at 2.5 hours (at transit point 620C), the temperature in the temperature data series 606 increases slightly and is maintained at the increased temperature for most of the transit periods 612C and 614C. The increase in temperature at the transit point 620C can indicate a transit from the stomach 452 to the small intestine 454.

The reflectance data series shown in the example plots 600A to 600C are provided as raw ADC values. As illustrated in FIGS. 6A to 6C, it is possible for the processing module to generally identify the transit points 620, 622 within the GI tract based on the raw ADC values. The processing module may, in some embodiments, analyze the raw ADC values when determining the quality of the external environment of the ingestible device 10 in order to estimate the in vivo location of the ingestible device 10. An example method 550 of determining the quality of the environment external to the ingestible device 10 is described with reference to FIG. 9B.

Figure 9B:
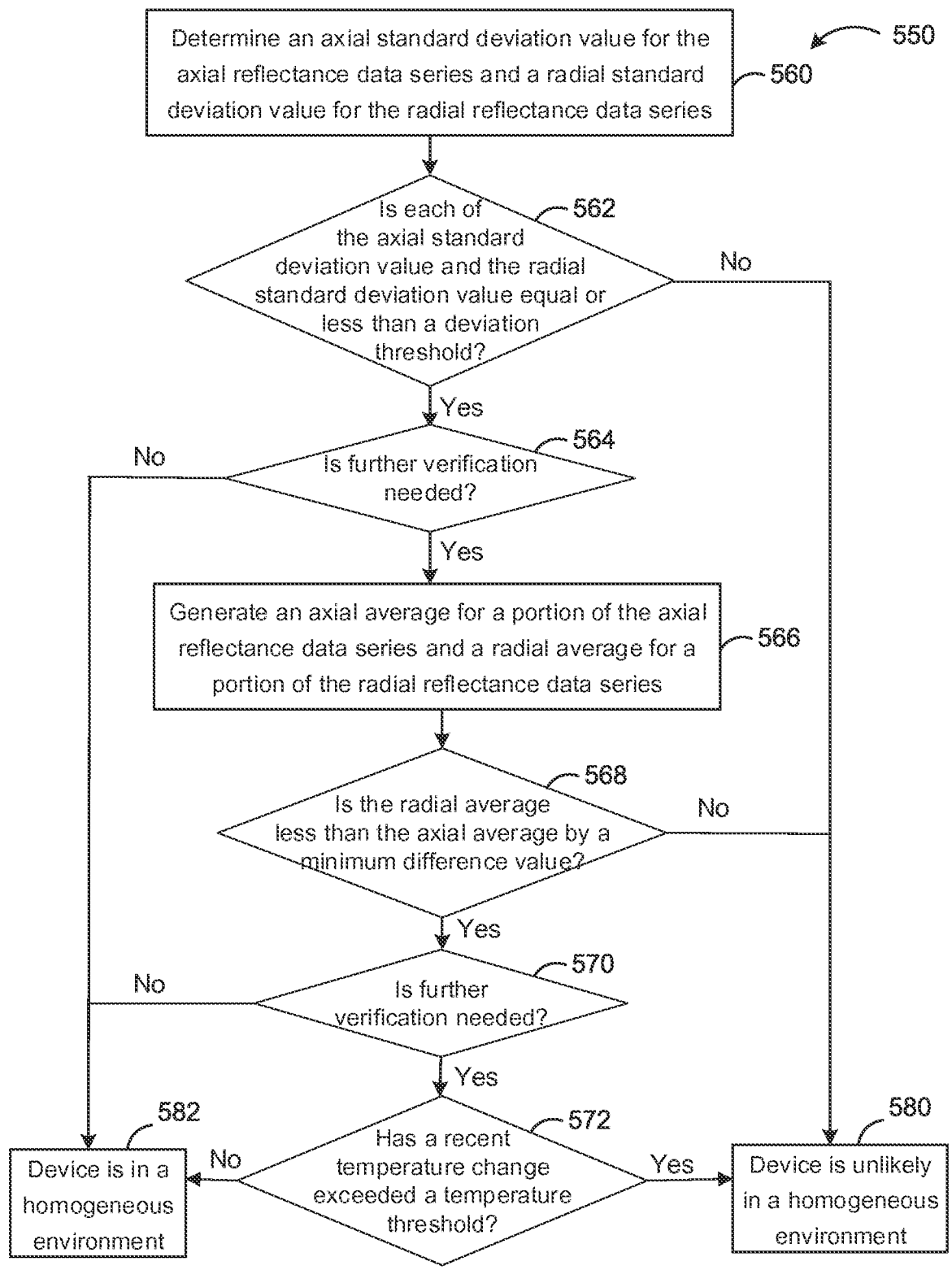
FIG. 9B is a flowchart of an example embodiment of a method of determining a quality of an environment external to the ingestible device described herein.

It will be understood that the steps and descriptions of the flowcharts of this disclosure, including FIG. 9B, are merely illustrative. Any of the steps and descriptions of the flowcharts, including FIG. 9B, may be modified, omitted, rearranged, performed in alternate orders or in parallel, two or more of the steps may be combined, or any additional steps may be added, without departing from the scope of the present disclosure. For example, in some embodiments the ingestible device may simultaneously calculate standard deviation and mean values to speed up the overall computation time. Furthermore, it should be noted that the steps and descriptions of FIG. 9B may be combined with any other system, device, or method described in this application, and any of the ingestible devices or systems discussed in this application could be used to perform one or more of the steps in FIG. 9B.

To estimate the in vivo location of the ingestible device 10, the processing module can determine standard deviations for each of the axial reflectance data series 604 and the radial reflectance data series 602, at step 560.

Typically, due to the varying environment of the stomach 452, the axial and radial standard deviation values are relatively high. The axial and radial standard deviation values decrease as the ingestible device 10 transits through the pylorus into the small intestine 454 as a result of the more homogenous environment of the small intestine 454. To identify the transit point 620 between the stomach 452 and the small intestine 454, the processing module can determine whether each of the axial standard deviation value and the radial standard deviation value satisfies a deviation threshold. Each of the axial and radial standard deviation values may satisfy the deviation threshold when each of the axial and radial standard deviation values is equal to or less than the deviation threshold.

The deviation threshold can include different values for the axial reflectance data series and the radial reflectance data series, or the same value for the axial and radial reflectance data series. The deviation threshold is a value that may be used to indicate that the standard deviation of the respective portions of the data series has reached a level that is representative of the environment of the small intestine 454. The deviation threshold may be varied depending on various factors, such as for addressing certain characteristics or requirements of an individual, when the ingestible device 10 is first initiated. The deviation threshold may be predefined, and/or may be varied during use based on the reflectance data collected by the sensing sub-unit 130 over predefined time periods.

In some embodiments, the deviation threshold may be adjusted during use based on some of the reflectance data. For example, an average can be determined for the reflectance data collected during a predefined period of time. When the determined average indicates that the reflectance data values are generally lower than expected, the processing module may decrease the deviation threshold accordingly to accommodate the lower reflectance data values. Similarly, when the determined average indicates that the reflectance data values are generally higher than expected, the processing module may increase the deviation threshold accordingly to accommodate the higher reflectance data values.

When the processing module determines that both the axial standard deviation value and the radial standard deviation value satisfies the deviation threshold, at step 562, the processing module may indicate that the quality of the external environment of the ingestible device 10 is homogenous (at step 582) and thus, the ingestible device 10 has likely arrived in the small intestine 454. Otherwise, the processing module may indicate the ingestible device 10 is unlikely in a homogenous environment (at 580). In some embodiments, the processing module may, at step 564, further verify the determination at step 562 and generate, at step 566, average values for a portion of the reflectance data series prior to determining the quality of the external environment to further verify the determination at step 562.

In some embodiments, a comparison between the axial standard deviation values and the radial standard deviation values may be conducted. To facilitate the comparison, the processing module may adjust the axial standard deviation values and the radial standard deviation values using an average of the corresponding reflectance data values.

Although determining the axial and radial standard deviation values satisfy the deviation threshold likely indicates a transition into the small intestine 454 (at step 582), there may be applications in which the accuracy of the location of the ingestible device 10 can be significant. For example, when the ingestible device 10 operates to collect samples specifically from the small intestine 454, the ingestible device 10 should be within the small intestine 454 prior to any sample collection—particularly because there is limited space in the ingestible device 10 for receiving samples.

To verify the in vivo location, the processing module can compare a portion of the axial reflectance data series with a portion of the radial reflectance data series. For example, at step 566, an average value can be generated for the portion of the axial reflectance data series to obtain an axial average and another average value can be generated for the radial reflectance data series to obtain a radial average. As described with reference to at least FIGS. 10B and 13A, in comparison with the axial reflectance values, the radial reflectance values generally decrease significantly as the ingestible device transits through the small intestine 454 due to the greater light absorption. Therefore, the radial average should be less than the axial average when the ingestible device 10 is within the small intestine 454. In some embodiments, the processing module may indicate the quality of the external environment is homogenous (at step 582) when the radial average is determined, at step 568, to be less than the axial average by a minimum difference value. Otherwise, the processing module may indicate the ingestible device 10 is unlikely in a homogenous environment (at 580).

Similar to the deviation threshold, the minimum difference value may be varied for various factors, such as for addressing certain characteristics or requirements of an individual, when the ingestible device 10 is first initiated. The minimum difference value may be predefined and/or may be varied during use based on data collected during the transit.

In some embodiments, the processing module may vary the minimum difference value based on a sum of the collected reflectance data and/or an absolute value of a sum of the axial reflectance data series and/or the radial reflectance data series.

The portion of the reflectance values that are selected for comparison can also vary. In some embodiments, after the initial detection of the transit point 620 based on the standard deviation values, the processing module may select a number of reflectance values following the transit point 620. The number of reflectance values may, in some embodiments, be adjusted during use based on the data collected during transit.

In some embodiments, the number of reflectance values may be adjusted based on a total axial standard deviation (which is a sum of the axial standard deviation values) and a total radial standard deviation (which is a sum of the radial standard deviation values). For example, when the total axial standard deviation and the radial standard deviation are both less than a detectable deviation threshold, the number of reflectance values can be reduced since the total axial standard deviation and the radial standard deviation can be considered negligible when lower than the detectable deviation threshold. The detectable deviation threshold generally indicates a minimum level of deviation in the reflectance values that, for the ingestible device 10, can vary the determination of the in vivo location.

As described with reference to FIG. 13C, the sensing sub-unit 130 may further include a temperature sensor for collecting temperature values. In some embodiments, the temperature sensor may be provided at the microcontroller 110 of the ingestible device 10.

The collected temperature values may be used by the processing module to further verify, at step 570 and step 572, the in vivo location. Since the temperature inside the stomach 452 is more variable than the temperature inside the small intestine 454, any significant changes in temperature can indicate that the ingestible device 10 has not entered the small intestine 454. For example, the processing module can indicate that a temperature change exceeding a temperature threshold, as determined at step 572, which can be a maximum allowable change in value, indicates that the environment is not homogenous (at step 580) and the ingestible device 10 is not in the small intestine 454. The temperature values can also indicate entry into the body (e.g., the temperature is likely to increase upon entry into the body) and/or exit from the body (e.g., the temperature is likely to decrease upon exit from the body).

In some embodiments, the temperature values can be used in temperature correction for an internal clock to improve time accuracy. The temperature values can be determined, using a lookup table or a formula, whether the time recorded at each waking cycle of the microcontroller 110 should be corrected due to the varying temperature during use of the ingestible device 10.

In some embodiments, when not being used (e.g., outside the body), the temperature sensor can detect temperature values from the surrounding environment to indicate the storage conditions of the ingestible device 10.

Referring again to FIG. 9A, at step 540, the processing module can identify the location of the ingestible device 10 based on the quality of the external environment determined at step 530.

The different segments of the GI tract are associated with different characteristics. The processing module can, therefore, identify the in vivo location using data collected from the external environment of the ingestible device 10 described herein. For example, the small intestine 454 is typically associated with a more homogenous environment due to the restricted structure and consistent content. Therefore, the processing module can indicate that the in vivo location of the ingestible device 10 is likely the small intestine 454 when the quality of the external environment is determined to be homogenous.

With the location detection methods described herein, such as method 500 for example, an in vivo location of the ingestible device 10 can be identified with a relatively high accuracy. The ingestible device 10, as a result, can have greater control on when certain tasks are conducted.

It will be understood that the steps and descriptions of the flowcharts of this disclosure, including FIG. 9A, are merely illustrative. Any of the steps and descriptions of the flowcharts, including FIG. 9A, may be modified, omitted, rearranged, performed in alternate orders or in parallel, two or more of the steps may be combined, or any additional steps may be added, without departing from the scope of the present disclosure. For example, in some embodiments the ingestible device may begin to determine a quality of the environment using existing data, while simultaneously operate axial and radial sensing sub-units to gather new data. Furthermore, it should be noted that the steps and descriptions of FIG. 9A may be combined with any other system, device, or method described in this applications, and any of the ingestible devices or systems discussed in this application could be used to perform one or more of the steps in FIG. 9A.

As noted, any of the ingestible devices described herein, such as the ingestible devices 10, 300, 302, 304, 306 and 308, can be used for different tasks. In some cases, the ingestible device 10 may be used for collecting usable samples from the contents of the GI tract (e.g., 100 µL sized samples) and maintaining each sample in isolation from one another until the samples are extracted. In some embodiments, the ingestible device 10 may be used for releasing substances into the body in a controlled manner. In this case, prior to introducing the ingestible device 10 into the body, at least one of the chambers in the ingestible device 10 may be loaded with a substance, either in a liquid or dry-powder format.

In some embodiments, an ingestible device for identifying a location within the GI tract of a body (e.g., the ingestible device 700) contains a medicament, including therapeutics, and a means for controlled administration of the medicament for treatment of a disease. In some aspects, the means for controlled administration may include control means for dispensing the medicament to specific areas of the GI tract, according to the device's location in the gastrointestinal tract as determined by the methods provided herein. For example, in the case of ileocolitis, the most common type of Crohn's disease, dispensing of a medicament at the site of inflammation, e.g., the ileum, would make it readily available to the inflamed, diseased tissue, while at the same time minimizing the concentration in systematic circulation. As a result, the use of an ingestible device to deliver a medicament could reduce potential side effects. Similar methods may be used to treat other GI diseases where local delivery provides benefits. For example, treatment of GI tumors or treatment of celiac disease may be effectively targeted.

In some embodiments, the ingestible device for identifying a location within the GI tract of a body (e.g., the ingestible devices 10, 300, 302, 304, 306, and 700) collects data on transit from one location in the GI tract to another (e.g., transit time). For example, the device may measure transit times through different regions of the GI tract such as the stomach, small and large intestines. Such transit times may be useful for detecting pathological conditions of motility such as gastroparesis and slow transit constipation. By recognizing specific anatomical locations and determining transit time as described herein, the device provides an accurate method of measuring whole gut transit time (WGTT), gastric emptying time (GET), small bowel transit time (SBTT) and colonic transit time (CTT). In some embodiments, this may result in a wealth of additional knowledge as compared to ingestible devices that rely on pH or imaging data to determine location.

In some embodiments, the ingestible device 10 may be configured to collect samples after releasing one or more substances into the body (in a predefined sequence in the case of multiple reagents) and the ingestible device 10 may then collect a resulting physical sample from the body. For example, substances that may inhibit enzymatic and chemical processes may be released into the body before a sample is collected (e.g., for preventing potential degradation of the collected samples in order to obtain a "snap-shot" of the environment from which the sample was collected).

An example ingestible device 700 configured to autonomously conduct the location detection methods described herein and to carry substances is described with reference to FIGS. 14A, 14B and 15. As can be seen from FIGS. 14A, 14B and 15, certain components of the ingestible device 700 correspond to components of the ingestible device 10 (see for example FIGS. 1A, 1B and 2A). Therefore, the components that are similar in ingestible devices 10 and 700 will not be described again.

FIGS. 14A and 14B illustrate an exploded view 700A and a cross sectional view 700B, respectively, of the ingestible device 700. The ingestible device 700 is configured in a similar manner as the ingestible device 10 but the ingestible device 700 is configured to store substances (e.g., samples, reagents, medicaments or therapeutics). Similar to the ingestible device 10, the ingestible device 700 includes a battery 18 and a PCB 30. The PCB 30 has, at least, the axial sensing sub-unit 42 and the radial sensing sub-unit 32 embedded thereon. The battery 18 and PCB 30 are enclosed by the first wall portion 14a and the first end portion 16a. However, unlike the ingestible device 10, the ingestible device 700 includes a motor 704 and a storage sub-unit 702 that are enclosed by a second wall portion 714b and a second end portion 716b configured to receive an end of the motor 704. The second wall portion 714b may also act as a chamber enclosure.

The storage sub-unit 702 includes chambers, such as 706, for storing substances. The substances may be collected from the body during transit as samples and/or released to the body during transit. In some cases, the substances may be loaded into the ingestible medical device 700 before use so that the substances can be released in the body during transit. An access port 718 is provided on the second wall portion 714b to accommodate entry or exit of the substances into or from the chambers 706. The second wall portion 714b may be referred to as a chamber enclosure.

The chambers 706 are generally long rectangular grooves along a length of the cylindrical-shaped storage sub-unit 702. However, it will be understood that the chambers 706 can take any shape and the shape may vary depending on the intended application of the ingestible device 700. Each of the chambers 706 can be isolated from one another so that one or more discrete substances may be stored either from sampling during operation or to be stored prior to usage for release during operation. Generally, each of the chambers 706 has dimensions to store a usable sample size, such as a volume of about 100 µL, for example.

Each chamber 706 has a corresponding chamber opening 708. The chamber openings 708 may span an arc of approximately 60°. Therefore, areas that are not recessed (e.g., each with a span of approximately) 60° may be provided between each of the chamber openings 708 on the storage sub-unit 702. In some embodiments, the chamber openings 708 and the corresponding chambers 706 are unevenly distributed around the circumference of the storage sub-unit 702. For example, the chamber openings 708 and the corresponding chambers 706 may be located closer together when it is undesirable for the ingestible device 700 to pause between each collection or release of a substance. In some embodiments, the chamber opening 708 can span an arc having a different circumferential extent.

As described above, the chambers 706 in the storage sub-unit 702 may be used for storing samples that are collected from the GI tract and/or storing substances for release into the GI tract. Therefore, both the chamber openings 708 and the access port 718 are sufficiently large to accommodate movement of substances into or out of the chambers 706 through peristaltic motion.

The operation of the storage sub-unit 702 is further described with reference to FIG. 15.

Similar to the ingestible device 10, a connecting wall portion 14c can connect the first wall portion 14a with the second wall portion 714b. A housing 712 is formed from the first end portion 16a, the second end portion 716b, and the radial wall 14 formed by the first wall portion 14a, the connecting wall portion 14c, and the second wall portion 714b. As shown in FIG. 14B, the radial wall 714 extends from the first end portion 16a to the second end portion 716b.

Due to the storage sub-unit 702 and the motor 704, the axial sensing sub-unit 42 is limited to axial sensors located proximal to the first end portion 16a. However, the radial sensing sub-unit 32 may include any number of radial sensors as described herein. For example, the ingestible device 700 can include a radial sensing sub-unit 32 that is configured in a similar way as shown in FIGS. 5A, 4A and 8A.

Also, the storage sub-unit 702 and the chamber enclosure 714b can be configured differently. For example, the storage sub-unit 702 may instead rotate and the chamber enclosure 714b may be stationary. Other embodiments of the storage sub-unit 702 and the chamber enclosure 714b may be used.

Figure 15:
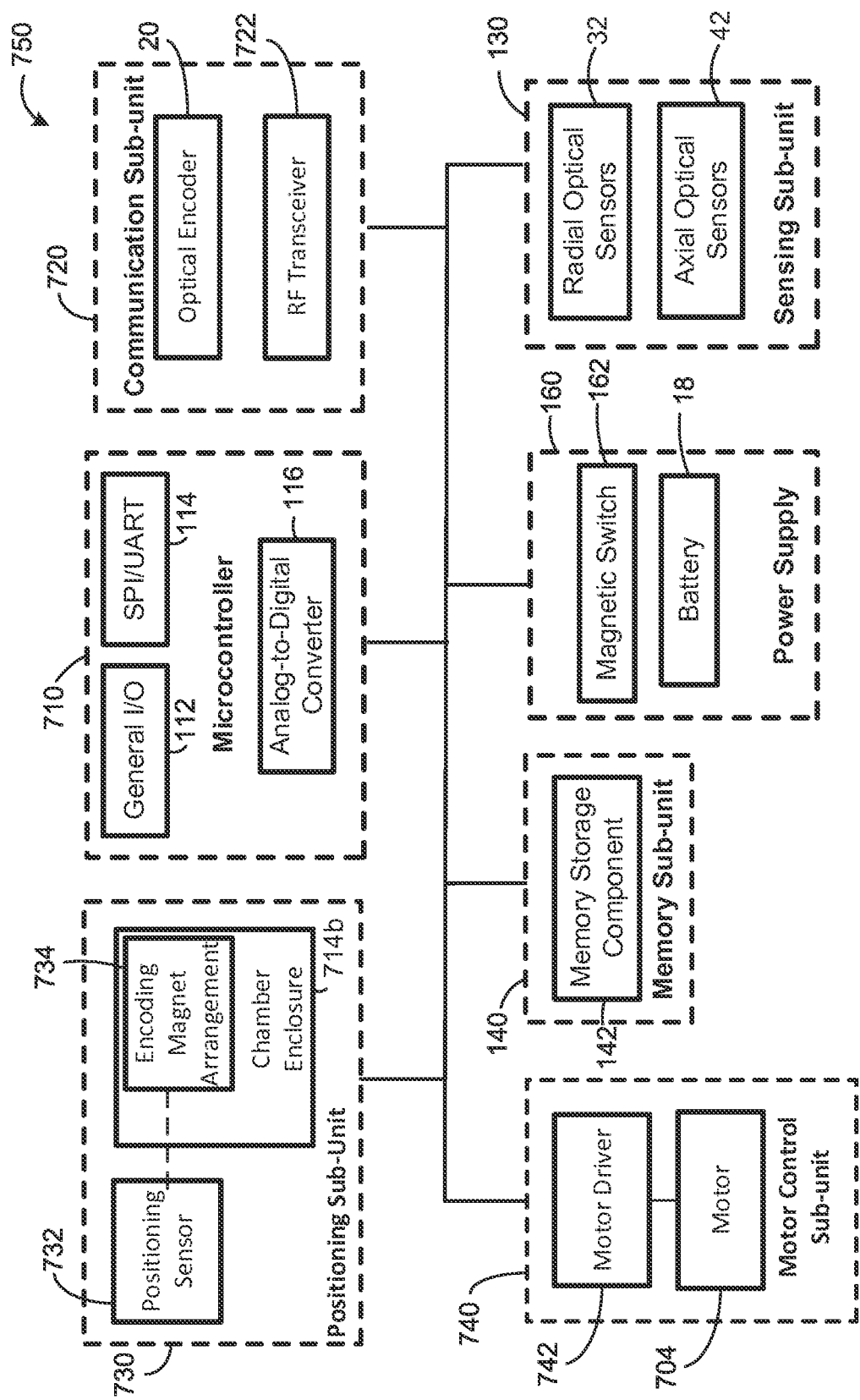
FIG. 15 is an example block diagram of electrical components that may be used for the ingestible device of FIG. 14A.

FIG. 15 is a block diagram 750 of an example embodiment of electrical components that may be used for the ingestible device 700 of FIG. 14A.

The memory sub-unit 140, the power supply 160 and the sensing sub-unit 130 can operate in a similar manner for both the ingestible devices 10 and 700.

The communication sub-unit 720 in the ingestible device 700 includes the optical encoder 20, like the ingestible device 10, and also a RF transceiver 722. It is possible for the ingestible device 10 to also include the RF transceiver 722 for conducting wireless communication with an external processing module.

The RF transceiver 722 may be considered a peripheral device to the microcontroller 710. Therefore, the microcontroller 710 may initiate RF communications by sending the RF transceiver 722 data specifying the channel on which the RF transceiver 722 is to transmit as well as power, frequency, and other parameters that are used for RF communication as well as data that is specific to the operation of the ingestible device 700.

In some embodiments, the RF transceiver 722 in the ingestible device 700 may facilitate real-time telemetry during collection and/or release of a substance. For example, the RF transceiver 722 may transmit data associated with the operation of the ingestible device 700 and/or samples collected to the base station in real-time.

The microcontroller 710 may be provided using a similar processor as the microcontroller 110. However, the microcontroller 710 in the ingestible device 700 will be configured to handle additional functionalities, such as those provided by a motor control sub-unit 740 and a positioning sub-unit 730.

For a majority of the time that the ingestible device 700 is in operation, the microcontroller 710 is likely the only component that draws power from the power supply 160. When the microcontroller 710 is not in use, most of the other components can be powered down.

The positioning sub-unit 730 and the microcontroller 710 can operate together to determine a location of the access port 718 relative to each of the chamber openings 708. The positioning sub-unit 730 may include a magnetic sensor or a sensor.

When the magnetic sensor is used for determining a location of the access port 718, an encoding magnet arrangement 734 is also included in the ingestible device 700. As a magnet in the encoding magnet arrangement 734 rotates over the magnetic sensor, the magnetic sensor senses the magnet and generates a corresponding positioning signal, which can be a quasi-sinusoidal or square wave depending on the particular implementation.

The motor control sub-unit 740 includes a motor driver 742 and the motor 704. The motor driver 742 may be a Dual Full Bridge Driver that comprises a DPDT switch and protective circuitry including a resistor-diode combination in a single package.

When the motor 704 receives power, it will rotate the chamber enclosure 714b by a distance corresponding to the received power. Since the encoding magnet arrangement 734 is embedded in the chamber enclosure 714b, the encoding magnet arrangement 734 rotates with the chamber enclosure 714b. When the magnets rotate over the magnetic sensor, the magnetic sensor senses a varying magnetic strength from the magnets and encodes this information in a positioning signal which is then sent to the microcontroller 710 through the A/D Converter 116.

Unlike the microcontroller 710, in some aspects the motor 704 may have a high discharge capacity. For example, at 3V operating voltage, a 6 mm pager gear-motor may draw a current of 120 mA when unloaded and a current of 230 mA when stalled. It will be understood that the 6 mm motor is merely an example of a motor that can be used in the ingestible device 700 and that other types of motor with similar operating characteristics and varying dimensions may be used.

The power supply 160 may need to supply a high energy density and to discharge a high current on demand (e.g., to discharge a high level of current for momentary periods of time). An example of such a power supply may be multiple silver oxide batteries (e.g., two 30 mAh batteries that operate at 1.55V each, amounting to a combined 3.1V). Silver oxide chemistry provides relatively high energy density and can discharge sufficient current on demand (e.g., 150 millicoulombs/second with a maximum of 250 millicoulombs/second). The high energy density of the silver oxide chemistry also indicates that the silver oxide battery has a long battery life, with a low self-discharge rate of approximately 5%/yr. Batteries formed using silver oxide chemistry may also have a compact form and such forms exist as standard coin cell form factors. Another example battery chemistry which possesses high energy density, long life, and high on-demand discharge rates can include lithium polymer.

The motor 704 is coupled to the microcontroller 710 for receiving power from the power supply 160. The motor 704 can be coupled to the microcontroller 710 via control circuitry. The motor 704 may then rotate the chamber enclosure 714b around the storage sub-unit 702. Generally, the motor 704 is implemented such that it provides a high torque without external gearing. In some embodiments, the motor 704 may be a miniature DC motor. In some embodiments, the DC motor may be brushless. For example, a miniature DC motor with a 700:1 reduction planetary gearing (e.g., as manufactured by Precision Microdrive) may be used. The 700:1 reduction planetary gearing generally provides a proportional increase in torque and decrease in revolutions per minute (RPM).

As illustrated in FIG. 14B, two concentric layers form around the motor 704. In order to maximize space inside the ingestible device 700, the storage sub-unit 702 and the chamber enclosure 714b are built to fit concentrically around the motor 704. A first layer around the motor 704 is the storage sub-unit 702 and a second layer around the motor 704 is the chamber enclosure 714b.

Figure 16:
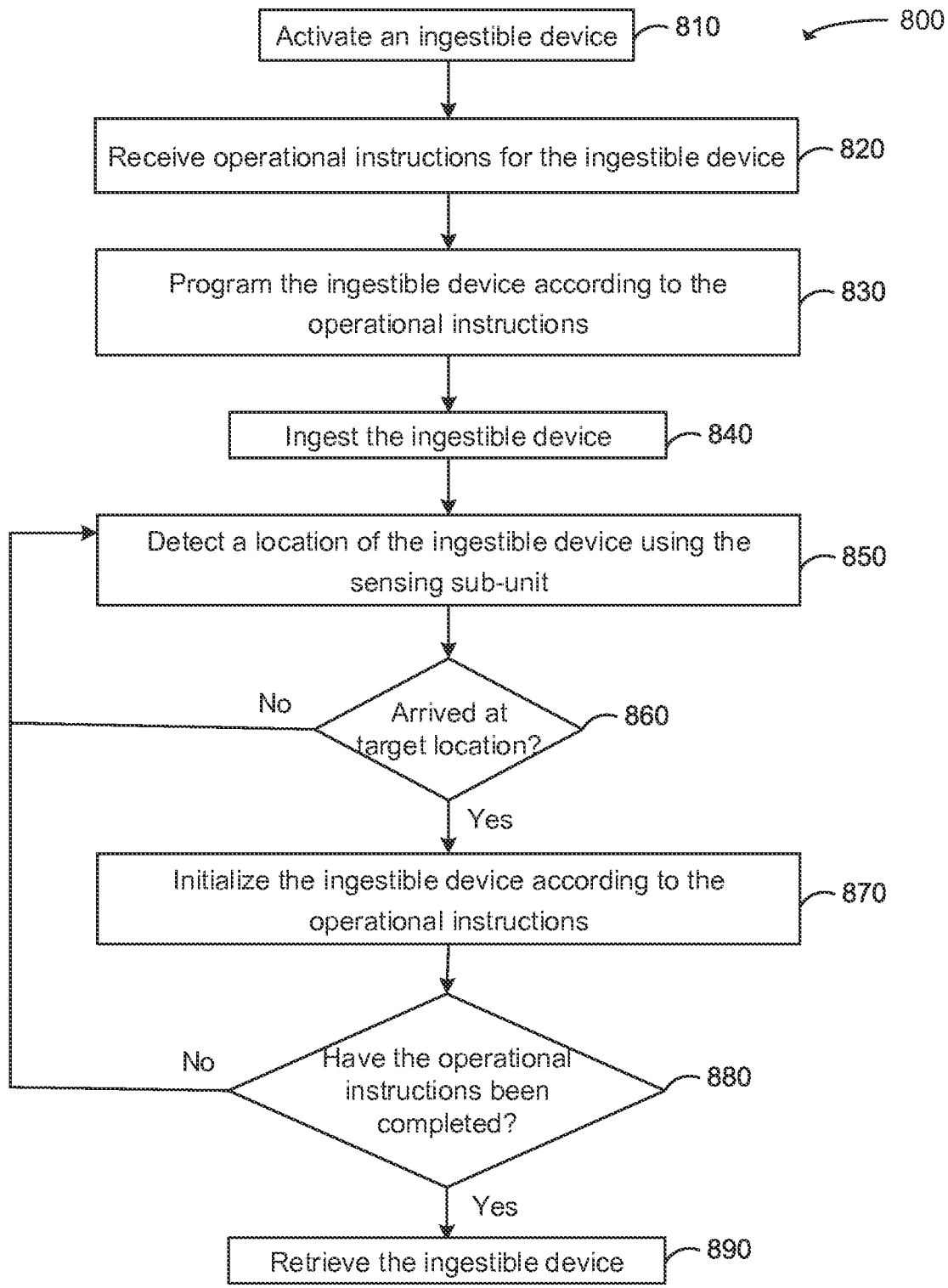
FIG. 16 is a flowchart of an example embodiment of a method of operation for the ingestible device of FIG. 14A.

Referring now to FIG. 16, shown therein is a flowchart of an example method 800 of operating the ingestible device 700.

At step 810, the ingestible device 700 is activated. The ingestible device 700 may be activated by activating the magnetic switch 162. For example, the ingestible device 700 can be removed from the magnetic field to switch the magnetic switch 162 to an 'ON' position. Current may then flow through the electrical pathways in the ingestible device 700 (e.g., pathways on the PCB 30).

In response to the ingestible device 700 being activated, the microcontroller 710 can begin to detect and initialize peripheral components and/or devices. The microcontroller 710 can detect, through the general I/O 112, for example, whether one or more peripheral devices are present on a bus by sending out a series of requests to specific addresses associated with the general I/O 112. In response, any peripheral device that is present then sends an acknowledging signal to the microcontroller 710. If the microcontroller 710 does not receive a response within the designated time frame, the microcontroller 710 operates as if no peripheral device is present. The designated time frames can vary. An example time frame can be 20 seconds. The microcontroller 710 then initializes the peripheral devices that are present. The initialization process may vary with different peripheral devices.

After the microcontroller 710 initializes the peripheral devices, the microcontroller 710 generally places the peripheral devices in a low-energy state, or may even completely power down the peripheral devices with non-volatile memory, in order to avoid unnecessary consumption of power.

At step 820, the microcontroller 710 receives operational instructions for the ingestible device 700.

After initializing the peripheral devices, the microcontroller 710 may poll the communication sub-unit 720, such as the RF transceiver 722, for a start signal from a base station. This start signal may generally be followed by operational instructions from the base station. The start signal and the operational instructions may be provided wirelessly through IR or RF transmission depending on the particular implementation of the ingestible device 700.

The base station can include a dock that acts as a peripheral device to an external computer and may communicate with the external computer through a COM Port of the external computer using the SPI protocol. In some embodiments, the base station includes a microcontroller, such as the processing module for identifying the in vivo location of the ingestible devices described herein, and a transceiver. The transceiver is selected to facilitate communication between the ingestible device 700 and the base station.

Figure 17B:
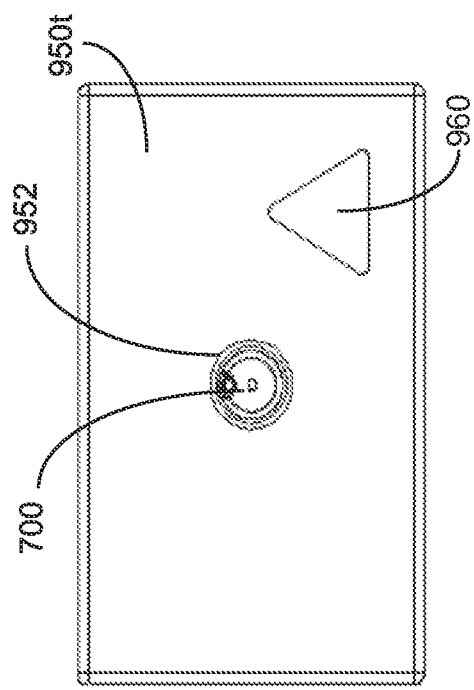
FIGS. 17A to 17C are different views of an example embodiment of a base station that may be used with an ingestible device.
Figure 17C:
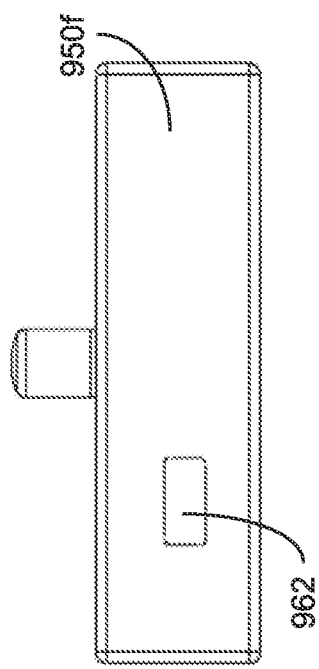
Figure 17A:
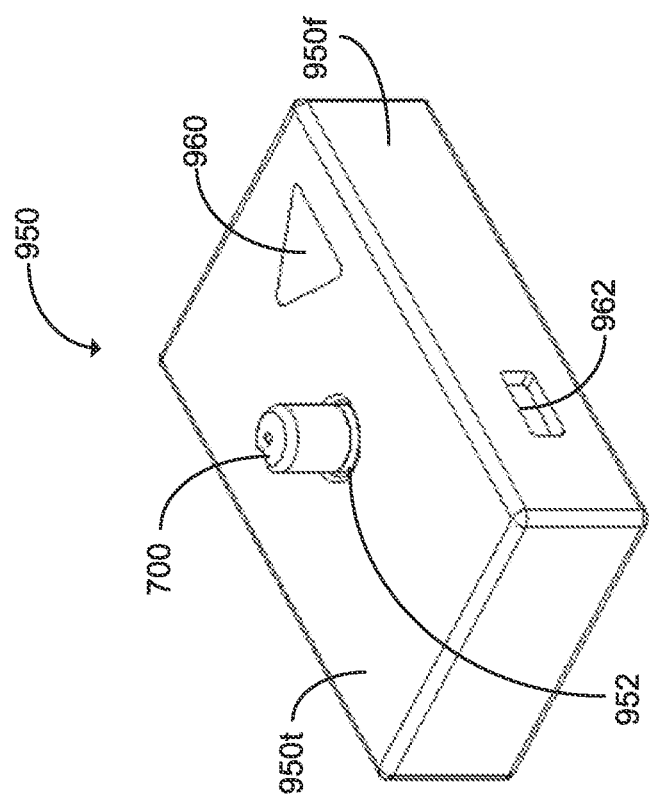

Referring now to FIGS. 17A to 17C, shown therein are different views of an example embodiment of a base station 950.

The base station 950 includes a programming and charging dock 952, a magnetizing region 960 at a top surface 950t, and a Universal Serial Bus (USB) connection port 962 at a front surface 950f. The magnetizing region 960 can be used to trigger the magnetic switch 162. When the magnetic switch 162 is activated, the magnetic switch 162 can reset the microcontroller 110 so that the microcontroller 110 proceeds to activate the ingestible device 700. After being activated by the microcontroller 110, the ingestible device 700 can engage with the programming and charging dock 952 to receive the operating instructions. The operating instructions may be received via the USB connection port 962 or wireless.

In some embodiments, the base station 950 may also include a chamber engagement dock for retrieving samples from the ingestible device 700 or inserting substances into the ingestible device 700.

The base station 950 may, in some embodiments, include LEDs for indicating a status of the programming and charging dock 952 as well as certain commands that are received from an external computer. For example, the LEDs may be used to indicate Emergency Stop and Override commands coming from the computer when extracting or inserting substances into the ingestible device 700.

The programming and charging dock 952 can include one or more electrical contacts for connecting to a programming and charging connector on the PCB 30. The power supply 160 may also be charged through the electrical contacts on the programming and charging dock 952. It will be understood that the number of electrical contacts can vary for different applications.

While the programming and charging dock 952 is shown in FIG. 17A, it should be understood that in some embodiments, there can be a charging dock for charging the ingestible device 700 and a separate programming component for programming the ingestible device. The programming component can be a radio transceiver or an infrared (IR) transceiver. For example, the IR transceiver may operate using modulated infrared light (e.g., between the wavelengths step 850 to 930 nm). The radio transceiver may operate using the Zigbee™ protocol or the ANT™ protocol depending on the particular type of the transceiver at the base station 950.

The USB connection port 962 can be connected to an external computing device via a USB cable. The external computing device may be a desktop computer, a laptop, a tablet and the like. A graphical user interface can be provided via the external computing device to enable interaction by an administrator with the ingestible device 700. The interaction can include various different operations, such as data transfer, control communication, and other similar functions.

The operational instructions may include data identifying a mode of operation (e.g., a type of task, such as collecting of samples and/or releasing of substances), operating parameters (e.g., sampling times, sampling intervals, error logging, and sampling locations), parameters for managing peripheral devices in the ingestible device 700 and operating parameters associated with performing a particular test or treatment procedure on the individual ingesting the ingestible device 700.

Figure 18A:
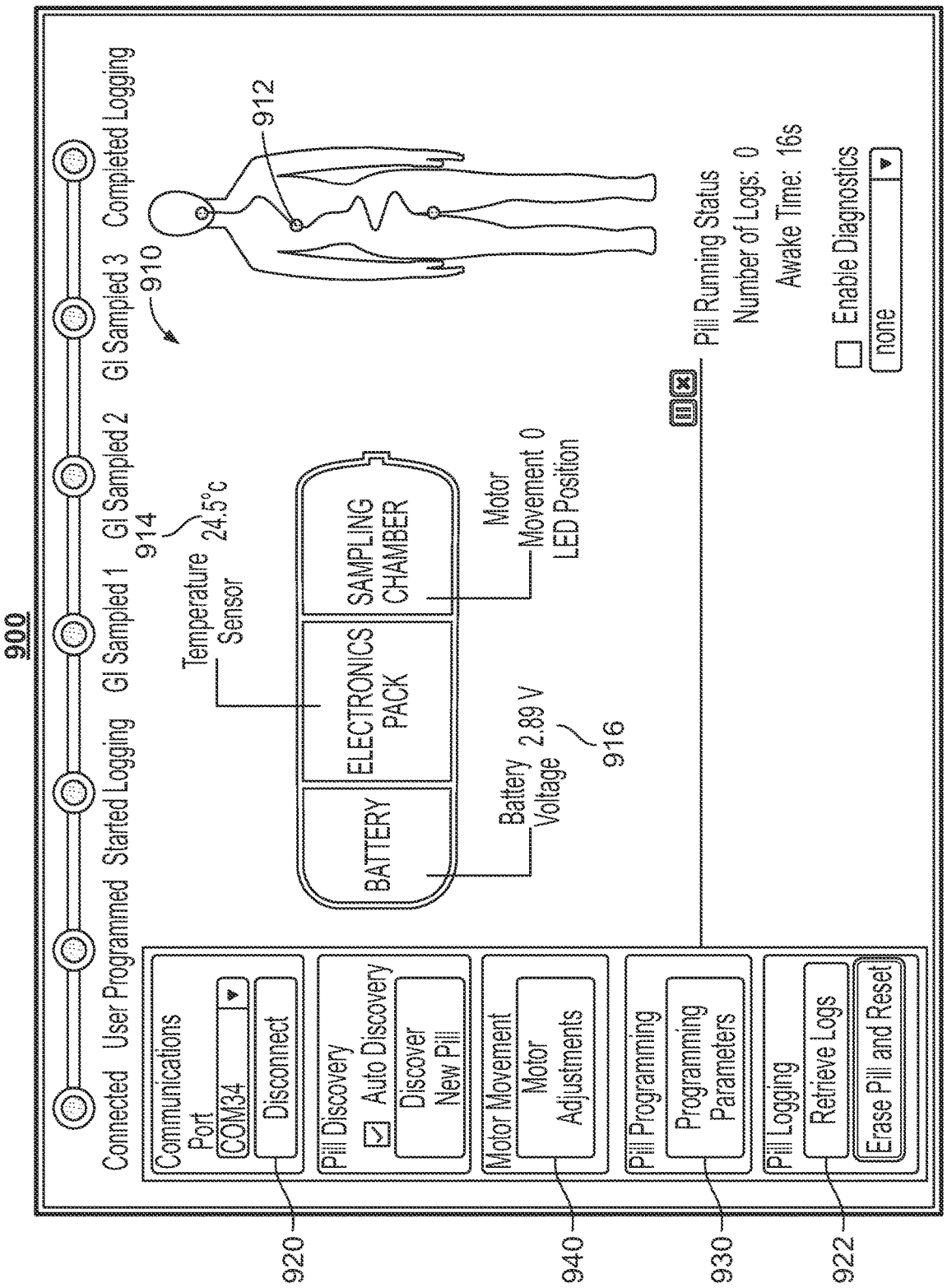
FIGS. 18A to 18C are screenshots of example embodiments of user interfaces for interacting with the ingestible devices described herein.
Figure 18B:
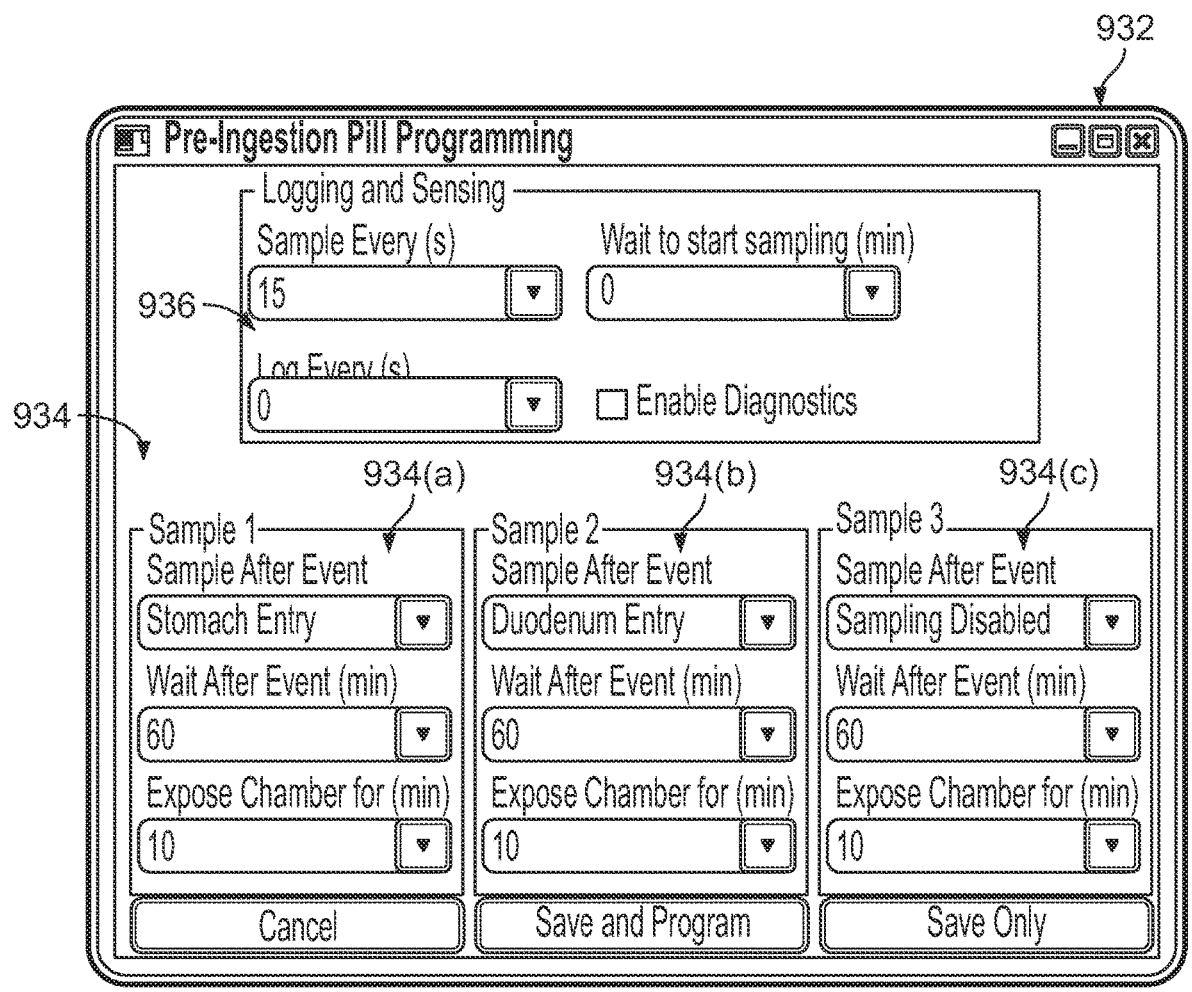
Figure 18C:
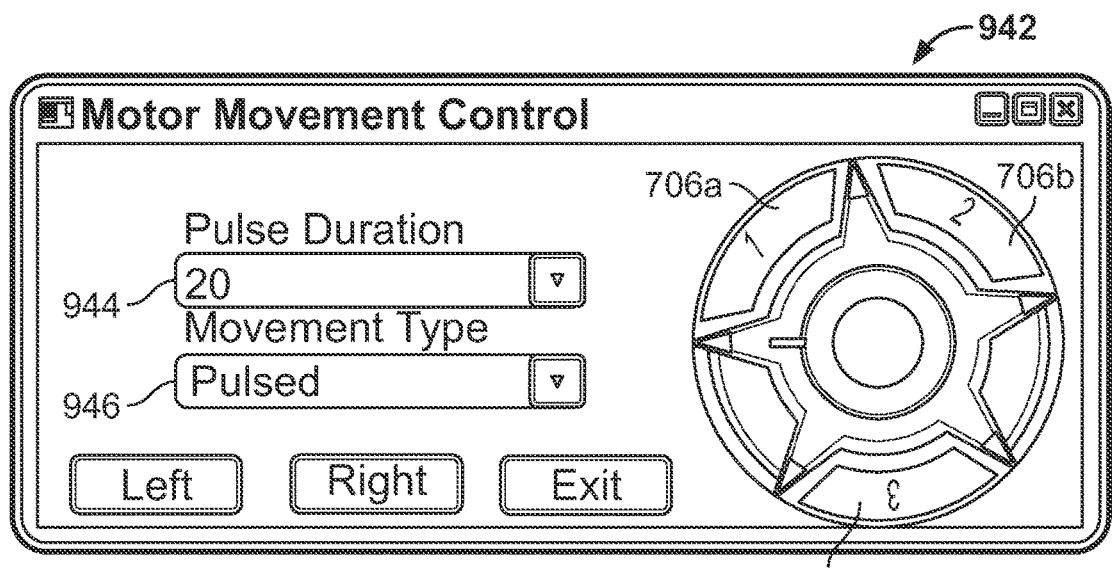

Referring now to FIGS. 18A to 18C, shown therein are screenshots of example embodiments of user interfaces 900, 932 and 942, respectively, for interacting with the ingestible device 700. It will be understood that analogous interfaces 900, 932 and 942 can be used for interacting with the ingestible devices 10, 300, 302, 304, 306, and 308, but different functionalities may be provided since the ingestible devices 10, 300, 302, 304, 306, and 308 do not include the storage sub-unit 702. For example, user interfaces for interacting with the ingestible devices 10, 300, 302, 304, 306, and 308 may include additional controls on the sensing sub-unit 130 and may unlikely include controls on the operation of the storage sub-unit 702.

FIG. 18A illustrates a main user interface 900 for configuring the ingestible device 700. As shown, the main user interface 900 includes a status component 910, a communication component 920, a data retrieval component 922, a programming definition component 930, and a motor control component 940.

The status component 910 can display information corresponding to an operational status of the ingestible device 700. For example, the operational status can include a status of a peripheral component on the ingestible device 700, a battery status 916 of the power supply 160, and/or a measurement 914 detected by the sensing sub-unit 130. A real-time in vivo location 912 may also be displayed.

Using the communication component 920, the administrator can select a communication port and initiate connection with the selected communication port. The administrator can also initiate retrieval of data from the ingestible device 700 (such as from the memory storage component 142) via the data retrieval component 922.

The programming definition component 930 can provide the programming interface 932 shown in FIG. 18B. The programming interface 932 can provide a sample acquisition control 934 for defining the sample acquisition algorithm and a data collection control 936 for defining the data collection algorithm. In the example shown in FIG. 18B, the sample acquisition control 934 includes three sample acquisition definitions 934(*a*), 934(*b*) and 934(*c*).

In the first sample acquisition definition 934(*a*), the ingestible device 700 is to collect a first sample 60 minutes after entry into the stomach is detected and the ingestible device 700 is to expose the chamber opening 708 for 10 minutes. In the second sample acquisition definition 934(*b*), the ingestible device 700 is to collect a second sample sixty minutes after entry into the small intestine 454 (duodenum) is detected and the ingestible device 700 is to expose the chamber opening 708 for ten minutes. In the third sample acquisition definition 934(*c*), it is shown that sampling has been disabled.

The data collection control 936 in this example indicates that reflectance data is to be collected immediately after the ingestible device 700 is ingested. The reflectance data may be logged every 15 seconds instead of constantly. This helps to reduce the amount of data that is collected and subsequently processed, which can also reduce the amount of energy that is needed from the battery 18 during operation.

Referring again to FIG. 18A, the motor control component 940 can provide the motor control interface 942 shown in FIG. 18C. The configuration of the chambers 706 can be illustrated in the motor control interface 942. In the illustrated example, the ingestible device 700 has three chambers, namely 706(*a*) to 706(*c*). Controls such as a movement type control 946 and a corresponding pulse duration control 944 may also be provided.

The microcontroller 710 can determine whether the operational instructions were successfully received. If so, the microcontroller 710 proceeds to program and initialize the ingestible device 700 according to the operational instructions at step 830. If not, the microcontroller 710 can request for the operational instructions to be resent.

Referring again to FIG. 16, at step 840, the ingestible device 700 is ingested by the individual.

After being ingested, the microcontroller 710 may place the ingestible device 700 in a low energy state (e.g., sleeping state) for a predefined wait period. During this time, the RF transceiver 722 may be intermittently turned on to poll for new instructions from the base station 950 (e.g., new instructions to override previously received instructions) and/or to transmit data to the base station 950. In some embodiments, being placed in a low energy state may comprise disabling or deactivating functions of the device for a predetermined period of time. For example, turning off individual sensors, encoders, analog to digital converters, entire sub-units (e.g., communication sub-unit 120 (FIG. 2A) or sensing sub-unit 130 (FIG. 2A)), and the like may preserve energy and avoid draining battery 18. In some embodiments the predefined wait period may be a predetermined period of time programmed into memory (e.g., memory storage component 142). For example, this may be set as part of a manufacturing process or as part of being programmed by a base station.

The predefined wait period may be provided as part of the operational instructions. For example, as indicated in the data collection control 936 of FIG. 18C, the microcontroller 710 may initialize operation of the ingestible device 700 immediately after the ingestible device 700 is ingested or after a certain amount of time has elapsed since the ingestible device 700 was ingested (e.g., so that the ingestible device 700 may have time to travel to a target location within the individual's body).

Once the predefined wait period has passed or, if there is no predefined wait period, the microcontroller 710 can initiate the sensing sub-unit 130 to detect reflectance from the external environment at step 850 to identify an in vivo location of the ingestible device 700 in accordance of the various methods described herein, such as method 500, for example.

At step 860, the microcontroller 710 determines whether the ingestible device 700 has arrived at the target location as identified in the operational instructions, such as from the sample acquisition control 934, for example. If the microcontroller 710 determines that the ingestible device 700 has not arrived at the target location, the microcontroller 710 returns to step 850.

In response to detecting that the ingestible device 700 has arrived at the target location, the microcontroller 710 may, at step 870, initialize operation of the ingestible device 700 according to the operational instructions.

For example, according to the sample acquisition definition 934(*a*), the ingestible device 700 collects a sample after entry into the stomach is detected. Therefore, the microcontroller 710 initiates collection of the first sample in response to the processing module indicating arrival in the stomach based on the reflectance data collected by the sensing sub-unit 130 in accordance to the methods described herein.

After the ingestible device 700 completes the task associated with the sample acquisition definition 934(*a*), the microcontroller 710 determines if all the operational instructions have been completed at step 880.

If the operational instructions have not been completed, the microcontroller 710 returns to step 850. For example, after the ingestible device 700 collects the first sample, the microcontroller 710 can proceed according to the operational instructions to collect the remaining samples. In respect of the second sample, the microcontroller 710 will initiate collection of the second sample in response to the processing module indicating arrival into the small intestine 454 (at step 860) in accordance with the sample acquisition definition 934(*b*). After the ingestible device 700 collects the second sample, the microcontroller 710 will return to step 850.

If the operational instructions have been completed, or the ingestible device is unable to continue its operation, the ingestible device 700 can be retrieved (at step 890). The microcontroller 710 may place all peripherals into a low-energy state to conserve power.

At retrieval, the ingestible device 700 may be subject to further analysis depending on its programmed task. For example, if the ingestible device 700 was programmed for collecting samples from the individual, the ingestible device 700 may be retrieved so that its collected samples are further analyzed. Generally, the samples in the ingestible device 700 may be extracted through manual pipetting or another suitable technique, which may be automated, as is known by those skilled in the art. The extracted samples can be analyzed using various techniques, such as but not limited to, biochemical analysis, for example.

It will be understood that the steps and descriptions of the flowcharts of this disclosure, including FIG. 16, are merely illustrative. Any of the steps and descriptions of the flowcharts, including FIG. 16, may be modified, omitted, rearranged, performed in alternate orders or in parallel, two or more of the steps may be combined, or any additional steps may be added, without departing from the scope of the present disclosure. For example, the ingestible device may be provided with default programming during the manufacturing process, or operating instructions may be encoded onto the device prior to activation. Furthermore, it should be noted that the steps and descriptions of FIG. 16 may be combined with any other system, device, or method described in this applications, and any of the ingestible devices or systems discussed in this application could be used to perform one or more of the steps in FIG. 16.

Figure 19:
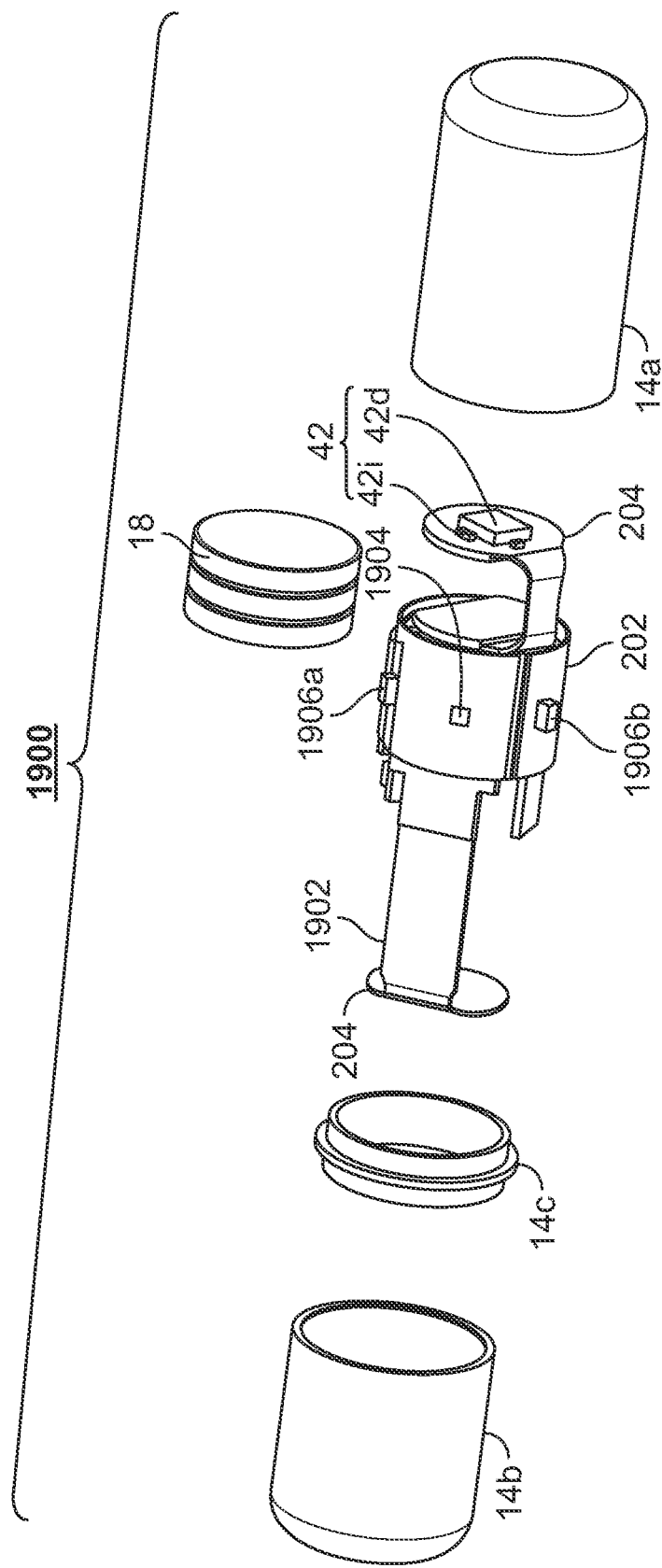
FIG. 19 is a view of another example embodiment of an ingestible device.

Referring now to FIG. 19, shown therein is a view of another example embodiment of an ingestible device 1900. Similar to the other ingestible devices (e.g., the ingestible devices 10, 300, 302, 304, 306, 700, and 2500), the ingestible device 1900 may be used for identifying a location within the gastrointestinal tract. The embodiment of the ingestible device 1900 is configured to autonomously determine whether it is located in the stomach, the small intestine, or the large intestine by utilizing sensors operating with different wavelengths of light. Additionally, the ingestible device 1900 can discern whether it is located within certain portions of the small intestine or large intestine, such as the duodenum, the jejunum, or the caecum.

The ingestible device 1900 may have the same general shape and construction of other ingestible devices discussed in this application (e.g., the ingestible devices 10, 300, 302, 304, 306, 700, and 2500), and it will be apparent that the disclosure related to the ingestible device 1900 may be combined with the disclosure related to any other ingestible device discussed in this application. For example, individual types of sensor configurations, materials, device housing, electronics, functionality, and detection algorithms described in relation to ingestible devices 10, 300, 302, 304, 306, 700, and 2500 may be used in some embodiments of the ingestible device 1900.

For example, the ingestible device 1900 may have a housing comprising a first end portion 14a, a second end portion 14b, and a connecting wall portion 14c, substantially similar to the ingestible device 10. The ingestible device 1900 may also utilize similar electrical systems or components as those discussed in relation to the ingestible device 10. The ingestible device 1900 employs a sensing array constructed from sensing sub-units, which includes the illuminators 1906a and 1906b, and the detector 1904. Although not all of them are shown on the figure, the ingestible device 1900 has three sets of radial illuminators and detectors located around the circumference of PCB 1902. In some embodiments, other numbers or configurations of sensing units may be used. The ingestible device 1900 may also have a top axial sensing sub-unit 42 at the axial end of PCB 1902. In general, PCB 1902 may be of similar make and construction as the other circuits discussed in this application, and utilize similar types of PCB segments (e.g., PCB segments 202 and 204) as other devices, with slight variations in illuminator and detector location. Although not visible, the ingestible device 1900 may also include a bottom axial sensing sub-unit located on the PCB segment 204 of PCB 1902 substantially opposite from the top axial sensing sub-unit.

FIG. 20 is a simplified top view and side view of an ingestible device, illustrating exemplary illuminator or detector locations. FIG. 20 may correspond to any number of ingestible devices, although for illustrative purposes we will refer to ingestible device 1900. The ingestible device 1900 as depicted features a sensor array, which is illustrated as comprising three radial detectors, 2002a, 2002b, and 2002c, along with three radial illuminators, 2004a, 2004b, and 2004c producing illumination. A similar configuration of detectors and illuminators was illustrated in FIG. 8A. Each radial illuminator and radial sensor is evenly spaced apart by approximately 60 degrees along the circumference of the ingestible device 1900. This positioning has been found to reduce internal reflections from the illuminators due to the housing of ingestible device 1900. However, in some embodiments, other arrangements of illuminators and detectors may be used to similar effect, such as the arrangements described by the ingestible devices 10, 300, 302, 304 and 306.

The radial illuminators 2004a, 2004b and 2004c are able to produce illumination at a plurality of different wavelengths, and in some embodiments of the ingestible device 1900 they may be implemented by using Red-Green-Blue Light-Emitting diode packages (RGB-LED). These types of RGB-LED packages are able to transmit red, blue, or green illumination. The radial illuminators 2004a, 2004b and 2004c of the ingestible device 1900 are each configured to transmit a particular wavelength simultaneously, sending illumination from the device in multiple different radial directions. For example, when the ingestible device 1900 is configured to transmit red light, all three radial illuminators may transmit red light simultaneously. Based on the environment surrounding the ingestible device 1900, a portion of the light may be reflected from the environment, and the resulting reflectance may be detected by the radial sensors 2002a, 2002b, and 2002c.

Similar to the sensors discussed in relation to the ingestible device 10, the radial sensors 2002a, 2002b, and 2002c may comprise photo-detectors that convert received light into an electrical signal. This signal may then be transmitted to an analog-to-digital converter (ADC), and the resulting digital signal may be manipulated by a processor or microcontroller (e.g., the microcontroller 110 located on PCB 30).

In some embodiments, the radial illuminators may each transmit different wavelengths of light, or they may be operated to transmit light at different times. For example, operating each of the radial illuminators independently may allow the device to detect features on the environment located at a particular side of the device.

FIG. 20 also depicts a pair of axial detectors 2006a and 2006b and a pair of axial illuminators 2008a and 2008b, which may be included on some variants of the ingestible device at substantially opposite ends of the device. These may be provided in similar fashion to the axial illuminator 42i and the axial detectors 42d described in connection with axial sensing sub-unit 42 of the ingestible device 10. The axial illuminators 2008a and 2008b are operated to transmit illumination in substantially opposite directions. In some embodiments, the axial illuminators 2008a and 2008b, are configured to transmit illumination in the infrared spectrum, but in some embodiments other wavelengths of light may be used, such as white light comprising a range of wavelengths covering the full visible spectrum.

Similar to the radial illuminators 2004a, 2004b and 2004c, the axial illuminators 2008a and 2008b may be configured to transmit light simultaneously, but in some embodiments they may be adapted to transmit light at different wavelengths, or to transmit light at different times or in an alternating fashion. Depending on the environment surrounding the ingestible device 1900, a portion of the illumination transmitted by the axial illuminators 2008a and 2008b may be detected by the various detectors located on the device, such as axial detectors 2006a and 2006b.

During transit of the ingestible device 1900 through the gastrointestinal tract, the ingestible device 1900 is configured to periodically take sets of sensor data. This is done by flashing different types of illumination in a predetermined sequence, and obtaining reflectance data for each flash. Every time it takes sensor data, the ingestible device 1900 may first transmit a signal to transmit red illumination from the illuminators 2004a, 2004b, and 2004c, and detect the resulting reflectance from the detectors 2002a, 2002b, 2002c. The amount of light detected in the reflectance is then quantified (e.g., by using the Analog-to-Digital converter 116), and stored in memory within the ingestible device. The ingestible device 1900 may then repeat this process with blue illumination, and green illumination. In some embodiments, the ingestible device may complete the data set by transmitting white or infrared illumination from axial illuminators (e.g., the axial illuminators 2008a and 2008b), detecting a resulting reflectance using axial or radial detectors (e.g., the axial detectors 2006a and 2006b), quantifying the data and storing it within the device memory. In some embodiments other types of temperature, pH, voltage, or other sensors may be provided to the ingestible device, and measured values of these sensor outputs may also be included in the sensor data set.

Figure 21:
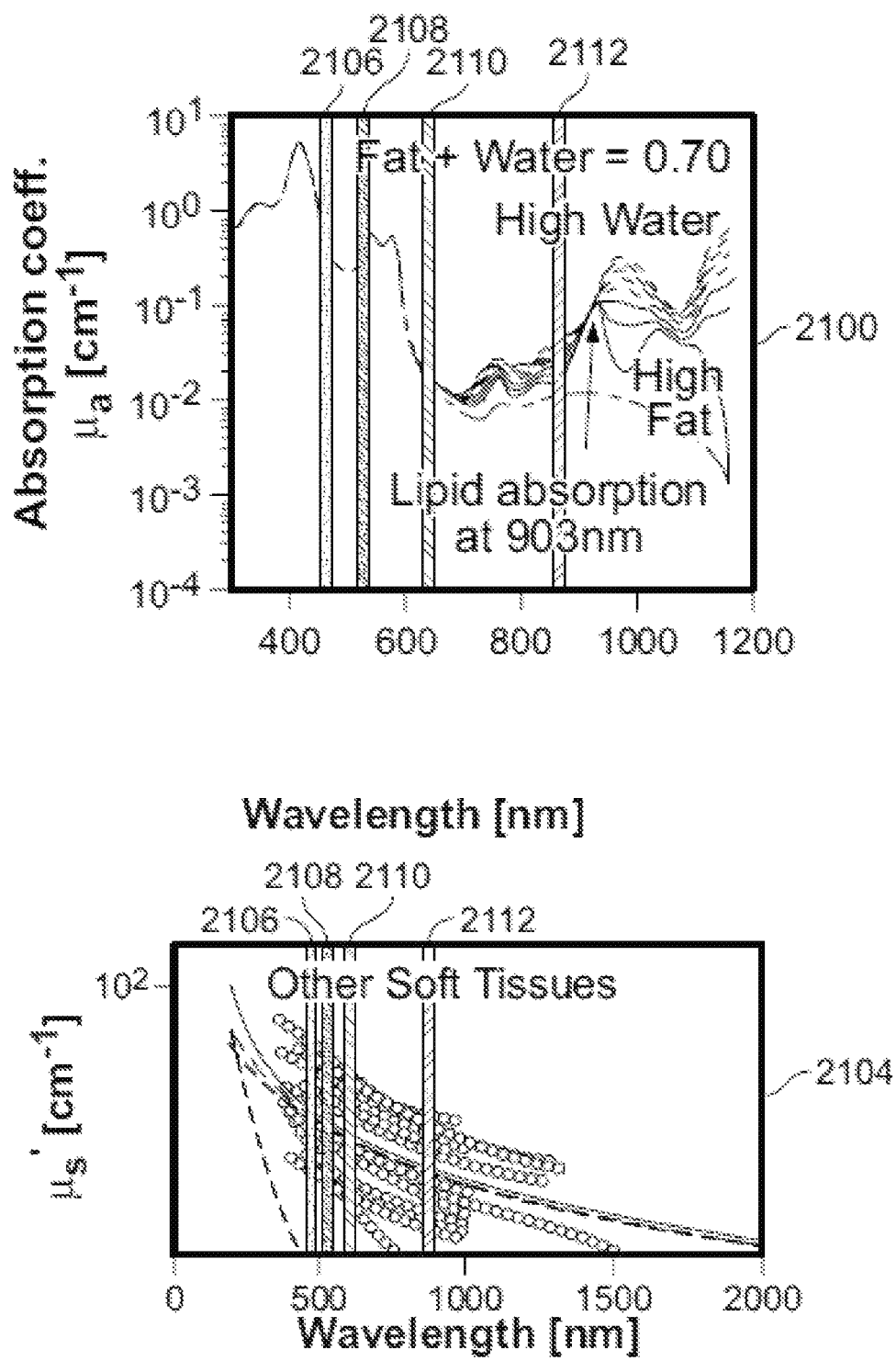
FIG. 21 describes how wavelengths of light used in some embodiments of the device interact with different environments.

FIG. 21 depicts the wavelengths of light used in some embodiments of the device, and how different wavelengths of light may interact with the environment surrounding the ingestible device, in accordance with some embodiments. As an ingestible device (e.g., the ingestible device 1900) transits through a gastrointestinal tract, each portion of the tract will have a different environment with different absorption and reflection properties for different wavelengths of light. For example, the stomach is typically characterized by a mixture of water, occasional particulates, loose tissue contact and naturally occurring mucus. By contrast, the small intestine is characterized by a more restrictive environment, with an ingestible device coming into close contact with smooth muscle, and the colon may feature opaque brown fecal matter. These different environments may cause variations in the absolute value of the illumination detected by the various sensors on an ingestible device, and may also cause diverging signals from different wavelengths of light.

By providing at least two wavelengths of light, the ingestible device 1900 is also able to reduce variations in detected reflectance due to patient-to-patient variation. In some aspects, by comparing response levels from multiple wavelengths of light together rather than looking for changes in absolute levels, the ingestible device 1900 may also account for the influence of manufacturing variability (e.g., casing opacity, photoreceptor response, mounting distances), and fluctuations in battery voltage levels.

It is known in the art that the absorption value for tissue high in fat and/or water diverges from regular tissue at wavelengths above approximately 600 nm and above (see, "Optical properties of biological tissues: a review," Phys., Med. Biol., ser. 27, vol. 2, pp. 149-52, November 2013). Additionally, a sharp decline in adsorption from ~575 to ~700 nm (i.e., light close to the red spectrum) is also observed (see, id.) By using illumination at two different wavelengths with substantially different absorption properties, as disclosed herein, it is possible to discern when an environment around the device consists of biological tissue. For example, the graph 2100 illustrates the different absorption properties of a blue illumination 2106, a green illumination 2108, a red illumination 2110, and an infrared illumination 2112, similar to the illumination used by some embodiments of the device.

When the environment around the ingestible device 1900 causes illumination to be primarily reflected from biological tissue, like in the enclosed space of the small intestine, the lower absorption value for the red illumination 2110 leads to a larger amount of red illumination 2110 being reflected by the biological tissue. As a result, higher levels of red reflectance are detected in the small intestine by the radial sensors 2002a, 2002b and 2002c of ingestible device 1900 as compared to blue or green reflectance.

It is also recognized in the art that generic soft tissue influences the scattering of different wavelengths of light. As illustrated on graph 2104, generic soft tissue has lower levels of scattering for increased wavelength. In turn, the scattering of light may also influence the number of photons returning to the photodetector. Additionally, the scattering characteristic of soft tissue is different than alternative reflective medium (e.g., gastric fluid within the stomach versus fecal matter in the large intestine). As described herein, the ingestible device 1900 that uses different wavelengths of light (e.g., the blue illumination 2106, the green illumination 2108, and the red illumination 2110) is able to take advantage of these different scattering characteristics as it determines a location within the gastrointestinal tract.

As a result of the above factors, in addition to other factors such as slightly differing colors in gastric fluid, bile located in the small intestine, and brown matter near the ileocecal junction leading to the large intestine, the ingestible device 1900 is able to gather data at a plurality of different wavelengths as it transits the gastrointestinal tract, and differentiate the different locations within the gastrointestinal tract reliably.

In some embodiments, the ingestible device 1900 may be implemented using a suitable RGB LED package for the radial illuminators. In some embodiments the radially mounted illuminators in the ingestible device 1900 may include the SML-LX0404SIUPGUSB RGB LED. In some embodiments an additional LED may be mounted along-side the RDB LED package to allow for additional wavelengths, and in some embodiments an IR LED or a polychromatic white LED may be mounted in the axial position (e.g., to implement the axial illuminators 2008a or 2008b) of the ingestible device 1900.

Figure 22:
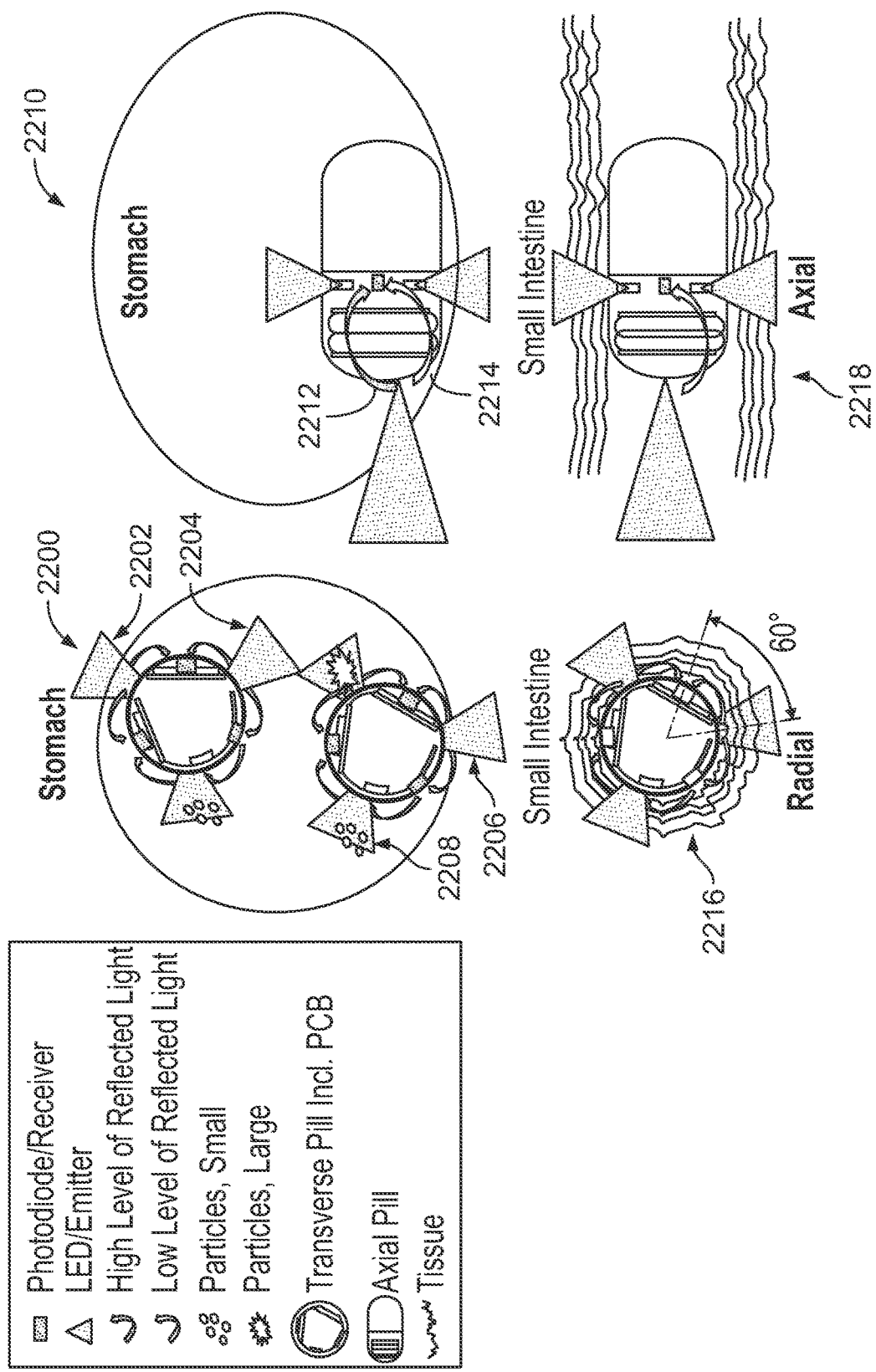
FIG. 22 describes the reflection properties of different regions of the gastrointestinal tract as they relate to the device.

FIG. 22 illustrates the reflection properties of different regions of the gastrointestinal tract as they relate to the device. As the ingestible device (e.g., the ingestible device 1900) transits through the gastrointestinal tract, different environments affect the overall amount of reflectance measured by the various radial sensors under different circumstances. These changes in absolute levels of detected light do not take into account additional variations between different wavelengths of light. Although FIG. 22 is described using an embodiment of the ingestible device 1900 equipped with radial and axial illuminators, the discussion applies to any ingestible device described in this application (e.g., the ingestible devices 10, 300, 302, 304, 306, and 700) which may have a different number or different orientation of illuminators and detectors. Additionally, in some embodiments an ingestible device with only radial sensors may be used to implement some of the localization techniques described herein.

For example, image 2200 shows a longitudinal view of an ingestible device (e.g., the ingestible device 1900) in a stomach, and shows how the amount of light detected by the various radial sensors on the ingestible device 1900 from the various radial illuminators changes under different conditions. The illumination 2202 being transmitted from a slight distance away from the stomach wall is reflected off the wall, into the acceptance angle of the adjacent radial detectors. This results in a strong amount of overall reflectance being detected. By comparison, the illumination 2204 pointing away from any kind of tissue or particulate results in minimal light reflected back into the detectors. The illumination 2206 demonstrates that when the ingestible device 1900 is too close to a surrounding wall or tissue, very little light is reflected in a manner that will be detected by the radial detectors. Finally, the illumination 2208 demonstrates that the presence of particulates may allow the light to reflect and scatter, causing a larger signal to be received by the radial detectors. These different types of behaviors lead to differing absolute levels of light being detected by the ingestible device 1900 while it is in the stomach. As discussed in relation to FIGS. 8-13, this also leads to a large variance in the amount of light that will be detected by the ingestible device 1900.

As another example, image 2210 shows a side view of an ingestible device (e.g., the ingestible device 1900) in a stomach, and shows the amount of light detected by the various radial sensors on the ingestible device 1900 from an axial illumination. The axial illumination is reflected off a nearby stomach wall, and the resulting reflectance scatters in multiple directions. The reflectance 2212 directed into the fluid of the stomach may be easily detected by the radial sensors. By comparison, the reflectance 2214 directed into the tissue on the side of the stomach is not detected easily by the radial sensors.

As another example, image 2216 shows a longitudinal view of an ingestible device (e.g., the ingestible device 1900) in a small intestine, and shows how the amount of light is detected by the various radial sensors on the ingestible device 1900 from the various radial illuminators under different conditions. The close confined space of the small intestine may prevent significant amounts of radial illumination from being reflected back into the detectors. Similar to illumination 2206, because the ingestible device 1900 is too close to the walls of the small intestine, very little of the illumination is able to be reflected directly into the radial detectors, resulting in a lower overall level of illumination being detected. However, this effect can be mitigated when red light is used, due to the wavelength absorption properties of the small intestine lining.

As another example, image 2218 shows a side view of an ingestible device (e.g., the ingestible device 1900) in a small intestine, and shows how the environment alters the amount of light detected by the various radial sensors on the ingestible device 1900 from the axial illuminators. Generally the small confined space of the small intestine will cause the ingestible device 1900 to be oriented along the longitudinal axis of the capsule-shaped ingestible device. Axial illumination transmitted from the end of the device has minimal tissue or particulates to be reflected from, and in combination with the enclosed space, very little axial illumination is able to be detected by the radial sensors. As a result, minimal light from the axial illuminator is able to be detected by the radial sensors of the ingestible device 1900 in the small intestine. By contrast, in the environment of the stomach or the large intestine, the axial illumination will result in a greater reflectance being detected. In some embodiments, the axial illuminator of the ingestible device 1900 may be configured to transmit wavelengths of light that can be detected by the radial detectors, such as white light. In some embodiments, the radial detectors and axial illuminator may be designed so that light transmitted by the axial illuminator is unable to be easily detected by the radial illuminator. For example, the axial illuminator may be configured to transmit light in the infrared wavelength, and the radial detectors may be configured to receive light in the visible spectrum.

Figure 23:
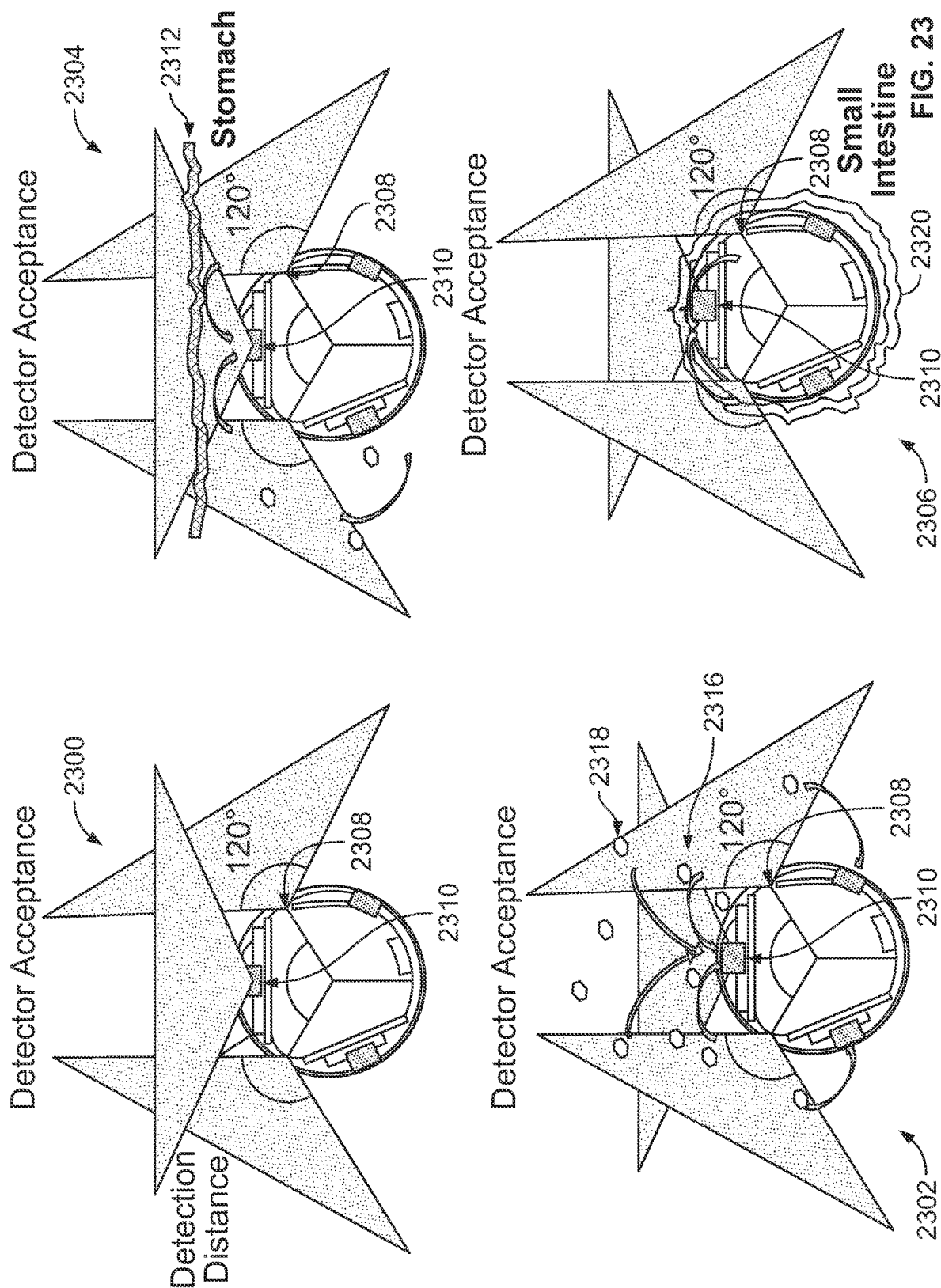
FIG. 23 describes how different types of reflected light may be detected in different regions of the gastrointestinal tract.

FIG. 23 illustrates the detecting light reflected from different regions of the gastrointestinal tract as they relate to an ingestible device (e.g., the ingestible device 1900). Particularly, FIG. 23 illustrates how radial illumination may be reflected by the environment, and received by the various radial detectors. This description may be combined with or supplemented by the description in conjunction with FIGS. 8A-8C and FIG. 22, which describe similar subject matter. In some aspects, the radial illuminators on an ingestible device (e.g., the radial illuminators 2002a, 2002b, and 2002c (FIG. 20) of the ingestible device 1900 (FIG. 19)) transmit the illumination 2308 away from the housing of the device in approximately a 120-degree arc. In some embodiments, this arc may be smaller or larger depending on the materials and components used to construct the ingestible device. Similarly, a radial detector (e.g., radial detectors 2002a, 2002b and 2002c (FIG. 20)) will have a detector acceptance range 2310, and light travelling towards a radial detector of the ingestible device (e.g., the radial detectors 2002a, 2002b, and 2002c (FIG. 20)) within the detector acceptance range 2310 will be able to be detected by the radial detectors. In some aspects, the acceptance range is approximately a 120-degree arc, but it will be understood by one skilled in the art that this depends on a number of factors, including the configuration of the internal components of the ingestible device, and optical considerations such as the index of refraction of the device housing, the index of refraction of the immediate surrounding environment, and the resulting acceptance angle of the interface between the device housing and the surrounding environment.

An open environment 2300 in the absence of any type of reflective surface or particulates is unable to deflect light transmitted as part of illumination 2308. As a result, the light travels in a relatively straight path away from the device, and essentially none of the illumination 2308 will be detected by the radial detector.

An environment with particulates 2302 may result in illumination being received by a radial detector after being reflected off small particulates. The presence of small irregular particulates around the device may cause illumination to be reflected in a plurality of directions, causing a portion of the illumination to be redirected into the acceptance angle of the radial detector. Based on the distance between the radial illuminator and the particulates, a varying amount of illumination may be detected by the radial detectors. For example, the particulate 2316 is within the arc of the illumination 2308, and is relatively close to the source of the illumination 2308. As a result, a portion of the light contained in the illumination 2308 will be reflected off the particulate 2316, and redirected into the radial detector acceptance range 2310. By comparison, the particulate 2318 is still within the arc of the illumination 2308, but it is further away from the source of the illumination 2308. As such, a smaller amount of light will be reflected off the particulate 2318, diverted into the detector acceptance range 2310, and detected by the radial detector. For example, this may be as a result of both decreased optical intensity as light travels further away from the illumination source, and also due to possible shadowing caused by other particulates (e.g., the particulate 2316 in the path between the illumination source and the particulate 2318) or cloudiness in the fluid or other matter surrounding the device.

An environment near a stomach wall 2304 demonstrates how illumination may be received by a radial detector after being reflected off stomach tissue a slight distance away from the device. Although this is described in relation to stomach tissue, this may apply to any type of organ tissue a sufficient distance away from the device. At a sufficient distance away from the stomach, a substantial amount of the illumination 2308 will be reflected off the stomach lining 2312, and diverted into the detector acceptance range 2310. As a result, a large portion of the illumination 2308 is able to be detected by the radial detector. It will be apparent that in an actual stomach, the position of an ingestible device will move and change, leading to large variations in the amount of light detected, as well as a larger amount of light being received on average. In some embodiments (e.g., the ingestible devices 10, 300, 302, 304, 306, 700, 1900) both the large variability in the absolute amount of light detected, or the average amount of light detected, may be used to determine that the ingestible device is located in the stomach.

A small intestine environment 2306 may result in small amounts of illumination being received by a radial detector. Generally, the enclosed space of the small intestine lining 2320 will prevent the illumination 2308 from reaching the radial detector. The illumination 2308 is reflected by the small intestine lining 2320, but because of the positioning, very little of the light in the illumination 2308 is able to be directly reflected into the radial detector acceptance range 2310. A small amount of light will continue to reflect back and forth between the small intestine lining 2320 and the housing of the ingestible device, and will finally reach the appropriate acceptance range 2310 where it may be detected, but generally this leads to a very small amount of overall light being detected. However, due to the reddish color of the small intestine, red illumination may be better able to reflect multiple times and reach the radial detector as compared to green or blue light.

Figure 24:
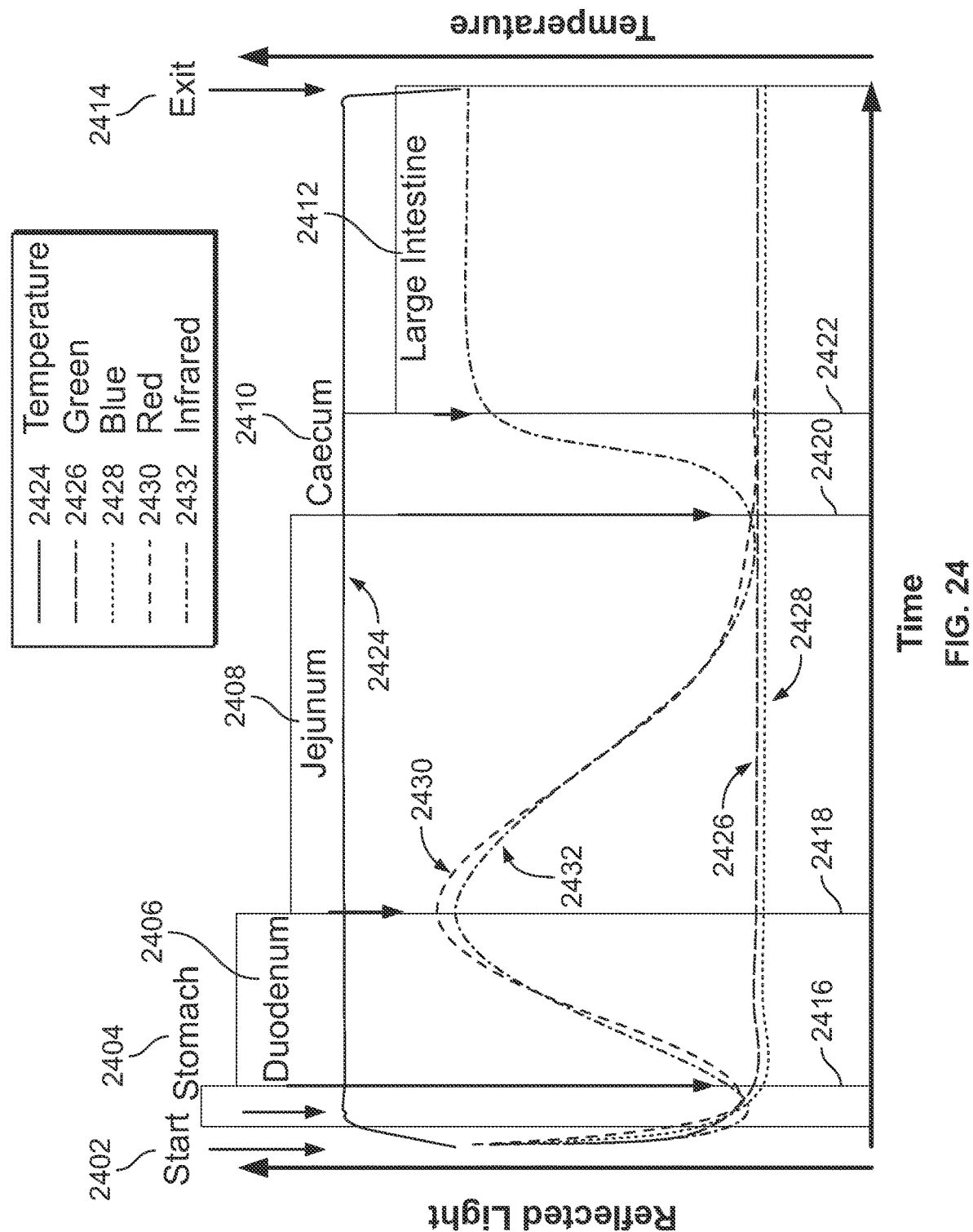
FIG. 24 describes reflectances measured in different regions of the gastrointestinal tract, and a process for localizing the device.

FIG. 24 illustrates typical reflectances measured in different regions of the gastrointestinal tract. The ingestible device 1900 primarily functions by keeping track of a current region of the gastrointestinal tract surrounding the device, and by monitoring the environment around the device to determine changes from one region to another. In some embodiments, the ingestible device 1900 may autonomously identify a location of the device within the gastrointestinal tract of a body by monitoring the changes from one region to another. In some embodiments, the ingestible device 1900 functions as a state machine, wherein the state tracks the current portion of the gastrointestinal tract where the ingestible device 1900 is located. The ingestible device 1900 may distinguish between various locations including a starting point outside the body 2402, a stomach 2404, a duodenum 2406, a jejunum 2408, a caecum 2410, a large intestine 2412, and an exit point outside the body 2414. In some embodiments the ingestible device 1900 may distinguish only between a stomach 2404, a small intestine, (e.g., a small intestine which may include the duodenum 2406 and the jejunum 2408), and a large intestine (e.g., a large intestine which may include the caecum 241, and the large intestine 2412). In some embodiments the ingestible device 1900 may distinguish between a subset of the above mentioned locations, and/or a combination of the above locations and other locations, such as a mouth, an ileum, or a rectum.

In some embodiments the ingestible device 1900 may transmit illumination at a first wavelength towards an environment external to a housing of the ingestible device, detect the resulting reflectance, and store a reflectance value in a data set based on the first reflectance. For example, the ingestible device may transmit illumination at a red wavelength, detect a red reflectance, and store a reflectance value in a red data set that indicates how much light was measured in the red reflectance. The ingestible device 1900 may repeat this process for a number of other types of illumination at other wavelengths, such as blue, green, or infrared wavelengths. The ingestible device 1900 may keep track of reflectance data gathered from reflectance sensors (i.e., radial detectors) in each of the red, green, blue and IR spectra.

This data may then be used by an onboard microprocessor to perform a localization algorithm that identifies a pyloric transition 2416 from stomach 2404 to the duodenum portion of the small intestine 2406; a treitz transition 2418 from the duodenum 2406 to the jejunum 2408; an ileocaecal transition 2420 from the ileum (i.e., the area located at the end of the jejunum 2408) to the caecum 2410; and a caecal transition 2422 from the caecum 2410 to the rest of the large intestine 2412. This can be accomplished by using a plurality of different wavelengths of light, measuring the different amounts of light reflected by the environment around the device, and determining the location of the device in view of the different optical absorption properties of the different regions of the gastrointestinal tract. The ingestible device 1900 may gather this data at periodic intervals, and in some embodiments these may be spaced one second to 10 minutes apart. For example, the ingestible device 1900 may take new data samples a few times a minute until it detects a location in the small intestine, and then it may take new data samples every few minutes. While not taking samples, the ingestible device 1900 may enter a dormant sleeping or standby state to preserve energy reserves.

In some embodiments, the ingestible device 1900 may detect the various locations and transitions identified in FIG. 24 by using an appropriate sensor array (e.g., as depicted in FIG. 20) made up of a plurality of radial and axial light-emitting diode (LED)/phototransistor pairs that function as reflectance sensors. In some embodiments, the ingestible device 1900 may also include a temperature sensor and internal real time clock (RTC) oscillator for keeping time. It will be understood to one skilled in the electrical arts that a temperature sensor and an oscillator are easily acquired components that can be integrated into the circuitry of a PCBA (e.g., PCBA 202) using known techniques.

The ingestible device 1900 described in relation to FIG. 24 has a set of radial illuminators (e.g., the illuminators 2004a, 2004b and 2004c (FIG. 20)) capable of transmitting light in the red, green, and blue spectra, as well as an axial illuminator (e.g., the axial illuminator 2008a (FIG. 20)) capable of transmitting light in the infrared spectrum. The ingestible device 1900 may then have a set of detectors (e.g., the radial detectors 2002a, 2002b, and 2002c (FIG. 20)) capable of measuring the reflectance of these different types of light. However, in some embodiments, particular transitions may be detected using as few as two different wavelengths of light, and the hardware used to implement the illuminators and detectors may be changed appropriately. For example, identifying a pyloric transition, a trietz transition, and a caecal transition may be accomplished by comparing a red reflectance to either a green or blue reflectance.

As the ingestible device 1900 transits through the different regions of the gastrointestinal tract depicted in FIG. 24, the ingestible device 1900 may gather sensor data over time. The device software stored in memory (e.g., stored on memory sub-unit 140 (FIG. 2A)) and executed by a processor or microcontroller (e.g., microcontroller 110 (FIG. 2A)) keeps track of all measurements and events. An onboard algorithm, further described below, is then applied to determine the ingestible device 1900 position by monitoring the various locations and transitions. The algorithm has been designed to move through states that represent the anatomical location of the ingestible device 1900 (e.g., the start 2402, the stomach 2404, the duodenum 2406, the jejunum 2408, the caecum 2410, the large intestine 2412, and the exit 2414) by using sub-algorithms to identify anatomical transitions (e.g., entry to the stomach, a pyloric transition 2416, a treitz transition 2418, a ileocaecal transition 2420, a caecal transition 2422, and an exit from the body, 2414. In some embodiments, the ingestible device 1900 will have a state which corresponds to a known or estimated location of the device, and based on the current state, the ingestible device 1900 may run an algorithm to search for the next state transition. For example, when the ingestible device 1900 knows it is in the stomach (e.g., the stomach 2404), it will identify the current state as the "STOMACH" state. The ingestible device 1900 will then perform an algorithm to identify a pyloric transition (e.g., the pyloric transition 2416). Once a pyloric transition is identified, the ingestible device 1900 may determine that it is now located in the duodenum portion of the small intestine (e.g., the duodenum 2406), and the state will switch to the "DUODENUM". In some embodiments the ingestible device may determine a state by estimating or inferring the current location of the device. For example, in some embodiments the ingestible device 1900 may assume that in the absence of a detected state transition, the location of the device has remained the same, and maintain the same state. As another example, when the device is first activated, it may assume that it is at an initial starting state external to the body (e.g., the start 2402).

FIG. 24 also shows a plot of the detected reflectance due to illumination at different wavelengths, and a temperature measured by the device, over time. Temperature 2424 changes to a temperature near body temperature soon after the ingestible device 1900 enters the body, and changes back to a different ambient temperature once the ingestible device 1900 exits the body. Detected green reflectance 2426 and blue reflectance 2428 behave similarly, having a low response throughout the duodenum 2406, jejunum 2408, caecum 2410, and large intestine 2412. For the purposes of the algorithms described in connection with the ingestible device 1900, the detected green reflectance 2426 and the detected blue reflectance 2428 are largely interchangeable, although for simplicity we may refer simply to the detected green reflectance 2426.

The detected red reflectance 2430 has a more varied response over time than the detected green and blue reflectances 2426, 2428. The detected red reflectance 2430 is lower in the stomach 2404, and rises during the pyloric transition 2416 as the ingestible device 1900 enters the duodenum portion of the small intestine 2406. The detected red reflectance 2430 rises as it progresses through the duodenum, reaching its apex near the treitz transition 2418 as the ingestible device 1900 nears the jejunum 2408. While the ingestible device 1900 transits the jejunum 2408 and the caecum 2410, the detected red reflectance 2430 reduces, reaching a local minimum near the caecal transition 2422.

The detected infrared reflectance 2432 depicted in FIG. 24 is a result of an axial illuminator and axial detector, as opposed to the other detected reflectances 2426, 2428 and 2430, which are typically measured by radial detectors. The detected infrared reflectance 2432 has a similar behavior to the detected red reflectance 2430 during transit through the stomach, duodenum and jejunum. However, the detected infrared reflectance 2432 reaches a low point near the ileocaecal transition 2420, and the detected infrared reflectance increases in the caecum 2410 before settling to a large value during transit through the large intestine 2412.

In some embodiments the ingestible device 1900 may determine when a state transition has occurred by comparing a reflectance (e.g., the red reflectance 2430) to another reflectance (e.g., the green and blue reflectances 2426, 2428). For example, a pyloric transition (e.g., the pyloric transition 2416) may be detected when the red or the infrared reflectances 2430, 2432 have diverged from the green or the blue reflectances 2426, 2428, in a statistically significant manner. In some embodiments, determining whether two reflectances (e.g., the red reflectance 2430 and the green reflectance 2426) have diverged in a statistically significant manner may involve determining if a sample mean of the red reflectance data and a sample mean of the green reflectance data are statistically different using an appropriate statistical technique. For example, this may be done by performing a t-test and determining if the two sample means are statistically different with a significance level of $p<0.05$. In some embodiments, this test may be performed on the most recent values recorded in the reflectance data sets. In some embodiments, the data sets may be cleaned (e.g., by detecting and removing outliers) before being used to make a statistical comparison. It will be understood to one skilled in the art that various test statistics and statistical techniques may be used to determine statistical significance. The techniques may include, but are not limited to, comparisons of means, standard deviations and variances, t-tests, f-tests, data cleaning methods, machine learning techniques, feature extraction, and the like, or any combination thereof.

It will also be understood to one skilled in the art that identifying relationships between one or more reflectances, such as determining when two reflectances converge or diverge, or when individual reflectances reach local maximum or minimum values, can be done using various known statistical techniques or ad-hoc techniques. For example, one ad-hoc method may determine a statistically significant divergence by evaluating when a simple moving average of the red reflectances 2430 is twice the simple moving average of the green reflectances 2426. As another example, in some embodiments the ingestible device 1900 may integrate the difference between weighted or simple moving averages, and determine when the integral is larger than a threshold value to determine that two reflectances have diverged in a statistically significant way. The threshold value itself may be a multiple of one of the simple moving averages, such as ten times the simple moving average of the last 50 data points in the green reflectance data set 2426. In some embodiments, the ingestible device 1900 may determine statistical significance when the measured red reflectance 2430 is larger than a measured green reflectance 2426, for example, 10-times larger. In some embodiments, the ingestible device may increment a counter when the measured first reflectance (e.g., the red reflectance 2430) is larger than a measured second reflectance (e.g., the green reflectance 2426). In some embodiments, the counter may be incremented when the mean of the first data set (e.g., the red reflectance 2430) less a multiple of the standard deviation of the first data set is greater than a mean of the second data set (e.g., the green reflectance 2430) plus a multiple of the standard deviation of the second data set. For example, in some embodiments a duodenum detection algorithm may increment a counter when the mean of the red reflectance 2430 less the standard deviation of the red reflectance 2430 is greater than the mean of the green reflectance 2430 less the standard deviation of the green reflectance 2430, and the pyloric transition 2416 is detected when the counter is greater than 7000. In some embodiments a caecum detection algorithm may increment a counter when the mean of the infrared reflectance 2432 less the standard deviation of the infrared reflectance 2432 is greater than the mean of the green reflectance 2430 less the standard deviation of the green reflectance 2430, and the ileocaecal transition 2420 is detected when the counter is greater than 1000. In some embodiments, the ingestible device 1900 may reset counters periodically. In some embodiments, because the counter is unit-less and the number of counts may depend on frequency with which the device takes samples, the ingestible device 1900 may detect transitions when the counter reaches a different threshold. For example, in some embodiments the ingestible device 1900 may take new data at a relatively fast speed, and the duodenum detection algorithm may detect a state transition when the counter is greater than 700.

As the ingestible device 1900 transits through the portions of the gastrointestinal tract, it utilizes a localization algorithm to determine its location. In some aspects, this is done by selecting among the various state of the device that corresponds to one of the gross anatomical structures of the gastrointestinal tract that are stored in the device. The states tracked by the ingestible device 1900 and the sub-algorithm implemented to track state transitions are described according to some embodiments below.

GI State: START_EXTERNAL. This state is entered when the device is programmed and begins logging operations. For example, at the start 2402, before being administered to a patient, the ingestible device 1900 may be set to the START_EXTERNAL state. In some embodiments the ingestible device 1900 may include a communication sub-unit (e.g., the communication sub-unit 120 (FIG. 2A) described in connection with the embodiment of the ingestible device 10 (FIG. 1)), and can communicate with a base station (e.g., base station 950 (FIGS. 17A to 17C)). When the ingestible device 1900 is connected with the base station, it may be set to the START_EXTERNAL state by default. In some embodiments the START_EXTERNAL state may also be the default state whenever ingestible device 1900 is first activated.

GI State: STOMACH. This state is entered once the ingestible device 1900 determines it has entered the stomach 2404. In some embodiments, the ingestible device 1900 may include a temperature sensor for measuring the temperature of the environment around the device. The ingestible device 1900 may determine that it has transitioned into the stomach once the measured temperature is close to the internal body temperature of the patient. For example, for a typical human patient the internal body temperature is close to 37 degrees Celsius, the ingestible device 1900 may then determine that it has entered the stomach when the temperature sensor measures a temperature within a range of 30-40 degrees. In some embodiments, the temperature range may be manually set by programming the ingestible device 1900 using a base station. In some embodiments the ingestible device 1900 may be adapted to also use the radial and axial detectors (e.g., the detectors 2002a, 2002b, 2002c, 2006a and 2006b) to determine a change in the level of ambient light in the environment. After measuring a reduction in the light in the surrounding environment, a reduction which would be typical of an ingestible device being swallowed, the ingestible device 1900 may determine that it has entered the body and automatically determine that it has transitioned from the START_EXTERNAL to the STOMACH state. This may be particularly useful when the ingestible device 1900 does not include a temperature sensor, or when the temperature of the ambient environment is similar to the internal body temperature.

Figure 33:
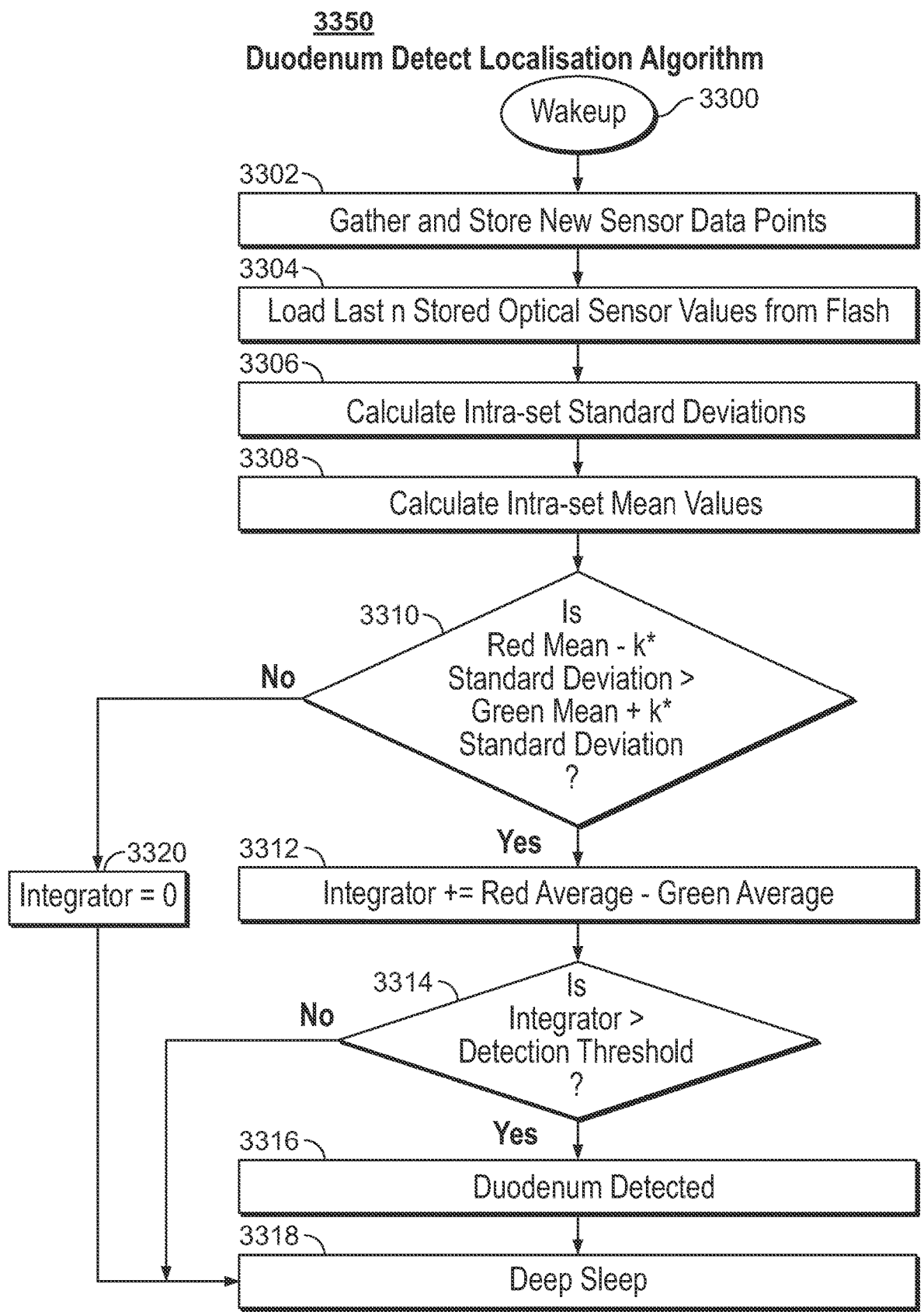
FIG. 33 is a flowchart describing a duodenum detection algorithm used in some embodiments of the device.

GI State: DUODENUM. This state is entered once the ingestible device 1900 detects a pyloric transition 2416 from the stomach 2404 to the duodenum 2406. This may be accomplished by using a duodenum detection sub-algorithm, which operates automatically whenever the ingestible device 1900 is in the STOMACH state. In some aspects, the duodenum detection sub-algorithm may determine when a red or infrared reflectance 2430, 2432 diverges from a green or a blue reflectance 2426, 2428 in a statistically significant way. It will be understood to one skilled in the art that various statistical, filtering, or ad-hoc techniques can be used to identify this point. For example, this may be calculated using various known statistical techniques or ad-hoc techniques, such as performing a t-test using, for example the last 30 data points, or by determining when a red or infrared reflectance 2430, 2432 is, for example, twice the value of a green or a blue reflectance 2426, 2428. In some aspects, the duodenum detection sub-algorithm compares the difference between the detected red spectrum 2430 versus that of the detected green or blue spectrum, and marks a transition when the difference is larger than a threshold value. In some aspects, the algorithm uses the mean of multiple data points in the detected red reflectance data and the detected green reflectance data, takes the difference between the two means, and compares the difference to a threshold value. For example, the ingestible device 1900 may be configured to take new data samples every 15 seconds, and to take a simple moving average of the most recent 40 samples to determine a mean red reflectance and a mean green reflectance. In some embodiments, the duodenum detection algorithm may involve taking the integral of the difference between the mean of the red reflectance and the mean of the green reflectance. For example, in some aspects, taking the mean of the difference between the two simple moving averages may assist the ingestible device 1900 in avoiding false transitions, or assist in detecting a transition sooner. Other aspects of the duodenum detection algorithm are illustrated in FIG. 33. Although the above discussion uses detected red reflectance 2430 and detected green reflectance 2426, in some embodiments a similar algorithm may be performed using either detected infrared reflectance 2432 in place of detected red reflectance 2430, or by using detected blue reflectance 2428 in place of the detected green reflectance 2426.

GI State: JEJUNUM. This state is entered once a treitz transition 2418 between the duodenum 2406 and the jejunum 2408 is detected. In some aspects, this may be detected by the use of a jejunum detection sub-algorithm, which may be performed automatically once the ingestible device 1900 is in the DUODENUM state. In some aspects, the jejunum detection sub-algorithm may determine when a red or infrared reflectance 2430, 2432 either reaches a local maximum, or when the difference between a red or infrared reflectance 2430, 2432 and a green or a blue reflectance 2426, 2428 is constant in a statistically significant way (e.g., as a result of the ref reflectance 2430 reaching a local maxima). It will be understood to one skilled in the art that various statistical, filtering, or ad-hoc techniques can be used to identify this point. For example, this may be calculated by finding when the derivative or finite difference of the red or infrared reflectance 2430, 2432 reaches zero, or changes signs. In some aspects, the jejunum detection sub-algorithm identifies the point of maximal reflected light in the red spectrum versus that of the green and blue spectrum. In some aspects, the jejunum detection sub-algorithm may compare the detected red reflectance value to a threshold, and in some aspects, the algorithm evaluates the difference between a simple moving average of the detected red reflectance 2430 and a simple moving average of the detected green reflectance 2426 or detected blue reflectance 2428. In some embodiments, the detected infrared reflectance 2432 may be used instead of the detected red reflectance 2430.

GI State: CAECUM. This state is entered once the ingestible device 1900 detects an ileocaecal transition 2420 from the ileum (i.e., the portion of the gastrointestinal tract at the end of the jejunum 2408) to the caecum 2410. In some aspects, this may be detected by using a caecum detection sub-algorithm. In some aspects, the caecum detection sub-algorithm may determine when the infrared reflectance 2430 reaches a local minimum, or when the infrared reflectance 2430, 2432 converges with the green or a blue reflectance 2426, 2428 in a statistically significant way (e.g., as a result of the ref reflectance 2430 reaching a local maxima). It will be understood to one skilled in the art that various statistical, filtering, or ad-hoc techniques can be used to identify this point. For example, in some embodiments this may be calculated by finding when the derivative or finite difference of the infrared reflectance 2432 reaches zero, or finding when a simple moving average of the difference between the infrared reflectance 2430 and the green reflectance 2426 is statistically equal to zero. This sub-algorithm may be performed automatically when the ingestible device 1900 is in the JEJUNUM state. In some aspects the caecum detection sub-algorithm may compare the detected red reflectance 2430 or the detected infrared reflectance 2432 and the detected green reflectance 2326 or the detected blue reflectance 2328 to find a point where the difference is less than a first threshold value. Similar to our discussion of the other sub-algorithms, in some aspects this algorithm may use a simple moving average as opposed to raw data points. In some aspects, a caecum detection sub-algorithm may integrate the difference between mean reflected light in the infrared spectrum versus that of the green spectrum and tests for a difference less than a detection threshold. In some embodiments, other techniques may be incorporated into the caecum detection sub-algorithm, such as those illustrated in FIG. 32.

GI State: LARGE INTESTINE. This state is entered once the ingestible device 1900 detects a caecal transition 2422 from the caecum 2410 to the remainder of the large intestine 2412. In some aspects, this may be detected by using a large intestine detection sub-algorithm. This sub-algorithm may be performed automatically when the ingestible device 1900 is in the CAECUM state. In some aspects, the large intestine detection sub-algorithm may determine when the red reflectance 2430 reaches a minimum and converges with the green or the blue reflectances 2426, 2428, in a statistically significant way, or when the infrared reflectance 2432 rises and levels off at a sufficiently large value in a statistically significant way. It will be understood to one skilled in the art that various statistical, filtering, or ad-hoc techniques can be used to identify this point. For example, in some embodiments this may be calculated by finding when the sample mean of the red reflectance 2430 is statistically the same as the blue or green reflectances 2426, 2428. In some embodiments, this may be done by calculating when the infrared reflectance 2432 is, for example, an order of magnitude larger than the other reflectances, or when a finite difference or derivative of the infrared reflectance 2432 has been reduced, for example, to 20% of its maximum value. In some aspects, a large intestine detection sub-algorithm may compare the detected red reflectance 2430 with the detected green reflectance 2426 to determine when the difference is below a threshold value. Similar to our discussion of the other sub-algorithms, in some aspects this algorithm uses a simple moving average as opposed to raw data points. In some embodiments, an advanced version of the algorithm integrates the difference between a simple moving average of the detected red reflectance 2430 and the detected green reflectance 2426 and tests for a difference less than a threshold value. For example, as each new set of data is acquired, the ingestible device 1900 may compute an updated simple moving average. A discreet integral may then be computed by summing the difference between a predetermined number of the most recent simple moving averages. It will be apparent to one skilled in the art that the integral may be computed several different ways, some of which may be more or less computationally efficient than others. For example, taking the difference between appropriately weighted moving averages, or adding and subtracting the newest and oldest simple moving average to the previously computed integral, may produce an equivalent result. In some embodiments the detected infrared reflectance 2432 being above a threshold value may be incorporated into the large intestine detection sub-algorithm.

GI State: END_EXTERNAL. This state is entered after the ingestible device 1900 detects a transition from the large intestine 2412 to the exit 2414. In some aspects, the ingestible device 1900 may detect this through an exit detection sub-algorithm, which may run automatically when the ingestible device is in the LARGE_INTESTINE state. In some embodiments, the ingestible device 1900 may be equipped with a temperature detector, and the exit detection sub-algorithm may simply check for a change in the measured temperature away from the internal body temperature of the patient. For example, if the ingestible device 1900 detects a temperature below 30 degrees Celsius, or outside the range of 30-40 degrees Celsius, it may determine that it has naturally exited the body of the patient.

In some embodiments, the ingestible device 1900 may measure the overall amount of time that has passed since the ingestible device 1900 was first activated in the START state. In some aspects, this measured amount of time may be incorporated into the exit detection sub-algorithm. For example, by determining that a significantly long period of time has passed (e.g., fifteen hours), the ingestible device may determine that an altered temperature reading is a result of a natural exit from the body rather than a temporary disturbance (e.g., being lodged in the stomach as a patient drinks cold water). In some embodiments, the ingestible device 1900 may also use the radial or axial detectors (e.g., detectors 2002a, 2002b, 2002c, 2006a or 2006b) to measure ambient light to help determine an exit from the body. In some embodiments, the ingestible device 1900 may also enter the END EXTERNAL state and become dormant after an extremely long period of time has passed. In some aspects this may serve both as a means for preserving energy, and as a failsafe. For example, regardless of the other indicators, the ingestible device 1900 may enter the END EXTERNAL state and become dormant after seven days have passed.

It will be understood that the locations and transitions discussed in relation to FIG. 24 are for illustrative purposes, and should not be considered limiting. Furthermore, the systems, devices, and methods described herein may be used to identify a number of other locations or transitions (e.g., identifying the ileum and a transition between the duodenum and the ileum by comparing the different wavelengths of light to threshold values). Additionally, some embodiments of the device may reduce the number of states, by consolidating the DUODENUM, JEJUNUM, and CAECUM into a single SMALL INTESTINE state. In this case, the duodenum detection sub-algorithm determines when the ingestible device transitions into the SMALL INTESTINE state, and a caecum detection sub-algorithm determines when the ingestible device transitions away from the SMALL INTESTINE state into the LARGE INTESTINE state. In some embodiments, other states, such as a MOUTH, ILIEUM, or COLON state may also used by the device.

Although we refer specifically to the ingestible device 1900 in connection with FIG. 24, it will be understood that any of the ingestible devices in this application may be used. This includes, for example, the ingestible devices, 10, 300, 302, 304, 306, 700, as well as the ingestible device 2500 discussed in connection with FIGS. 26-28, as well as the other ingestible devices having various combinations of features found on the aforementioned devices.

FIG. 25 illustrates an external view of another embodiment of the ingestible device that may be used for autonomously identifying a location within the gastrointestinal tract, and autonomously sampling from the gastrointestinal tract or releasing medicament into the gastrointestinal tract. Similar to the example ingestible device 700, example ingestible device 2500 depicted in FIG. 25 is configured to perform the location detection methods described herein, and to obtain samples and/or carry substances including medicaments and therapeutics. During transit through the gastrointestinal tract, the ingestible device 2500 may obtain a number of samples based on the determined location of the device, or at a predetermined time after having established a location of the device. The systems, devices, and methods used by ingestible device 2500 are described with reference to FIGS. 25-35, although features of the ingestible device 2500 may be combined with any other portion of this application. Multiple components of the ingestible device 2500 are interchangeable with the components used in describing the ingestible devices 10, 300, 302, 304, 306, 700, and 1900. Therefore, components that are similar to the already described ingestible devices will not be described in great detail, and instead the focus will be on differentiating features of this embodiment. It should also be understood that any of the ingestible devices described in this application (e.g., the ingestible devices 10, 300, 302, 304, 306, 700 and 1900), may be modified to include the systems, devices, and methods discussed in relation to the ingestible device 2500.

An external view of the ingestible device 2500 is depicted in FIG. 25. The ingestible device 2500 is depicted with a housing comprising a first wall portion 2502 connected to first end portion 2504, and a second wall portion 2512 connected to a second end portion 2514. The first wall portion 2502 and the second wall portion 2512 are connected by a connecting portion 2 step 510.

The first wall portion 2502 is depicted with an optically transparent or translucent window 2506. The window 2506 may have different optical properties from the rest of the first wall portion 2502, and may be more transparent or translucent to visible and infrared light than the other portions of the first wall portion 2502. However, in some embodiments the ingestible device 2500 may be adapted to use the first wall portion 14*a* and the first end portion 16*a* from the ingestible device 10 of FIG. 1 instead of the first wall portion 2502 and the first end portion 2504. The first end portion 2504 is substantially similar to first end portion 16*a* illustrated in FIG. 1; however, the first end portion 2504 may have a window located at the end of the device. This window may, in certain aspects, have different optical properties from the rest of the first end portion 2504, and be configured to allow illumination in and out of the end where an axial sensor sub-unit may be located.

The second wall portion 2512 has an opening 2518, and is configured to rotate around the longitudinal axis of the device. The opening 2518 acts as a passageway for samples from the gastrointestinal tract to enter the housing of the ingestible device 2500, or as a passageway for a medicament stored inside of the ingestible device 2500 to be released into the gastrointestinal tract. In some embodiments, a sample acquired by ingestible device 2500 may be analyzed. A gear-motor 704 inside of the ingestible device 2500 is able to rotate, and cause the second wall portion 2512 to move. In some embodiments, this is done by use of a motor pinion connected to the interior of the second wall portion 2512. The motor pinion may be connected using cyanoacrylate, or any other suitable bonding material or adhesive. The second end portion 2514 is connected to the second wall portion 2512, and contains a small opening 2516. The small opening 2516 can be used to anchor the end of the gear-motor 704. The end of the gear-motor 704 may be positioned inside of the small opening 2516, allowing it to be locked into place. In some embodiments, the second end portion 2514 will rotate along with the second wall portion 2512, although in some embodiments the second end portion 2514 will remain stationary as the second wall portion 2512 moves. As the second wall portion 2512 moves, the opening 2518 will move with it. In some configurations, there will be one or more chambers (e.g., the chamber 706 (FIG. 14A)) under the second wall portion 2512. As the opening 2518 moves, the chambers may become alternately exposed to the environment around the ingestible device 2500, or closed off from the environment around the ingestible device 2500.

The PCB 2508 used in the ingestible device 2500 has similar features and functionality to PCB 30 discussed in relation to FIGS. 2A-2E. However, PCB 2508 may have somewhat different electrical and mechanical systems, as described later in FIG. 27, as well as a slightly different firmware discussed in FIG. 28. The PCB 2508 may also be programmed to perform the localization algorithms described in connection with other embodiments of the device, or to additionally or alternately perform other algorithms discussed in relation with FIGS. 29-33. The PCB 2508 may also have an axial sensing sub-unit (e.g., axial sensing sub-unit 42 of FIG. 1A), and it may feature a radial sensor array that utilizes radial illuminators and radial detectors (e.g., the illuminators 1906*a* and 1906*b*, and the detector 1904 of FIG. 19) to localize the device similar to other ingestible devices (e.g., the ingestible devices 10, 300, 302, 304, 306, and 1900 of FIGS. 1A-1B, 3A-6B and 19). To accommodate the other sampling components in the ingestible device 2500, in some embodiments the PCB 2508 may only extend in one direction, and fit into the first wall portion 14*a*.

Figure 26:
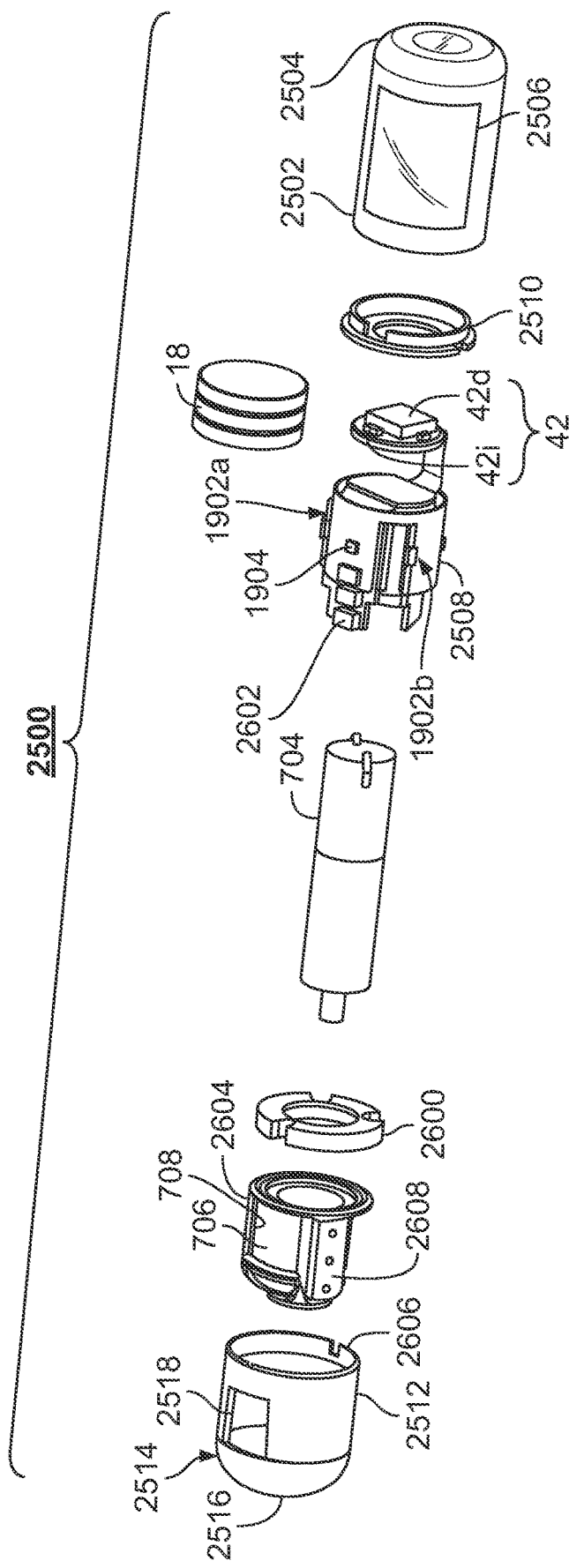
FIG. 26 is an exploded view of the ingestible device of FIG. 25.

FIG. 26 shows an exploded view of the ingestible device 2500. A magnetic ring 2600 is connected to the second wall portion 5212, and rotates along with the second wall portion 5212. In some embodiments, the magnetic ring 2600 may be affixed to second wall portion 2512 using cyanoacrylate, or any other suitable bonding material or adhesive. In some embodiments the interior of the magnetic ring 2600 may interlock with the gear-motor 704, causing the magnetic ring 2600, the second wall portion 2512 and the second end portion 2514 to rotate as the gear-motor 704 rotates. In some embodiments, the second wall portion 2512 or the second end portion 2514 will connect directly to the gear-motor. For example, the gear-motor may interlock with the second end portion 2514 at the small opening 2516. To aid in the operation of the device, the PCB 2508 may feature an additional magnetic sensor 2602, which may determine the orientation of the magnetic ring 2600. For example, the magnetic ring 2600 may contain a series of magnets, positioned such that the magnets are closest to the magnetic sensor 2602 when the opening 2518 is aligned with a chamber 706. The PCB 2508 may then use a detected signal from the magnetic sensor 2602 as part of a feedback loop to adjust the position of the opening 2518 by controlling the gear-motor 704. In general, the PCB 2508 may include a gear-motor controller, and the PCB 2508 may transmit an electrical DC or AC signal to move the gear-motor 704. The locking end 2606 of the second wall portion 2512 is configured to work with the connecting portion 2 step 510. It is designed to allow the second wall portion 2512 to rotate freely relative to the first wall portion 2502, while also remaining connected to the first wall portion 2502.

The storage sub-unit 2604 is similar to the storage sub-unit 702 (FIG. 14A), and is enclosed by the second wall portion 2512. The storage sub-unit 2604 includes chambers, such as the chamber 706. Each chamber 706 on the storage sub-unit 2604 is accessible when the respective chamber opening 708 is aligned with the opening 2518 in the second wall portion 2512. As the second wall portion 2512 moves, chambers may either become accessible to environment around the ingestible device 2500, or they may become inaccessible to the environment around the ingestible device 2500. Each chamber 706 may also incorporate a hydrophilic foam or sponge to assist in acquiring samples. Additionally, this hydrophilic foam or sponge may be provided with or without biological agents for fixation or detection of a target analyte, effectively modifying chamber 706 into a sampling and diagnostics chamber. This may be combined with other diagnostic and assay techniques to diagnose or detect different conditions that may affect specific portions of the gastrointestinal tract.

As depicted in connection with the ingestible device 2500, the storage sub-unit 2604 contains two chambers (e.g., copies of chamber 706) spread around approximately two thirds of the circumference of the storage sub-unit 2604. The final portion of the storage sub-unit 2604 is a null chamber 2608 forming a protrusion that blocks the opening 2518. In some aspects, the null chamber 2608 may be fabricated out of silicone, and in further aspects it may be fabricated out of silicone with a Shore A durometer of approximately 45. In some embodiments the final portion of the storage sun-unit 2604 may contain a third chamber that is either unused, or permitted to be in constant contact with the environment around the ingestible device 2500. In some embodiments, the first chamber may be used to sample the gastrointestinal tract, and the second chamber may be used to resample the gastrointestinal tract, by obtaining a second sample. For example, in some embodiments the ingestible device 2500 may resample the gastrointestinal tract by taking a second sample a fixed period of time after the first sample. In some embodiments, the ingestible device 2500 may resample the gastrointestinal tract at a second location different from the first location. For example, the ingestible device 2500 may be programmed with two different predetermined locations to be sampled, the duodenum and the jejunum. In this case, when the ingestible device 2500 determines that it is located in the duodenum, it may take the first sample, and when the ingestible device 2500 determines it is located in the jejunum, it may take the second sample. In some embodiments, after taking each of the samples, the ingestible device prevent the samples from leaving the chambers (e.g., the copies of chamber 706) by moving the second wall portion 2512 to a position where the opening 2518 is aligned with the null chamber 2608.

In some embodiments, the storage sub-unit 2604 remains stationary as the second wall portion 2512 rotates, but in some embodiments the storage sub-unit 2604 may be rotated as the second wall portion 2512 is stationary. In some embodiments the opening 2518 may be covered by a sliding door, which can move to the side revealing the opening 2518. When used in conjunction with a rotating storage sub-unit 2604, this may be particularly effective for maximizing the usable space inside the storage sub-unit. In some embodiments the storage sub-unit may also be adapted to include sample diagnostics, such as an assay. The storage sub-unit may alternately sequester new samples, perform diagnostics on the samples, and release the samples back into the gastrointestinal tract. In some embodiments the back wall of the chamber 706 may comprise an electro-mechanical actuator to push samples out of the chamber. In some embodiments a similar electromechanical actuator may be used to pull samples or fluid into the chamber by suction. In some embodiments the ingestible device 2500 may also sequester a sample in a chamber 706 once it reaches a particular location by reconfiguring the second wall portion 2512 relative to the storage sub-unit 2604, test the sample using a diagnostic such as an assay, and based on the result of the diagnostic reconfigure the second wall portion 2512 relative to the storage sub-unit 2604 to release a medicament stored in a different one of the chambers 706.

Figure 27:
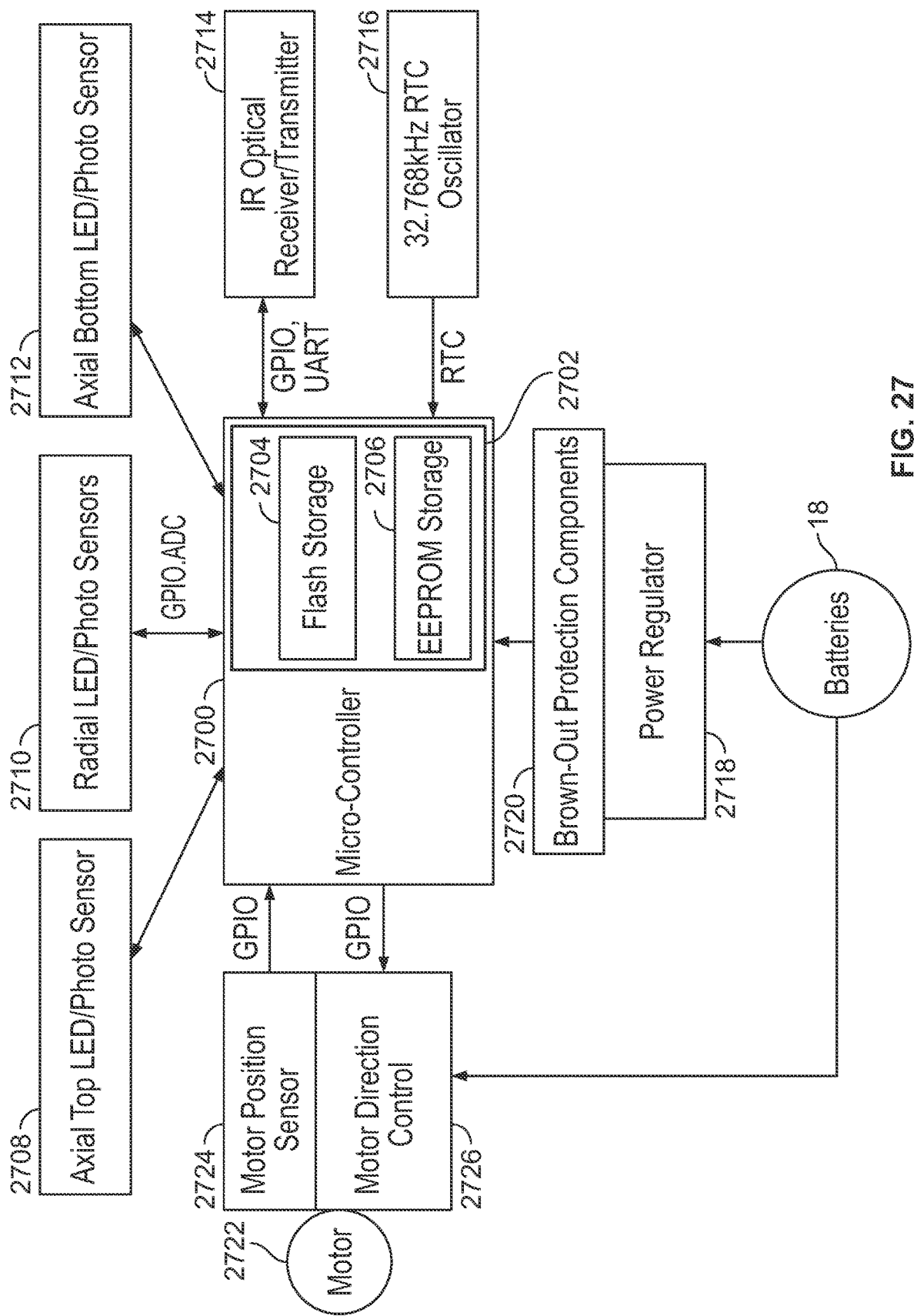
FIG. 27 describes major electrical sub-units corresponding to some embodiments of the device.

FIG. 27 illustrates various electrical sub-units corresponding to some embodiments of the device. In particular, FIG. 27 illustrates electrical sub-units that may be implemented in the PCB 2508 in connection with the ingestible device 2500, but any of the systems, devices, and methods discussed in relation to FIG. 27 may be combined with any other system, device, or method in this application. For example, the systems, devices, and methods illustrated in FIGS. 2A-2E and 15 may supplement or be done in alternate with the systems, devices, and methods in FIG. 27, and vice-versa. In some embodiments, the PCB 2508 is a flex PCB with rigid strengtheners, powered by three Silver Oxide 370 batteries. The electrical system of PCB 2508 is controlled by microcontroller 2700, which in some embodiments may be similar to microcontroller 110 (FIG. 2A). In some embodiments of the ingestible device 2500, the microcontroller 2700 is the STM32L051k8, which has a low power ARM Coretex core. Microcontroller 2700 features a memory sub-unit 2702, which may include both flash storage 2704 and EEPROM storage 2706 for storing both instructions, and for storing data acquired from the various sensors.

The electrical system includes a top axial sensing sub-unit 2708, a radial sensing sub-unit 2710, and in some embodiments may include an additional bottom axial sensing sub-unit 2712, all of which may be similar to the sensing sub-units discussed in relation to FIGS. 2A and 15, and in some embodiments each sub-unit may comprise an LED/

Photo Sensor pair. The microcontroller 2700 may communicate with these sensing sub-units using a general input output interface (e.g., General I/O 112) in combination with an analog-to-digital converter (e.g., analog-to-digital converter 116) for converting and quantifying signals detected by the photo-sensors included in the sensing sub-units 2708, 2710, 2712. The electrical system may also include an IR optical receiver/transmitter 2714, which may be used to assist in localization, or may be used to transmit and receive signals. For example, this may be used in conjunction with the communication sub-unit 120 and optical encoder 20 (FIG. 2A) to communicate with a base station and allow the ingestible device 2500 to be programmed. In some embodiments, the PCB 2508 may also include an RF transceiver for use in communications (e.g., RF transceiver 722). The IR optical receiver transmitter 2714 can communicate with microcontroller 2700 using General I/O 112 or a UART (e.g., Universal Asynchronous Receiver/Transmitter (UART) interface 114 (FIG. 2A).

In some embodiments, the PCB 2508 includes a real time clock (RTC) oscillator 2716 operating at 32.768 kHz. This clock communicates directly with microcontroller 2700, and may be used to quantify capsule transit times with real-time accuracy, or it may be used to track time as the ingestible device goes into a temporary sleep state and wakes itself up at periodic intervals. The power supply for the microcontroller 2700 features a power regulator 2718, controlling and filtering the voltage delivered by the batteries 18, as well as a brown-out protection circuit 2720 that prevents or substantially prevents small variations in voltage from disrupting a device function. For example, in some aspects the brown-out protection circuit may mitigate a possible voltage drop as batteries 18 are used to move a motor 2722. The motor 2722 may be substantially similar to gear-motor 704, but the circuitry may be easily adapted to move other types of motors or actuators. In some embodiments, the brown-out protection circuit 2720 may include a Schottky diode connected between the batteries 18 and the microcontroller 2700, and may additionally include a bulk capacitance on the side of the Schottky diode with the microcontroller 2700. In some embodiments, a voltage drop in batteries 18 due to moving motor 2722 may cause the Schottky diode to electrically isolate microcontroller 2700 from the batteries 18, while allowing microcontroller 2700 to maintain operation by drawing stored energy from the bulk capacitance. In some embodiments, the microcontroller 2700 may also suspend some device functionality while the motor 2722 moves. For example, while the motor 2722 moves, the microcontroller 2700 may suspend use of the sensing sub-units 2708, 2710 and 2712, and draw less energy from the bulk capacitance. In some aspects this brown-out protection circuit may allow the ingestible device 2500 to operate both a motor 2722 and microcontroller 2700 using the same batteries 18. In some embodiments the brown-out protection circuit may also include a voltage sensor for sensing the voltage level of batteries 18, and/or the bulk capacitance, and the ingestible device 2500 may not move the motor 2722 unless one or both of the sensed voltage levels are above a threshold value. For example, the ingestible device 2500 will prevent the motor 2722 from moving unless the voltage on the bulk capacitors is sufficient to maintain operation of the microcontroller 2700 for the duration of the motor movement.

In some embodiments, the PCB 2508 also has a motor position sensor 2724, and a motor direction control 2726 that communicate with microcontroller 2700 by GPIO, which are used in combination to manipulate the motor 2722 (e.g., gear-motor 704). The motor direction control 2726 is a motor direction H-bridge, which can alternate whether a DC-motor (e.g., the motors 2722, 704) rotates clockwise or counter-clockwise. This may be used in combination with a motor-driver (e.g., the motor driver 742 (FIG. 15)) or a motor control sub-unit (e.g., the motor control sub-unit 740 (FIG. 15)). This ensures that opening 2518 can align with a particular chamber opening 708 without disrupting other chambers.

In some embodiments, the motor position sensor 2724 is a magnetic sensor, such as a hall effect sensor, that can detect the orientation of magnetic ring 2600, which is connected to the second wall portion 2512 containing the opening 2518. The combination of the motor position sensor 2724, the microcontroller 2700, and the motor direction control 2726, can act as a simple feedback circuit to ensure that motor 2722 is oriented correctly. In some embodiments, the PCB 2508 may also include other sensors, such as temperature sensors, and may be adapted to include optical, electrical or chemical diagnostics for studying samples acquired in chamber 706. In some embodiments the microcontroller 2700 may also be adapted to sense the location of the chambers (e.g., chamber 706). For example, by using the magnetic sensing sub-unit 2602 in combinations with magnets embedded into the walls of the chambers.

The microcontroller 2700 actuates and monitors the various sensors and sensing sub-units 2708, 2710, 2712 to locate itself within the gastrointestinal tract. For example, microcontroller 2700 may operate the axial and radial sensing sub-units 2708 and 2701, to flash different colors of light, and to detect the resulting reflectance using the photo-sensors in the sensing sub-units. Similarly, in some embodiments, the microcontroller 2700 may obtain temperature data from a temperature sensor as well. These detected data values are stored as logs (e.g., in EEPROM storage 2706 of memory sub-unit 2702), which may be retrieved later on for either post-analysis, or to perform one of the localization algorithms described in this application.

Figure 28:
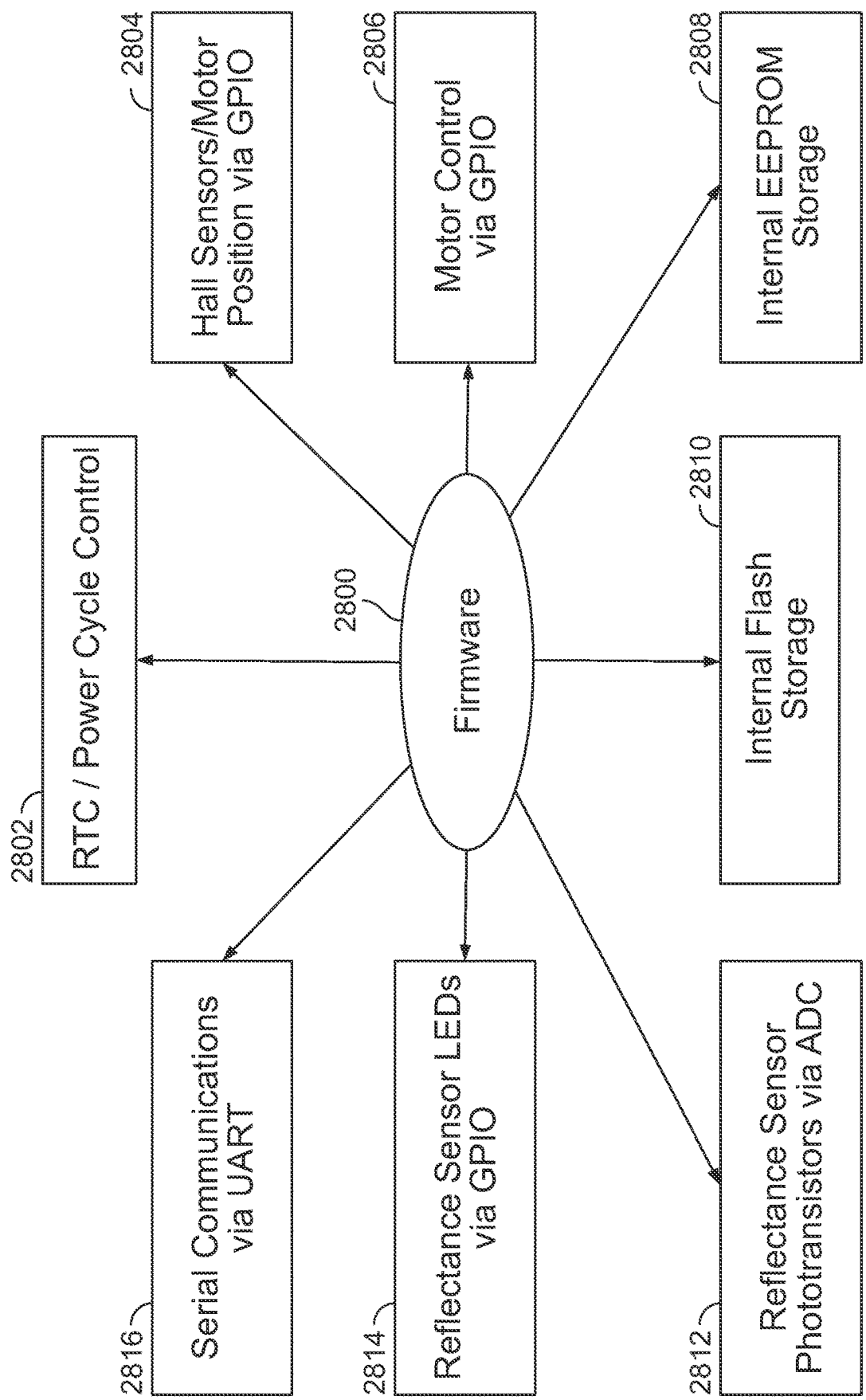
FIG. 28 describes the firmware corresponding to some embodiments of the device.

FIG. 28 illustrates the firmware corresponding to some embodiments of the device. Specifically, FIG. 28 describes the firmware 2800 and software systems that may be used in some embodiments to control the operation of the PCB 2508 and the ingestible device 2500. The firmware 2800 is installed into the internal non-volatile flash memory 2704 of the microcontroller 2700 at the time of manufacture, or during authorized service periods, and generally may not be altered or reprogrammed after it is installed on the ingestible device 2500. In some aspects, this may be done by having the programming leads (i.e., the physical connections to write or re-write to flash storage 2704) be contained within the housing of the ingestible device 2500, or having programming leads printed onto a portion of the flexible circuit board used to construct PCB 2508 which is physically cut off after the firmware 2800 has been installed.

The firmware 2800 controls various functions of the device, as illustrated in FIG. 28. Notably, firmware 2800 is encoded with instructions that may control the function of microcontroller 2700, and by proxy, the systems described in FIG. 27. Real time clock (RTC) and power cycle control 2802 determines how microcontroller 2700 communicates and interacts with RTC Oscillator 2716. In some embodiments, the ingestible device 2500 is set to sleep most of the time, disabling various device functions to preserve energy. The ingestible device 2500 is set to wake-up at pre-defined times, collect sensor data, periodically analyze collected data, perform actions as appropriate (sample, identify GI features) and return to sleep. Maintaining a large percentage of time in sleep mode may conserve onboard power reserves. The power cycle control 2802 allows the ingestible device 2500 to wake-up at appropriate intervals. Two exemplary methods for controlling the operation of the device based on these sleeping and waking intervals are illustrated later on in conjunction with FIGS. 29 and 30. Motor position and magnetic sensing control 2804 contains instructions for allowing microcontroller 2700 to interact with motor position sensor 2724. In some embodiments, the motor position sensor 2724 is replaced by other types of magnetic sensing units (e.g., magnetic sensing unit 2602) which can be used to determine the location and orientation of various portions of the ingestible device. Motor control 2806 contains instructions for allowing microcontroller 2700 to operate motor direction control 2726 via GPIO, and control the motion of motor 2722. In some embodiments, motor 2722 may be one and the same as gear-motor 704, although in some embodiments other types of motors may be used.

The internal EEPROM storage control 2808 contains drivers for allowing the microcontroller 2700 to interact with EEPROM storage 2706. Internal flash storage control 2810 contains similar drivers for allowing the microcontroller 2700 to interact with the flash storage 2704. The reflectance sensor control 2812 contains instructions for the microcontroller 2700 to obtain and quantify light detected by photo sensors (e.g., the photo-sensing half of the sensing sub-units 2708, 2710, and 2712, or detector 1904). In some embodiments, any reflectance (i.e., light reflected onto a detector) will cause a detector to generate a voltage or current directly proportional to the amount of light detected. This is passed into an ADC, and the resulting digital signal can be used by the microcontroller 2700 to quantify the amount of light that was received in the reflectance. The reflectance sensor LED control 2814 contains instructions for the microcontroller 2700 to operate the various illuminators of the ingestible device 2500 (e.g., the LED half of the sensing sub-units 2708, 2710, 2712, or the illuminators 1902a and 1902b). By using a GPIO, the microcontroller 1700 may control when an LED produces light, or in the case of an RGB-LED package, to control the color of light being produced (i.e., select different wavelengths for the illumination). The serial communications control 2816 contains instructions for operating IR optical receiver/transmitter 2714 to communicate signals to and from the device using a Universal Asynchronous Receiver/Transmitter (UART). For example, the microcontroller 2700 may encode a digital pulse train onto the IR transmitter (e.g., using optical encoder 20) to communicate with a base station (e.g., base station 950). Similarly, the IR receiver may be used to receive signals from the base station, allowing a doctor to set device parameters or reprogram select features of the ingestible device 2500.

Although the firmware 2800 is primarily discussed in connection with the electrical subsystem described by FIG. 27, similar firmware can be used to control other electrical systems in an ingestible device (e.g., the system described by FIGS. 2A-2E and FIG. 15). As mentioned above in connection with the RTC and power cycle control 2802, the firmware may contain instructions to preserve device power by setting the ingestible device 2500 to spend a significant portion of time in a sleep mode, and take samples and perform the full range of device functions at periodic intervals. In these embodiments, the firmware 2800 has two primary execution paths, a slow main program loop, and a fast timer based loop. The slow main program loop is illustrated FIGS. 30A-30B, and it may run a list of predefined tasks. Each task in the slow main program loop may be performed at a fixed rate, and respond to non-deterministic external events, such as new data acquired from the optical sensors (e.g., from the sensing sub-units 2708, 2710, 2712). In contrast, the fast timer based loop will periodically interrupt the slow main program loop, and look after processes that need a high speed processing at frequent intervals.

Figure 29:
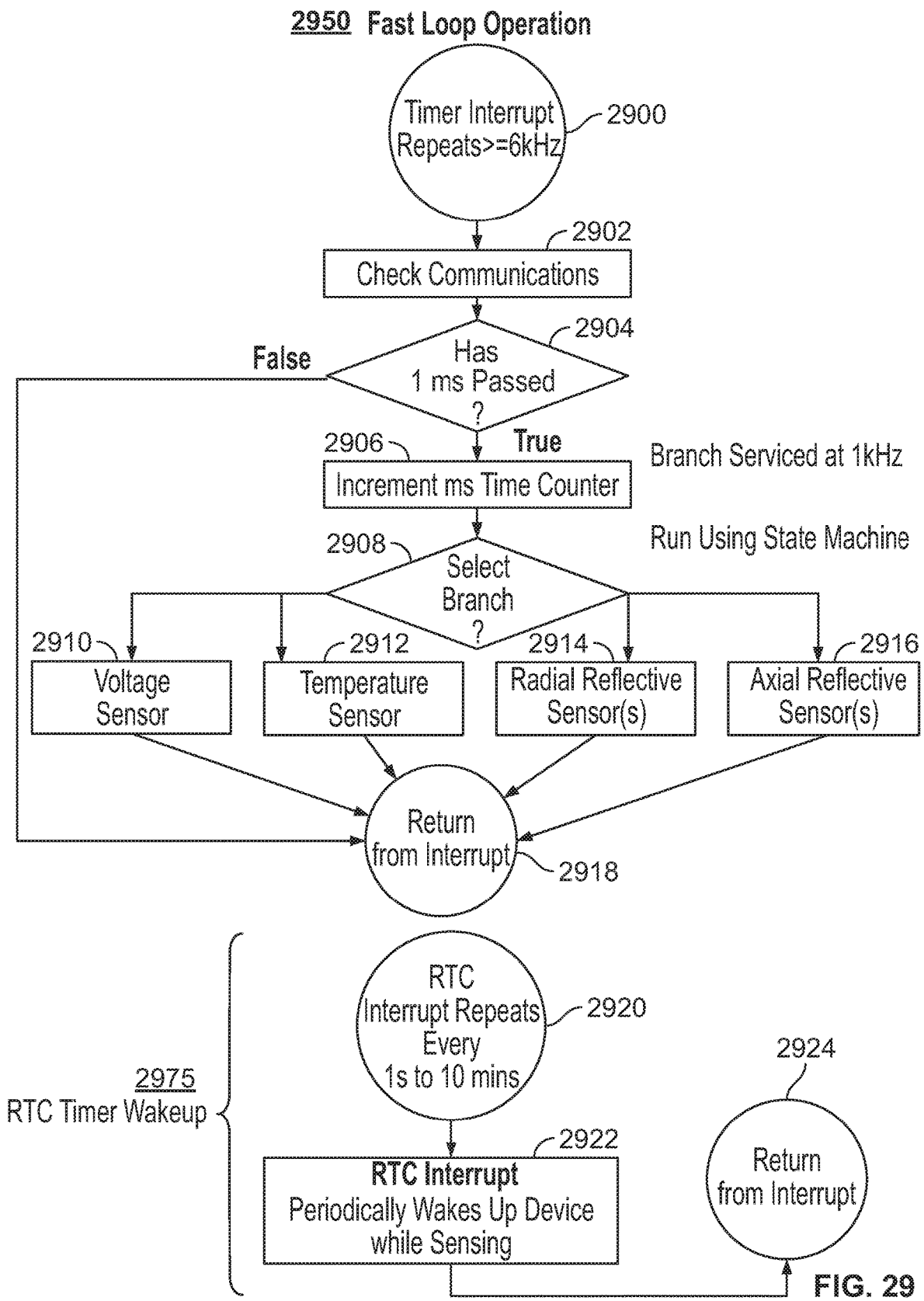
FIG. 29 is a flowchart that describes "Fast Loop" operation of the device, which may allow for high speed processing at short intervals, in accordance with some embodiments of the device.

FIG. 29 is a flowchart that describes some embodiments and processes for waking-up an ingestible device from a sleep or standby state, and operating an ingestible device. In some aspects, the wake-up process 2975 controls the operation of the device, and sets intervals to interrupt a sleeping or stand-by state of the ingestible device 2500, causing it to wake-up and perform the slow-loop process illustrated in FIGS. 30A-30B, as well as the fast loop process 2950. The fast loop process 2950 may periodically interrupt the slow-loop process, and look after processes that need a high speed processing at frequent intervals. For example, after the ingestible device 2500 wakes-up, the slow-loop process may track which task needs to be done next (e.g., collect data or run the localization algorithm), while the fast loop process 2950 may monitor for external communications (e.g., communications from base station 950 (FIGS. 17A-17C)) and operate the sensors.

At step 2900 of the fast loop process 2950, the ingestible device 2500 the fast loop process 2950 interrupts the slow loop process. In order to perform high speed processing, the fast loop process 2950 may interrupt and take control the ingestible device 2500 with a frequency greater than 6 kHz.

At step 2902, the ingestible device 2500 checks for external communications. For example, the ingestible device 2500 may check if there is a signal being received by IR optical receiver 2714 from a base station 950. In some embodiments, the ingestible device 2500 may also be equipped with other types of wireless communication means, such as Bluetooth, near field communications, RF transceivers, and the like. In these cases, the ingestible device 2500 may monitor for any type of communication at step 2902. In some embodiments, if a communication is detected, the ingestible device 2500 may continue to monitor the communication until the communication finishes.

At step 2904, the ingestible device 2500 checks if one millisecond has passed since the last time the time counter at step 2906 was incremented. In some aspects, this may allow the ingestible device 2500 to check for communications at step 2902 at a high frequency, and perform other operations (e.g., servicing sensors at steps 2910, 2912, 2914 and 2916) at a lower frequency. In some embodiments, the ingestible device 2500 may count out one millisecond intervals by decrementing a counter at step 2904, and resetting the counter at step 2906. For example, if process 2950 repeats with a frequency of 6 kHz, the counter will be initially set to "six," and the fast loop process 2950 will repeat 6 times before the ingestible device proceeds to step 2906, resulting in the ingestible device 2500 proceeding to step 2906 in one millisecond intervals. If one millisecond has passed since the last time the time counter at step 2906 was incremented the ingestible device 2500 proceeds to step 2906, otherwise the ingestible device 2500 proceeds to step 2918.

At step 2906, the ingestible device 2500 will increment time counter, tracking the number of milliseconds since the device was woken-up. In some aspects, the time counter may be used by the ingestible device to determine how long particular steps of the slow loop process have been proceeding for. For example, in some embodiment the slow loop process may indicate when the ingestible device 2500 moves a motor (e.g., the motors 2720 or 704) to open the chamber 706 and acquire a sample, and the time counter may be used by the slow loop process to determine how long the chamber 706 has been open.

At step 2908, the ingestible device 2500 selects a sensor to sample. In some embodiments, the ingestible device 2500 will sample the sensors in order, selecting a sensor to sample every millisecond. For example, the ingestible device 2500 may proceed to step 2910 during the first iteration, step 2912 during the second iteration, step 2914 during the third iteration, and step 2916 during the fourth iteration, and then repeat the sequence after all the sensors have been sampled. In some embodiments certain sensors may be sampled more or less often than others. For example, the temperature sensor may be ignored while the ingestible device is inside the small intestine, and the ingestible device 2500 may not proceed to step 2912 at all. In some embodiments, the ingestible device 2500 will communicate data with a sensor while it is being sampled, but the sensor will continue to operate while it is not being sampled. For example, every time the ingestible device 2500 samples a radial sensing sub-unit, it may determine if a particular radial LED should be turned on, or turned off, or left in its current state, and the radial LED will persist in its current state while not being sensed. In some embodiment of the ingestible device 2500, the selecting a sensor to sample may additionally comprise the use of a multiplexor.

At step 2910, the ingestible device 2500 uses voltage sensors to diagnose possible malfunctions within the electrical system (e.g., the electrical system described by FIG. 27). For example, the ingestible device 2500 may test communications to the various sub-units (e.g., motor 2722) using the GPIO, and the ingestible device may determine the current voltage being supplied by batteries 18. In some embodiments, the ingestible device 2500 may only operate a motor (e.g., the motors 704 or 2722) while the sensed voltage of the batteries 18 is above a threshold value.

At step 2912, the ingestible device 2500 uses a temperature sensor to gather a temperature measurement. For example, the ingestible device 2500 may gather a temperature measurement to determine entry or exit from the body. In some embodiments, temperature measurements can also be used to estimate other locations within the gastrointestinal tract. For example, in some embodiments the ingestible device 2500 may determine that sudden changes in temperature (e.g., as a result of a patient ingesting a hot meal or a cold drink) indicate the ingestible device may be located in the stomach.

At step 2914, the ingestible device 2500 uses radial sensors (e.g., radial sensing sub-unit 32 and 2710) to gather radial reflectance data. For example, the ingestible device 2500 may use microcontroller 2700 to instruct radial sensing sub-unit 2710 to flash a particular wavelength of light, and measure the resulting reflectance. This can be done to gather radial reflectance data (e.g., for the radial reflectance data series 602 (FIGS. 13A-13B), or the detected red green or blue reflectances 2426, 2428 and 2430 (FIG. 24)). Additionally, in some embodiments the ingestible device 2500 may test the radial sensing sub-units to detect device malfunctions. For example, if a first radial illuminator is not producing a resulting signal in any of the radial detectors, but the other radial illuminators are, then the ingestible device 2500 may determine that first radial illuminator is not functioning properly.

At step 2916, in some embodiments the ingestible device 2500 uses axial sensors (e.g., the axial sensing sub-unit 42, 2708, and 2712) to gather axial reflectance data. This can be done to gather axial reflectance data (e.g., for the axial reflectance data series 604 (FIGS. 13A-13B), or the detected infrared reflectance 2432 (FIG. 24)). Additionally, in some embodiments the ingestible device 2500 may use these data to detect anomalies within the gastrointestinal device, or possible device malfunctions. For example, if the ingestible device 2500 measures a number of abnormal data points as a result of a medical anomaly, the ingestible device 2500 may use the fast loop process 2950 to gather more data points near the anomaly.

At step 2918, the ingestible device 2500 terminates the fast loop process 2950 and returns to a sleeping state. However, in some embodiments the fast loop process 2950 may begin again almost immediately again thereafter.

RTC wake-up process 2975 is distinct from fast loop method step 2900, and in some aspects it may control operation of the device based on the power saving settings (e.g., as part of RTC and power cycle control 2802 (FIG. 28)). When the ingestible device 2500 temporarily enters a sleep state, RTC oscillator 2716 continues to run and track the passage of time. The microcontroller 2700 is configured to wake-up the ingestible device 2500 at regular intervals based on the RTC oscillator 2716 output, and perform the primary sampling and data gathering functions of the device.

At step 2920, the ingestible device 2500 receives a signal from the RTC oscillator 2716 to wake-up. In some aspects, this may occur at an interval between one second and 10 minutes, and in further aspects, the interval may depend on the current location of the ingestible device, and the ingestible device settings and power reserves. For example, while in the stomach (e.g., in the start 2402 or stomach 2404 (FIG. 24)), the ingestible device 2500 may be woken-up and take data samples every one second. In the small intestine (e.g., in the duodenum 2406 and the jejunum 2408 (FIG. 24)), there is less variability in the environment around the ingestible device 2500, and the device may be woken up and take data samples every 30 seconds instead.

At step 2922, the ingestible device 2500 wakes up, and begins to perform the fast/slow loop operation of the device, which is described in connection with FIGS. 30A-30B and process 2950.

At step 2924, the ingestible device 2500 has finished gathering a new data set and performing the localization algorithm, and it returns to a sleeping or standby state. Depending on the device settings, the ingestible device 2500 may configure the RTC oscillator to wake-up the device again after a predetermined period of time.

It is contemplated that the steps or descriptions of FIG. 29 may be used with any other embodiment of this application. In addition, the steps and descriptions described in relation to FIG. 29 may be done in alternative orders or in parallel to further the purposes of this application. For example, performing the steps described by step 2910, step 2912, step 2914 and step 2916 in parallel may reduce latency, or allow the gathered data points to be synchronized to a particular time. Furthermore, it should be noted that any of the ingestible devices or systems discussed in this application could be used to perform one or more of the steps in FIG. 29.

Figure 30A:
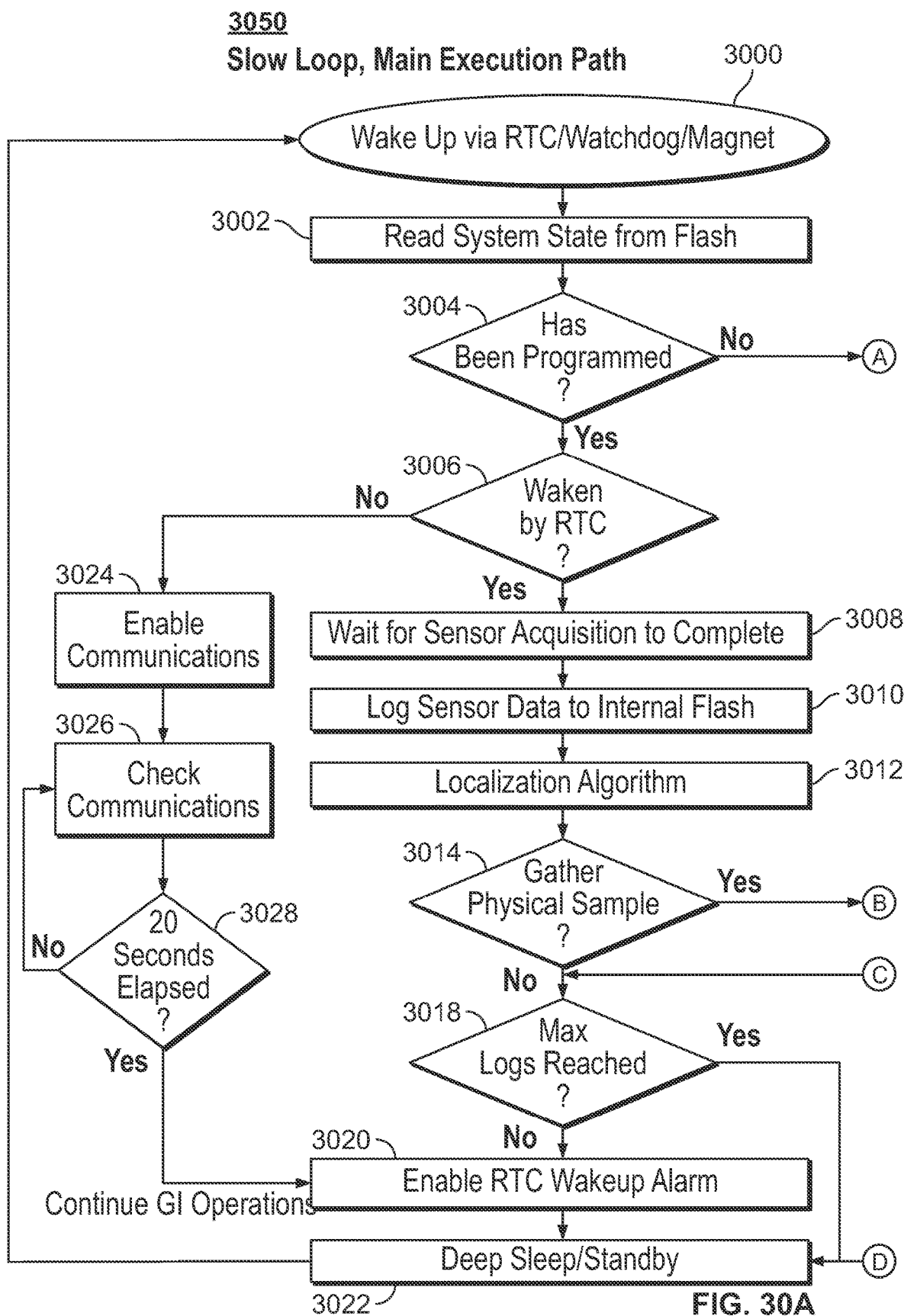
FIGS. 30A and 30B depict a flowchart that describes "Slow Loop" operation of the device, in accordance with some embodiments of the device.
Figure 30B:
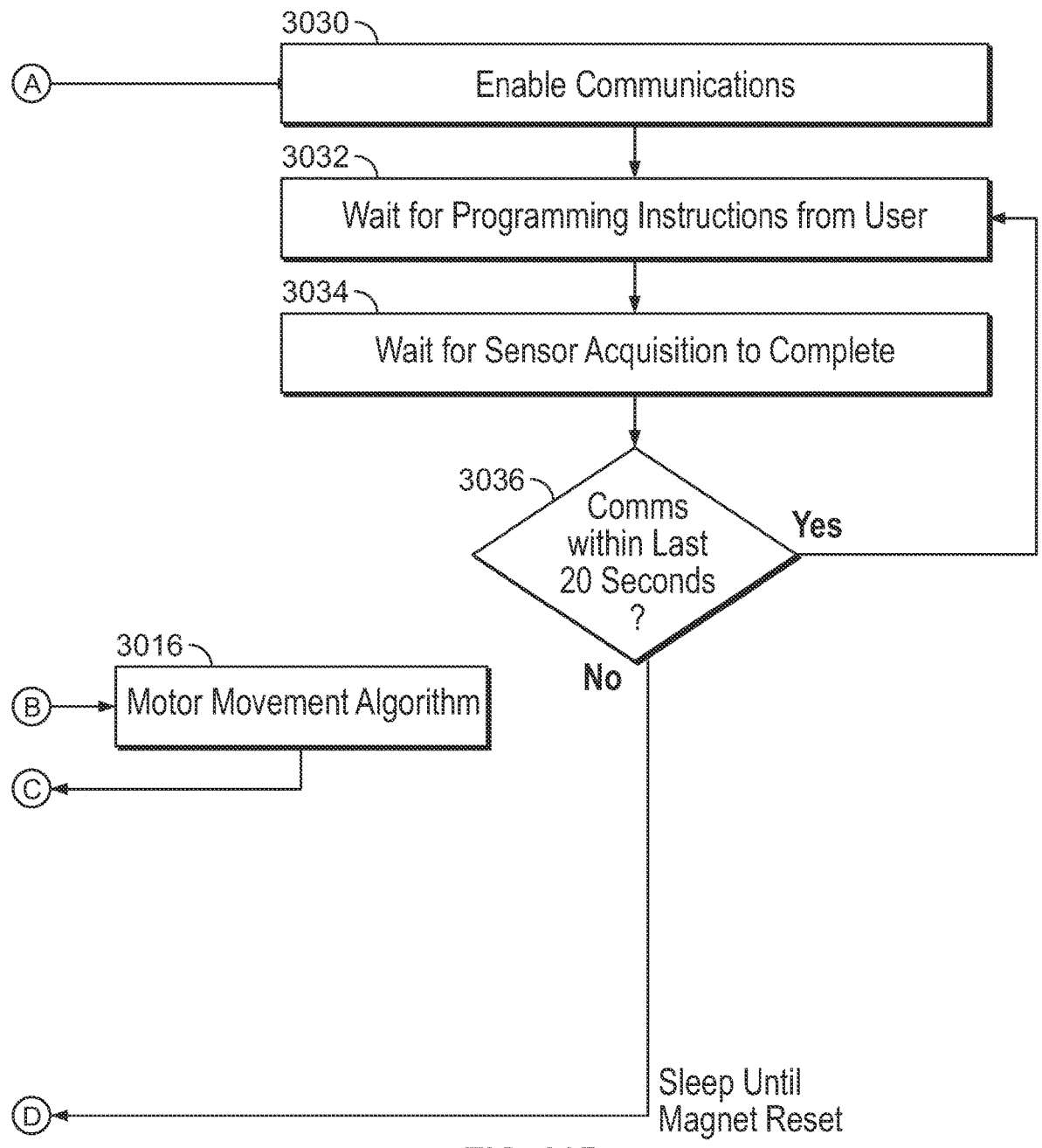

FIGS. 30A-30B are a flowchart that illustrates various aspects of the slow loop operation of an ingestible device, in accordance with some embodiments of the device. An ingestible device (e.g., the ingestible device 2500) may spend most of the time in a sleeping or standby state in order to preserve energy reserves. In some aspects, every time the ingestible device 2500 is woken up, the fast loop process 2950 and the slow loop process 3050 will run in order to gather data, run localization algorithms to determine the location of the device, and take samples if necessary.

The slow loop process 3050 begins at step 3000. At step 3000, the ingestible device 2500 is woken up by a real time clock (e.g., at step 2922 of wake-up process 2975), a magnet (e.g., from activating the magnetic switch 162 (FIG. 2A)), or by a watchdog algorithm. In some aspects, a watchdog algorithm will safeguard against an error that halts execution of a program. In some embodiments the watchdog algorithm will comprise an independent hardware timer that will periodically check various device functions, sensors, and/or hardware/software systems, and only allow the ingestible device 2500 to operate if all of the checked functions and/or systems are operating correctly. For example, if the ingestible device 2500 is unable to establish a connection with a sensor, it may reset itself by setting an RTC alarm and entering a sleep or stand-by state.

At step 3002, a system state is read from memory. For example, a current state of the ingestible device 2500 may be stored in flash storage 2704. The state may indicate a current location of the ingestible device 2500 within the gastrointestinal tract. The state may also indicate if the ingestible device 2500 has been programmed and initialized properly For example, the state may indicate whether a doctor or technician properly set up the ingestible device 2500 prior to administering the ingestible device 2500 to a patient.

At step 3004, the ingestible device 2500 determines if it has been properly programmed. If the ingestible device 2500 has been programmed, the process may proceed to step 3006, if the ingestible device 2500 has not been programmed, the process may proceed instead to step 3030.

At step 3006, the ingestible device 2500 determines if it has been woken-up by a real time clock (e.g., at step 2922 of wake-up process 2975). If the ingestible device 2500 has been woken up by a real time clock, the process may proceed to step 3008, and otherwise proceed to step 3024.

At step 3008 the ingestible device 2500 gathers data from the various sensors on the device (e.g., from the axial and radial sensing sub-units 2708, 2710 and 2712 (FIG. 27)). The sensing pattern and data acquisition pattern can differ based on the intended use of the ingestible device 2500, but in some embodiments the ingestible device will gather a red, green, blue, and infrared reflectance data sample, as well as a temperature measurement.

At step 3010, the ingestible device 2500 logs the sensor data gathered at step 3008 to internal memory (e.g., to the memory sub-unit 2702 (FIG. 27)). In the ingestible device 2500, data logs are recorded to 50 kB of internal flash memory (e.g., the flash storage 2704 (FIG. 27)) and may be retrieved when requested by an external system, although a different amount of memory may be available in some embodiments. In some aspects, a data log will include a capsule transit time, derived through either an algorithm or taken from RTC oscillator 2716, as well as a full set of the sensor data corresponding to red, green, blue, and infrared reflectances along with a temperature measurement.

At step 3012, the ingestible device 2500 runs a localization algorithm (e.g, as described by FIGS. 9-13 or FIG. 24) to determine the location of the device. In some aspects, the ingestible device 2500 does this by analyzing either the sensor data acquired at step 3008, or using a data set of previous and current sensor data stored in flash memory (e.g., the flash storage 2704). For example, the ingestible device may use a duodenum detection algorithm to determine a pyloric transition (e.g., pyloric transition 2416 (FIG. 24)) from a stomach (e.g., stomach 2404 (FIG. 24)) into a duodenum (e.g., duodenum 2406 (FIG. 24)).

At step 3014, the ingestible device 2500 determines if a physical sample will be gathered. For example, the ingestible device 2500 may be programmed to gather a sample as soon as a particular region of the gastrointestinal tract is identified at step 3012. The ingestible device 2500 may also be programmed to gather a sample a certain amount of time after a particular region of the gastrointestinal tract is identified at step 3012. For example, the ingestible device 2500 may be programmed to gather a sample as soon as the jejunum is detected, or gather a sample 10 minutes after the duodenum is detected. If the ingestible device 2500 is to gather a sample, the ingestible device 2500 may proceed to step 3016, and otherwise it may proceed to step 3018.

At step 3016, the ingestible device 2500 uses a motor movement algorithm to gather a physical sample. This may be done by causing the device to change from one configuration that does not allow material into a sample chamber, to a second configuration that allows material into the sample chamber. For example, the ingestible device 2500 may use microcontroller 2700 to transmit a signal to motor 2722 to move the second wall portion 2512, and align opening 2518 with a chamber opening 708. After a predetermined period of time, such as 10 minutes, the ingestible device 2500 may also cause the motor 2722 to rotate the opening 2518 away from the chamber opening 708, sealing off the chamber 706 with the sample inside.

At step 3018, the ingestible device 2500 may determine if the maximum number of sensor logs have been reached. In some embodiments, the ingestible device 2500 will have 50 kB of flash memory available for storing sensor data. In some embodiments, this is sufficient for recording about 5000-10000 samples, depending on the number of sensors, the data format, and the precision used. In some embodiments the ingestible device 2500 may also remove data samples, or store the data samples in compressed format. For example, the ingestible device 2500 may remove every other data sample after it is no longer needed for localization, leaving enough resolution for a physician or doctor to interpret the data afterwards. For data that is largely redundant or linear (e.g., temperature data taken within the body), the ingestible device 2500 may approximate portions of the data set as a linear function, storing the start and end points, and reducing the total amount of memory needed. If a maximum number of logs has been reached, the ingestible device 2500 may proceed to step 3022, otherwise the ingestible device 2500 may proceed to step 3020.

At step 3020, the ingestible device 2500 sets a real time clock wake-up alarm. In some embodiments, the ingestible device 2500 may be configured to set an alarm to wake-up the device and gather a new set of data at a later time. In some aspects, the interval between sleeping and waking-up is between one second and 10 minutes. When the alarm goes off (e.g., at step 2920 of process 2975), the ingestible device 2500 is interrupted from a sleep or standby state, and process 3050 will repeat.

At step 3022, the ingestible device 2500 will enter a deep sleep or standby state. In some embodiments, if no RTC wakeup alarm is set, the ingestible device 2500 will go into a deep sleep by default, and suspend some device functions. In some embodiments, the ingestible device 2500 shuts off some device functions in a standby state, but will continue to monitor a real time clock (e.g., RTC oscillator 2716 (FIG. 27)) to determine when the ingestible device 2500 is to resume operation.

At step 3024, the ingestible device 2500 will enable communications. In some embodiments, the ingestible device 2500 may deactivate communications to preserve energy reserves and avoid depleting battery 18. However, in some embodiments the ingestible device 2500 will check for external communications (e.g., from the base station 950 via IR optical receiver 2714) if it is woken by something other than the RTC alarm. This may be done by powering and operating the IR optical receiver 2714 or communication sub-unit 120. In some embodiments, the ingestible device 2500 may use other types of communication, such as radio frequency (RF), Bluetooth, or other near field communications (NFC) that can be turned on and off on-demand.

At step 3026, the ingestible device 2500 checks for external communications. For example, after ingestible device 2500 activates communications (e.g., communication sub-unit 120), the ingestible device 2500 may monitor IR optical receiver 2714 for communications from base station 950 in some embodiments.

At step 3028, the ingestible device 2500 will wait for an incoming communication for 20 seconds. If no communication is detected for 20 seconds, the ingestible device 2500 will turn off communications to preserve energy. In some embodiments the ingestible device 2500 may wait for a different period of time, or it may reset the 20 second timer whenever incoming communications are received.

At step 3030, the ingestible device 2500 will enable communications by default if the ingestible device 2500 has not been programmed. In some embodiments, the ingestible device 2500 needs to be programmed or initialized by a doctor or technician before being administered to a patient. If no programming is found on the ingestible device 2500, it will enable communications and wait for programming instructions by default.

At step 3032, the ingestible device 2500 will wait for programming instructions from a user. In some embodiments, a user may be provided with a computer, phone, tablet or watch application, a radio transceiver, a base station, or the like, for communicating with the ingestible device 2500. For example, a user may be provided with a base station 950 capable of transmitting infrared signals to the ingestible device 2500, which will be detected and interpreted (e.g., signals detected by the IR optical receiver 2714 and interpreted by the communication sub-unit 120).

At step 3034, the ingestible device 2500 will wait for the sensor acquisition to complete. After the ingestible device 2500 begins to receive incoming communication signals, the ingestible device 2500 will wait till the full communication has been received. For example, it may take a few minutes for a user to program the ingestible device 2500, and the ingestible device 2500 will keep the communications channel open while instructions are being received.

At step 3036, the ingestible device 2500 will check if communications have been received in the last 20 seconds. Similar to step 3028, the ingestible device 2500 will turn off to preserve energy if no communication is detected for 20 seconds. In some embodiments the ingestible device 2500 may wait for a different period of time.

It will be understood that the steps and descriptions of the flowcharts of this disclosure, including FIGS. 30A-30B, are merely illustrative. Any of the steps and descriptions of the flowcharts, including FIGS. 30A-30B, may be modified, omitted, rearranged, performed in alternate orders or in parallel, two or more of the steps may be combined, or any additional steps may be added, without departing from the scope of the present disclosure. For example, the ingestible device 2500 may continue to acquire new data samples and run the localization algorithm at the same time that a sample is being acquired. Furthermore, it should be noted that the steps and descriptions of FIGS. 30A-30B may be combined with any other system, device, or method described in this applications, and any of the ingestible devices or systems discussed in this application could be used to perform one or more of the steps in FIGS. 30A-30B.

Figure 31:
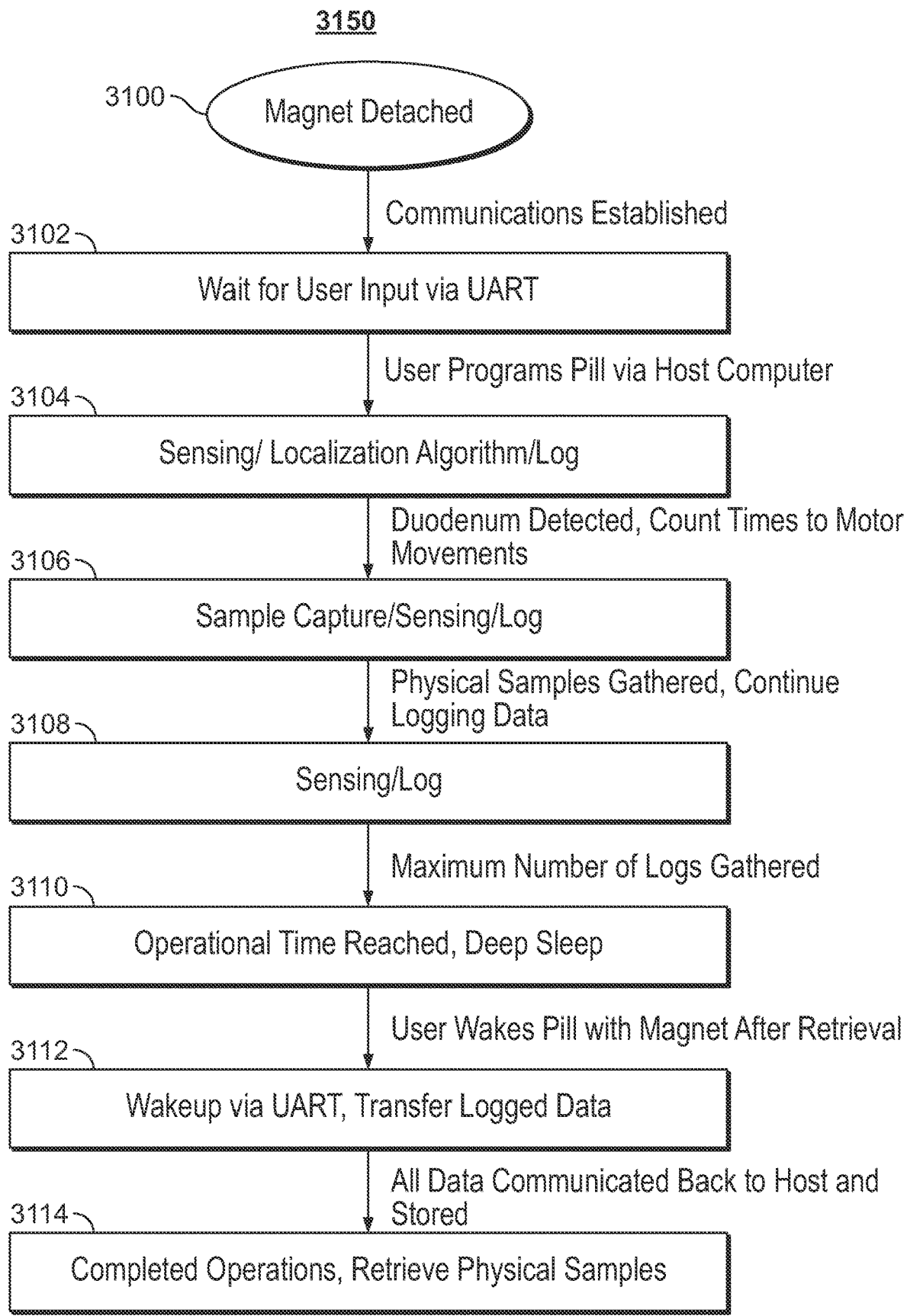
FIG. 31 is a flowchart that describes the operating states of the device in an example application, in accordance with some embodiments of the device.

FIG. 31 is a flowchart that illustrates the general operation of the device, in accordance with some embodiments of the device. In some aspects, sample operation process 3150 describes using an ingestible device to procure a sample from the gastrointestinal tract of a patient. Although FIG. 31 may be described in connection with the ingestible device 2500 for illustrative purposes, this is not intended to be limiting, and either portions or the entirety of the process described in FIG. 31 may be applied to any device discussed in this application (e.g., the ingestible devices 10, 300, 302, 304, 306, 700, and 1900), and any of the ingestible devices may be used to perform one or more parts of the process described in FIG. 31. Furthermore, the features of FIG. 31 may be combined with any other systems, methods or processes described in this application. For example, the process described by FIG. 31 may utilize the hardware and electrical systems in FIGS. 2, 15, 27 and 28, or the localization methods in FIG. 8-13, 21-24 or 32-33.

At step 3100, the ingestible device 2500 will detect if it has been activated by being detached from a magnet. As described in FIG. 2A, an ingestible device (e.g., the ingestible device 2500) may have a magnetic switch 162 for turning on or off the device. After being manufactured, the ingestible device may be placed in a specialized container near a magnet, and the resulting magnetic field that keeps the magnetic switch 162 in the "Off" position. When the ingestible device 2500 is ready to be programmed by a user and administered to a patient, the ingestible device 2500 is moved away from the magnet, and the magnetic switch 162 will change to the "On" position. Once the ingestible device 2500 is turned on for the first time, it may attempt to establish communications.

At step 3102, the ingestible device 2500 will wait for user input via UART. The ingestible device is provided with a communications sub-unit (e.g., communication sub-unit 120), which may be used to communicate with the ingestible device 2500 via UART (e.g., Universal Asynchronous Receiver/Transmitter (UART) interface 114). The ingestible device 2500 will then provide an opportunity for a user to program the device. In some embodiments, the ingestible device 2500 may be provided along with a base station or dock, which may be connected to a computer, tablet, handheld device, smart phone or smart watch; for example, for a user to program the ingestible device 2500. In some embodiments, the ingestible device 2500 may also communicate using other means, such as radio frequency, Bluetooth, near field communications, and the like, all of which may be used to program the ingestible device 2500 or to retrieve information from the ingestible device 2500. In some aspects, the ingestible device 2500 is administered to a patient after being programmed and initialized by a user.

At step 3104, the ingestible device 2500 will perform sensing, log data, and perform a localization algorithm to determine the location of the device. After being administered to a patient, the ingestible device 2500 will proceed to gather data from sensors, log data, and perform localization algorithms to identify the location of the device based on the gathered data. For example, the ingestible device 2500 may gather a set of axial and radial data as it transits through the gastrointestinal tract, and perform the localization algorithm described in connection with FIGS. 8-13. As another example, the ingestible device 2500 may gather sets of reflectance data from illumination at different wavelengths, and perform the localization algorithm described in connection with FIG. 24. In some aspects, the ingestible device 2500 will attempt to identify a pyloric transition (e.g., pyloric transition 2416 (FIG. 24)) as it enters the duodenum portion of the small intestine (e.g., duodenum 2406). Once the ingestible device 2500 determines that it is located in the duodenum, the ingestible device may either take a sample, or wait a predetermined period of time (e.g., 10 minutes) before taking a sample.

At step 3106, the ingestible device 2500 will gather a sample, and continue gathering and logging sensor data. After locating the duodenum, the ingestible device may take a sample from the gastrointestinal tract in the environment around the device, by providing access to a sampling chamber (e.g., chamber 706). For example, the ingestible device 2500 may use a motor (e.g., the motor 704, 2722) to change the device from one configuration that does not allow samples from the gastrointestinal tract to enter the sampling chamber, to another configuration that does allow samples from the gastrointestinal tract to enter the sampling chamber. This may be accomplished by transmitting a signal from microcontroller 2700 to motor 2722 to move the second wall portion 2512 in such a way that opening 2518 is aligned with the chamber opening 708 for the sampling chamber. Similarly, after waiting a certain period of time, the ingestible device 2500 may move back the second wall portion 2512 to seal off the sampling chamber after a sample has been procured. As the sample is being gathered, as well as afterwards, the ingestible device 2500 will continue to measure and log sensor data.

In some embodiments, the ingestible device 2500 will be configured to release a medicament rather than gather a sample. For example, the chamber 706 may be provided with a drug, powder, liquid, or other medicament prior to the ingestible device 2500 being administered to the patient. In some embodiments a user may be provided with the ability to load a medicament into the chamber 706. For example, during the time that the ingestible device 2500 is being programmed (e.g., by a user using a base station 950) the user may be provided with the ability to transmit instructions to the ingestible device 2500 to expose the chamber 706 by rotating the second wall portion 2512.

In some embodiments, the ingestible device 2500 will be configured to study the captured sample using diagnostics. For example, each chamber 706 may also incorporate a hydrophilic foam or sponge to assist in acquiring samples. Additionally, this hydrophilic foam or sponge may be provided with or without biological agents for fixation or detection of a target analyte, effectively modifying chamber 706 into a sampling and diagnostics chamber. This may be combined with other diagnostic and assay techniques to diagnose or detect different conditions that may effect specific portions of the gastrointestinal tract.

At step 3108, the ingestible device 2500 will continue gathering and logging sensor data, even after having obtained one or more samples. In some aspects, the ingestible device 2500 will continue to log sensor data until a maximum number of data logs have been gathered.

At step 3110, the ingestible device 2500 will enter a deep sleep state after reaching maximum operation time, detecting an exit from the body, or logging a maximum number of data samples. In some aspects, the ingestible device 2500 turns off some device functions in the deep sleep state, until it is woken up. In some embodiments the ingestible device 2500 may be woken up use of a magnet or base station provided to a user. In some embodiments, a patient may retrieve the ingestible device 2500 after it has exited the body, and the gathered samples and data logs can be collected from the retrieved device. In some embodiments, an ingestible device may use wireless communication techniques in-vivo, such as RF, Bluetooth or near field communications, to transmit the gathered data to a computer, base station, tablet, phone, smart-watch, or other similar device.

At step 3112, the ingestible device 2500 may be woken-up via UART after being retrieved by a user. In those embodiments where the device has been retrieved by the user, a retrieved device may be brought back to a base station (e.g., the base station 950) or similarly equipped computer for data and sample retrieval. In some embodiments, the ingestible device 2500 will also be woken up from its deep sleep by exposure to a magnet; for example, a magnet that may be provided as part of base station 950.

At step 3114, the ingestible device 2500 will have completed its operation, and will provide a user with the ability to retrieve physical samples. After being retrieved and reactivated from the deep sleep state, the ingestible device 2500 may automatically communicate collected data back to the user, and it may provide access to chamber 706. In some embodiments, a user or certified technician may be provided with means for collecting the physical memory and samples directly from the ingestible device 2500. For example, by providing special tools for disassembling the ingestible device 2500 to authorized individuals, any potentially sensitive data or samples can be protected from being accessed by unauthorized users.

It will be understood that the steps and descriptions of the flowcharts of this disclosure, including FIG. 31, are merely illustrative. Any of the steps and descriptions of the flowcharts, including FIG. 31, may be modified, omitted, rearranged, performed in alternate orders or in parallel, two or more of the steps may be combined, or any additional steps may be added, without departing from the scope of the present disclosure. For example, the ingestible device 2500 may enter a deep sleep state immediately after collecting a sample, in order to preserve energy. Furthermore, it should be noted that the steps and descriptions of FIG. 31 may be combined with any other system, device, or method described in this applications, and any of the ingestible devices or systems discussed in this application could be used to perform one or more of the steps in FIG. 31.

Figure 32:
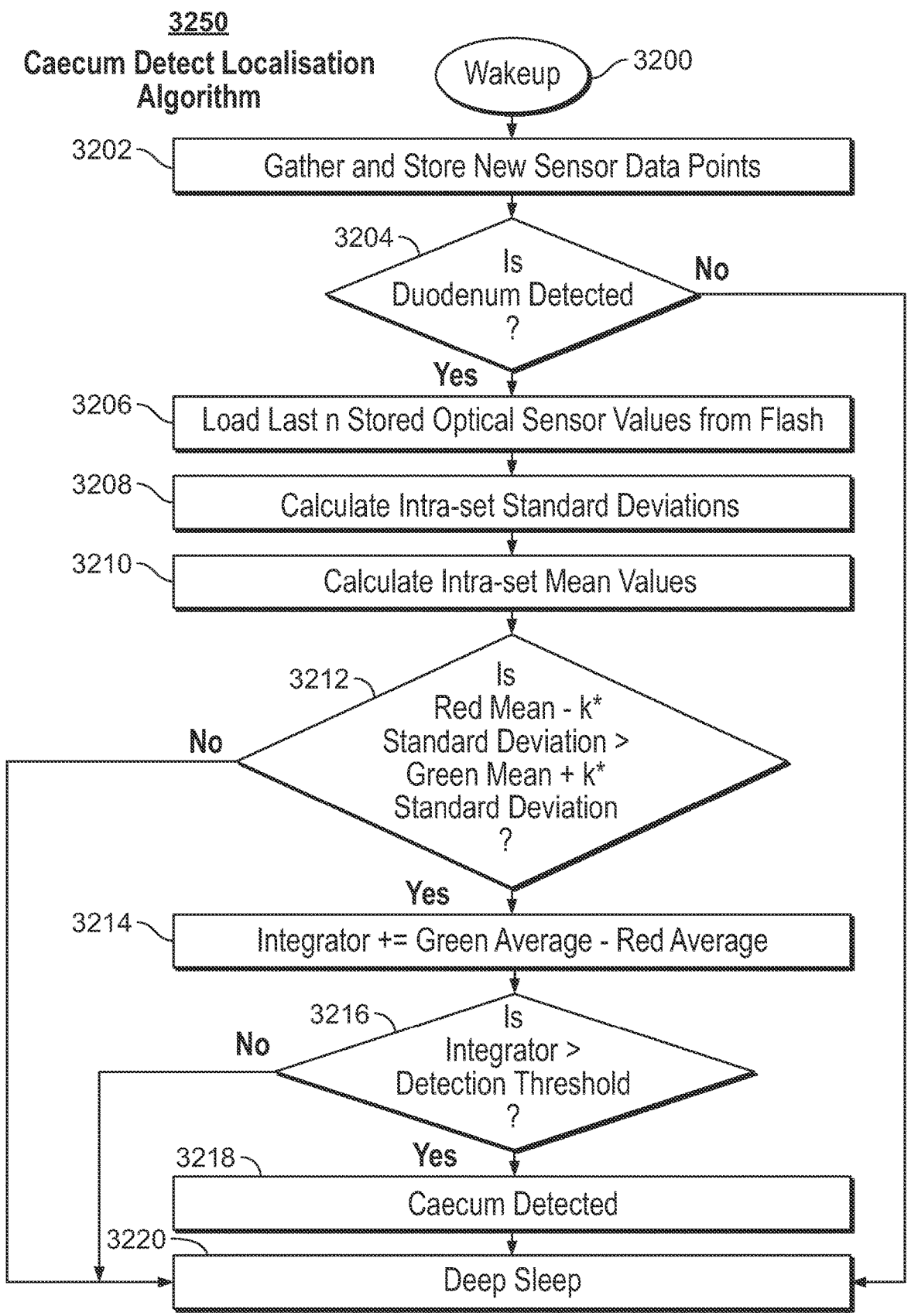
FIG. 32 is a flowchart describing a caecum detection algorithm used in some embodiments of the device.

FIG. 32 is a flowchart illustrating some aspects of a caecum detection algorithm used by the device. Although FIG. 32 may be described in connection with the ingestible device 2500 for illustrative purposes, this is not intended to be limiting, and either portions or the entirety of the caecum detection process 3250 described in FIG. 31 may be applied to any device discussed in this application (e.g., the ingestible devices 10, 300, 302, 304, 306, 700, and 1900), and any of the ingestible devices may be used to perform one or more parts of the process described in FIG. 32. Furthermore, the features of FIG. 32 may be combined with any other systems, methods or processes described in this application. For example, portions of the algorithm described by the process in FIG. 32 may be integrated into any of the algorithm described by FIG. 24.

At step 3200 the ingestible device 2500 wakes up. This may be done due to a previously set RTC alarm set by the ingestible device 2500.

At step 3202, the ingestible device 2500 gathers and stores new sensor data points. The ingestible device 2500 starts by flashing different colored LEDs (e.g., the illuminators 1902a and 1902b) to produce illumination at red and green wavelengths, and detecting (e.g, by detector 1904) the resulting reflectance coming from the environment around the ingestible device 2500. These data points are then stored in flash memory.

At step 3204, the ingestible device 2500 determines if a duodenum has already been detected. For example, if the current state of the ingestible device 2500 is the DUODENUM or JEJUNUM state, or if a duodenum detection algorithm has already determined that a pyloric transition (e.g., pyloric transition 2416) has occurred.

At step 3206, the ingestible device 2500 loads the last "n" stored optical sensor values from flash memory (e.g., the flash storage 2704). The number of points "n" should be sufficiently large to calculate a statistically significant average and standard deviation, but in many aspects a value 30 is chosen.

At step 3208, the ingestible device 2500 calculates intra-set standard deviations.

At step 3210, the ingestible device 2500 calculates intra-set mean values.

At step 3212, the ingestible device 2500 compares the red data to the green data. In some embodiments, this may involve subtracting a multiple of the red standard deviation from the mean of the red data, and subtracting a multiple of the green standard deviation from the mean of the green data. In some embodiments, the multiple, "k", is chosen to be approximately 1.5. In some embodiments, the multiple may be programmed by a user prior to administering the device to a patient, or the multiple may be changed based on the measured sensor data. If the condition in step 3212 is not satisfied, the ingestible device 2500 considers that data point unreliable, and it is not considered.

At step 3214, the ingestible device 2500 increases the value of an integrator. In some embodiments, the ingestible device 2500 adds the difference between the mean of the green data and the mean of the red data to the integrator. In some embodiments, the ingestible device 2500 may normalize the difference by the mean of the green data before adding it to the integrator. In some embodiments, the integrator will be incremented by one, rather than adding the difference between the green data and the red data. In some embodiments the integrator may also be periodically reset to zero, or reduced by a certain percentage each time the algorithm is performed. The ingestible device 2500 stores the value of the integrator, and uses this value to determine when a transition to the caecum has occurred.

At step 3216, the ingestible device 2500 compares the integrator to a detection threshold, to determine if a transition has occurred. In some embodiments the threshold value will be a multiple of the mean green or blue measurements, such as ten-times the mean green measurement. In some embodiments, when the integrator is incremented by one at the step 3214, or when the value added to the integrator at step 3214 has been normalized, the threshold value may be a predetermined number. In some embodiments the predetermined number may be based on how frequently sensor data is gathered, or it may be programmed into the device prior to being administered to a patient.

At step 3218, the ingestible device 2500 determines that a ileocaecal transition has occurred, and that the device is now in the caecum. This is done after the algorithm determines that the integrated difference between the mean red reflectance data and the mean green reflectance data is above a threshold value.

At step 3220, the ingestible device 2500 enters a deep sleep state. However, in some aspects the ingestible device 2500 may set an RTC oscillator alarm, which will wake the ingestible device 2500 from its sleep to take further data samples and perform additional localization algorithms if necessary.

It will be understood that the steps and descriptions of the flowcharts of this disclosure, including FIG. 32, are merely illustrative. Any of the steps and descriptions of the flowcharts, including FIG. 32, may be modified, omitted, rearranged, performed in alternate orders or in parallel, two or more of the steps may be combined, or any additional steps may be added, without departing from the scope of the present disclosure. For example, the ingestible device 2500 may calculate the mean and the standard deviation of multiple data sets in parallel in order to speed up the overall computation time. Furthermore, it should be noted that the steps and descriptions of FIG. 32 may be combined with any other system, device, or method described in this applications, and any of the ingestible devices or systems discussed in this application could be used to perform one or more of the steps in FIG. 32.

FIG. 33 is a flowchart illustrating some aspects of a duodenum detection algorithm used by the device. Although FIG. 33 may be described in connection with the ingestible device 2500 for illustrative purposes, this is not intended to be limiting, and either portions or the entirety of the duodenum detection process 3350 described in FIG. 33 may be applied to any device discussed in this application (e.g., the ingestible devices 10, 300, 302, 304, 306, 700, and 1900), and any of the ingestible devices may be used to perform one or more parts of the process described in FIG. 33. Furthermore, the features of FIG. 33 may be combined with any other systems, methods or processes described in this application. For example, portions of the algorithm described by the process in FIG. 33 may be integrated into the duodenum detection algorithm described by FIG. 24.

At step 3300, the ingestible device 2500 wakes up. The ingestible device 2500 will normally wake up at regular intervals, based on an RTC oscillator. Once the ingestible device 2500 wakes up, it will proceed with the rest of the process.

At step 3302, the ingestible device 2500 gathers and stores new sensor data points. The ingestible device 2500 starts by flashing different colored LEDs (e.g., the illuminators 1902a and 1902b) to produce illumination at red and green wavelengths. The ingestible device 2500 then detects (e.g, by detector 1904) the resulting reflectance and stores the data in memory.

At step 3304, the ingestible device 2500 loads the last "n" stored optical sensor values from flash memory (e.g., the flash storage 2704). The number of points "n" should be sufficiently large to calculate a statistically significant average and standard deviation, but in many aspects a value above 30 is chosen.

At step 3306, the ingestible device 2500 calculates intra-set standard deviations.

At step 3308, the ingestible device 2500 calculates intra-set mean values.

At step 3310, the ingestible device 2500 compares the red data to the green data. Similar to step 3212 (FIG. 32), in some embodiments this may involve subtracting a multiple of the red standard deviation from the mean of the red data, and subtracting a multiple of the green standard deviation from the mean of the green data. If the condition in step 3310 is not satisfied, the ingestible device 2500 may not consider that data point further.

At step 3312, the ingestible device 2500 increases the value of an integrator. Similar to step 3214 (FIG. 32), in some embodiments the ingestible device 2500 may add the difference between the mean of the green data and the mean of the red data to the integrator, and in some embodiments the integrator will be incremented by one, rather than adding the difference between the green data and the red data. The ingestible device 2500 may then use the stored value in the integrator to determine when a transition to the duodenum has occurred.

At step 3314, the ingestible device 2500 compares the integrator to a detection threshold, to determine if a transition has occurred. The threshold value may depend on a number of factors, such as those described in relation to step 3216 (FIG. 32). Additionally, the threshold may depend on the components used in the ingestible device 2500, and may vary based on the size of the detected signals.

At step 3316, the ingestible device 2500 determines that a pyloric transition has occurred, and that it is currently located in the duodenum. This is done after the algorithm determines that the integrated difference between the mean red reflectance data and the mean green reflectance data is above a threshold value.

At step 3318, the ingestible device 2500 enters a deep sleep state. However, in some aspects the ingestible device 2500 may set an RTC oscillator alarm, which will wake the ingestible device 2500 from its sleep to take further data samples and perform additional localization algorithms if necessary.

At step 3320, the ingestible device 2500 will reset the integrator to 0. In some aspects, this is done when the ingestible device 2500 determines that recently collected data is unreliable.

It will be understood that the steps and descriptions of the flowcharts of this disclosure, including FIG. 33, are merely illustrative. Any of the steps and descriptions of the flowcharts, including FIG. 33, may be modified, omitted, rearranged, performed in alternate orders or in parallel, two or more of the steps may be combined, or any additional steps may be added, without departing from the scope of the present disclosure. For example, the ingestible device 2500 may calculate the mean and the standard deviation of multiple data sets in parallel in order to speed up the overall computation time. Furthermore, it should be noted that the steps and descriptions of FIG. 33 may be combined with any other system, device, or method described in this applications, and any of the ingestible devices or systems discussed in this application could be used to perform one or more of the steps in FIG. 33.

Figure 34:
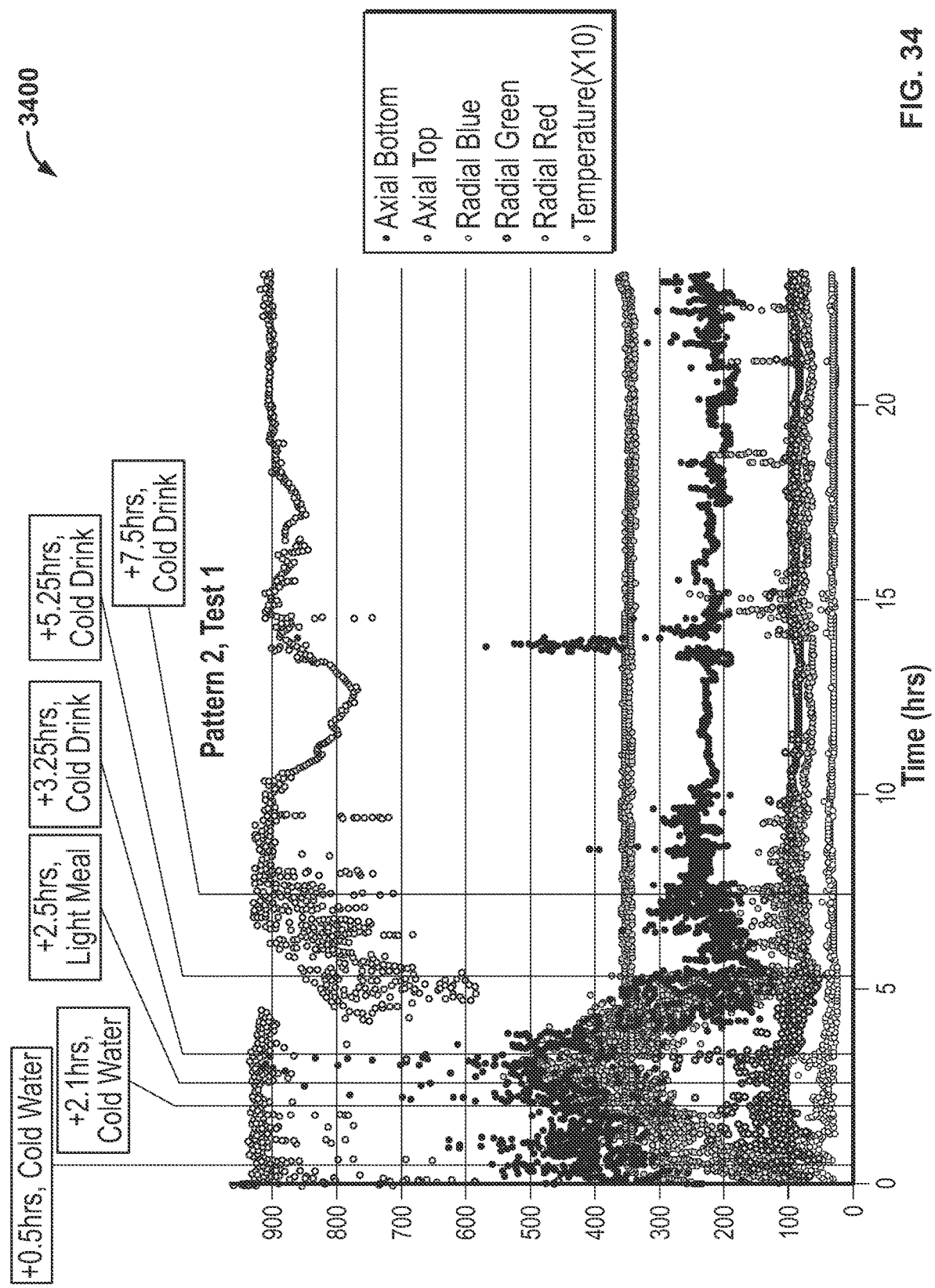
FIG. 34 is data from an ingestible device administered to a patient during a trial.

FIG. 34 is data from an example of fasted transit through an individual's GI tract in accordance with some embodiments of the device. Graph 3400 shows a sample set of data gathered by an ingestible device flashing different wavelengths of light as it transits through the gastrointestinal tract. This raw data shows an actual transit by an ingestible device configured similar to the ingestible device 1900, and acquiring data similar to the methods described in relation to FIGS. 21-24. FIG. 34 also shows consuming cold drinks and/or meals more than 30 minutes after ingesting the device do not alter the temperature readings of the device, indicating that the device exited the stomach before 30 minutes had passed.

Similar to the behavior shown in the green reflectance data 2426 and the blue reflectance data 2428 of FIG. 24, it can be seen that the radial green and radial blue data sets follow each-other closely, and follow similar patterns with a relatively flat detected value. Also, similar to the red reflectance data 2430 of FIG. 24, it can be seen that the red data set begins to diverge from the blue and green data sets quickly, around the one-hour mark, as the ingestible device 1900 undergoes a pyloric transition (e.g., pyloric transition 2416 (FIG. 24)). Between hours two-three, the response to the red wavelength illumination and the axial infrared illumination increases substantially, reaching an apex around the three-hour mark. This corresponds through transit through the duodenum (e.g., duodenum 2406 (FIG. 24)), reaching a treitz transition into the jejunum (e.g., treitz transition 2418 into jejunum 2408 (FIG. 24)). From hours three-five, the decrease in the detected red and axial infrared reflectance is consistent with transit through the jejunum, and an ileocaecal transition (e.g., ileocaecal transition 2420 (FIG. 24)) occurs near the five-hour mark. An increase in the response to the detected infrared reflectance relative to the red reflectance from the five-hour mark to the seven-hour mark is similarly consistent with a caecal transition into the large intestine (e.g., caecal transition 2422 into large intestine 2412 (FIG. 24)).

Figure 35:
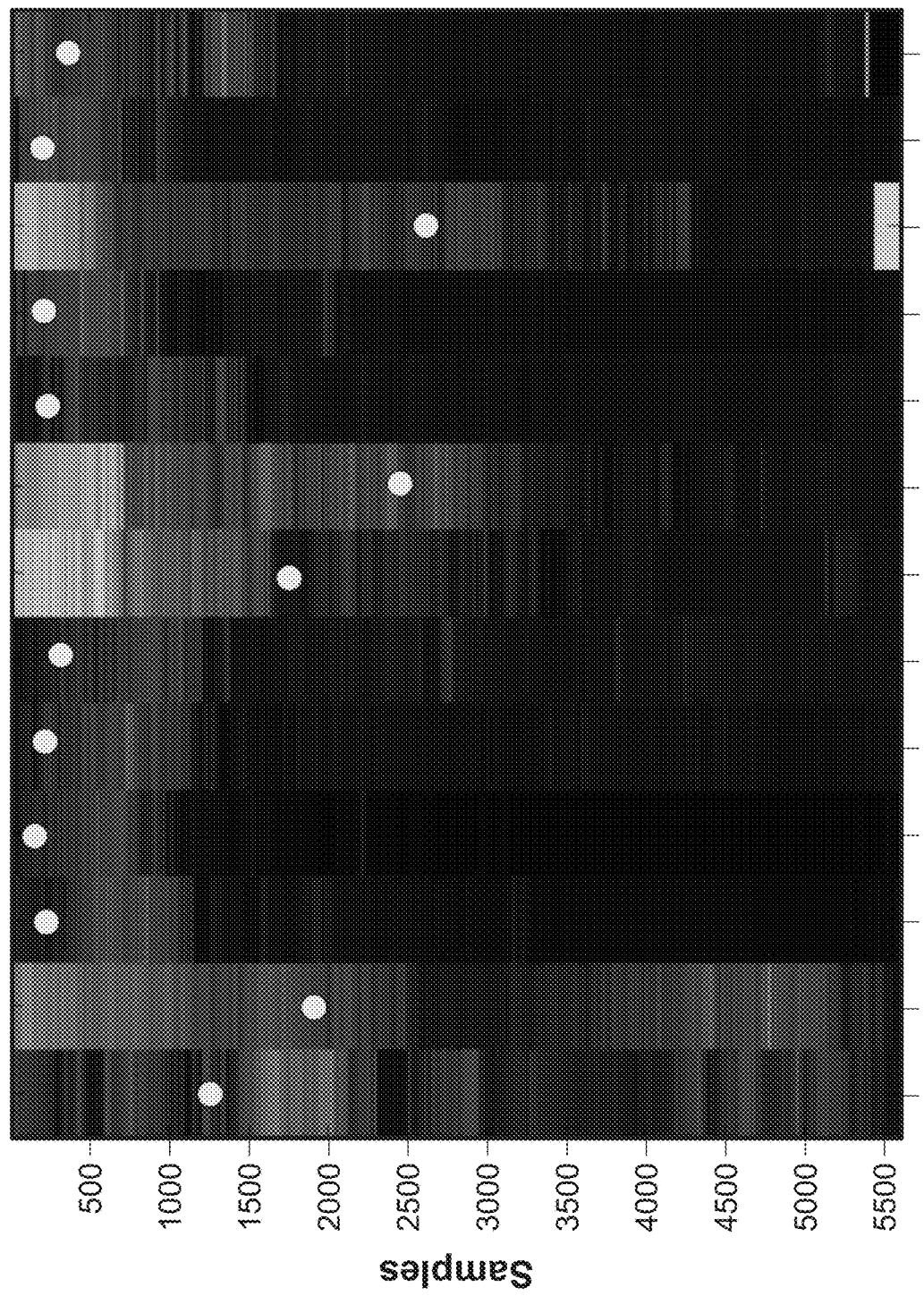
FIG. 35 is a color map, showing the changing levels of reflected light detected by the device in thirteen different trials.

FIG. 35 is a color map, showing the changing levels of reflected light detected by the device in 13 different trials. This corresponds to a set of tests conducted using an ingestible device similar to the ingestible device 1900. In FIG. 35, the data gathered from the red, green, and blue sensors were normalized, and combined into a single color post-hoc, after the ingestible device had been retrieved and the data extracted from the device. Each data set gathered from the detectors was mapped into a single hexadecimal color code, representing the relative size of the measured red, green and blue data in each data set. After mapping each data set into a single representative color, the graph 3400 was produced to shows the differences in the measured data as the device transits through the gastrointestinal tract. The graph 3400 displays the data gathered by an ingestible device in a number of human trials, wherein p1$t$3, p1$t$4, p2$t$1, p2$t$2, p2$t$5, p3$t$1, p3$t$3, p3$t$4 show fasted transit, and p1$t$1, p1$t$2, p2$t$3, p2$t$4, p3$t$2 show fed transit (i.e., subjects had recently consumed food). Note that the device itself does not function as a color imaging device, and graph 3400 is only presented for illustrative purposes.

In FIG. 35, earlier samples are shown at the top of the graph, and later samples shows towards the bottom. In general, a red shift is observed in nearly all cases of a pyloric transition. Some cases of delayed gastric emptying indicate greenish-yellow colors, and an unidentified meal of p2$t$3 shows varying purple/blue coloration between samples 100-700. Color shift due to exit from the body is shown from samples step 5400-5500 of p3$t$2, resulting in a generally light blue being detected. The determined location of the pyloric transition (e.g., the pyloric transition 2416 (FIG. 24)) from the stomach to the small intestine is shown with a small circle, and in general, it was found that an ingestible device was able to reliably identify portions of the gastrointestinal tract.

For illustrative purposes the examples given herein focus primarily on a number of different example embodiments of an ingestible device. However, the possible ingestible devices that may be constructed are not limited to these embodiments, and variations in the general shape and design may be made without significantly changing the functions and operations of the device. For example, some embodiments of the ingestible device may feature a sampling chamber substantially towards the middle of the device, along with two sets of axial sensing sub-units, each located on substantially opposite ends of the device. Also, the applications of the ingestible device are not limited merely to gathering data, sampling and testing portions of the gastrointestinal tract, or delivering medicament. For example, in some embodiments the ingestible device may be adapted to include a number of chemical, electrical, or optical diagnostics for diagnosing a number of diseases. Similarly, a number of different sensors for measuring bodily phenomenon or other physiological qualities may be included on the ingestible device. For example, the ingestible device may be adapted to measure elevated levels of certain chemical compounds or impurities in the gastrointestinal tract, or the combination of localization, sampling, and appropriate diagnostic and assay techniques incorporated into a sampling chamber may be particularly well suited to determine the presence of small intestinal bacterial overgrowth (SIBO).

At least some of the elements of the various embodiments of the ingestible device described herein that are implemented via software may be written in a high-level procedural language such as object oriented programming, a scripting language or both. Accordingly, the program code may be written in C, C++ or any other suitable programming language and may comprise modules or classes, as is known to those skilled in object oriented programming. Alternatively, or in addition, at least some of the elements of the embodiments of the ingestible device described herein that are implemented via software may be written in assembly language, machine language or firmware as needed. In either case, the language may be a compiled or an interpreted language.

At least some of the program code used to implement the ingestible device can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

Furthermore, at least some of the programs associated with the systems, devices, and methods of the example embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In some embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The various embodiments of systems, processes and apparatuses have been described herein by way of example only. It is contemplated that the features and limitations described in any one embodiment may be applied to any other embodiment herein, and flowcharts or examples relating to one embodiment may be combined with any other embodiment in a suitable manner, done in different orders, or done in parallel. It should be noted, the systems and/or methods described above may be applied to, or used in accordance with, other systems and/or methods. Various modifications and variations may be made to these example embodiments without departing from the spirit and scope of the embodiments, which is limited only by the appended claims. The appended claims should be given the broadest interpretation consistent with the description as a whole.

What is claimed is:

1. A method, comprising:
   for each of a plurality of times:
      transmitting light at a first wavelength from an ingestible device located in a gastrointestinal (GI) tract of a body;
      detecting a first amount of light at the first wavelength, the first amount of light having been reflected from an environment external to the ingestible device;
      storing a first value in a first data set, wherein the first value is indicative of the amount of detected light at the first wavelength;
      transmitting light at a second wavelength from the ingestible device located in the GI tract of the body, the second wavelength being different than the first wavelength;
      detecting a second amount of light at the second wavelength, the second amount of light having been reflected from the environment external to the ingestible device;
      storing a second value in a second data set, wherein the second value is indicative of the amount of detected light at the second wavelength; and
   determining a change in a location of the ingestible device within the GI tract of the body by comparing the first data set to the second data set.

2. The method of claim 1, wherein the first wavelength is in a red spectrum or an infrared spectrum.

3. The method of claim 2, wherein the second wavelength is in a blue spectrum or a green spectrum.

4. The method of claim 1, wherein the first wavelength is in a red spectrum.

5. The method of claim 4, wherein the second wavelength is in a green spectrum.

6. The method of claim 5, further comprising determining, based on the comparison of the first data set to the second data set, that the ingestible device has undergone an ileocecal transition.

7. The method of claim 5, further comprising determining, based on the comparison of the first data set to the second data set, that the ingestible device has undergone an ileocecal transition.

8. The method of claim 1, wherein comparing the first data set and the second data set comprises, for each of the plurality of times, taking a difference between the first value stored in the first data set and the second value stored in the second data set.

9. The method of claim 1, wherein comparing the first data set and the second data set comprises taking a difference between a mean of the plurality of first values stored in the first data set a mean of the plurality of second values stored in the second data set.

10. The method of claim 1, further comprising incrementing a counter when a mean of the first data set less a multiple of a standard deviation of the first data set is greater than a mean of the second data set plus a multiple of a standard deviation of the second data set.

11. An ingestible device, comprising:
   a housing;
   one or more sensing sub-units configured to, at each of a plurality of times:
      transmit a first wavelength of light towards an environment external to the housing;
      detect the first wavelength of light after it has reflected from the environment external to the housing;

transmit a second wavelength of light towards the environment external to the housing, the second wavelength being different from the first wavelength; and detect the second wavelength of light after it has reflected from the environment external to the housing; and a microcontroller configured to, for each of the plurality of times:

store a first value in a first data set, wherein the first value is indicative of an amount of light detected by the device at the first wavelength;

store a second value in a second data set, wherein the second value is indicative of an amount of light detected by the device at the second wavelength; and determine a change in a location of the ingestible device within the gastrointestinal (GI) tract of the body by comparing the first data set to the second data set.

12. The ingestible device of claim 11, wherein the first wavelength is in a red spectrum or an infrared spectrum.

13. The ingestible device of claim 12, wherein the second wavelength is in a blue spectrum or a green spectrum.

14. The ingestible device of claim 11, wherein the first wavelength is in a red spectrum.

15. The ingestible device of claim 14, wherein the second wavelength is in a green spectrum.

16. The ingestible device of claim 15, wherein the one or more sensing sub-units are configured to determine that the ingestible device has undergone an ileocecal transition.

17. The ingestible device of claim 11, wherein the one or more sensing sub-units are configured to determine that the ingestible device has undergone a transition selected from the group consisting of a pyloric transition, a treitz transition, an ileocecal transition and a cecal transition.

18. The ingestible device of claim 11, wherein the comparison of the first data set and the second data set comprises, for each of the plurality of times, a difference between the first value stored in the first data set and the second value stored in the second data set.

19. The ingestible device of claim 11, wherein the comparison of the first data set and the second data set comprises a difference between a mean of the plurality of first values stored in the first data set and a mean of the plurality of second values stored in the second data set.

20. The ingestible device of claim 11, wherein the comparison of the first data set and the second data set comprises a comparison of a mean of the plurality of first values stored in the first data set less a multiple of a standard deviation of the first data set and a mean of the plurality of second values stored in the second data set plus a multiple of a standard deviation of the second data set.

21. The ingestible device of claim 11, wherein the housing is defined by a first end, a second end substantially opposite from the first end, and a radial wall extending longitudinally from the first end to the second end, wherein the one or more sensing sub-units comprise a sensor array, the sensor array comprising a plurality of radial detectors and a plurality of radial illuminators.

22. The ingestible device of claim 21, wherein the sensor array comprises at least one radial sensor having a radial illuminator configured to transmit the second wavelength and a radial detector configured to detect the second wavelength.

23. The ingestible device of claim 21, wherein the sensor array comprises three radial sensors, each comprising a radial detector, the radial illuminator and the radial detector of a given radial sensor being disposed approximately 60 degrees from each other along a circumference of the radial wall.

24. The ingestible device of claim 11, wherein the microcontroller is further configured to store the plurality of first values in the first data set and the plurality of second values in the second data set at periodic intervals.

25. A method, comprising:

i) generating a first data set comprising a plurality of first values, each first value being stored in the first data set by a method comprising:

transmitting light at a first wavelength from an ingestible device located in a gastrointestinal (GI) tract of a body;

detecting a first amount of light at the first wavelength, the first amount of light having been reflected from an environment external to the ingestible device; and storing the first value in the first data set, wherein the first value is indicative of the amount of detected light at the first wavelength;

ii) generating a second data set comprising a plurality of second values, each second value being stored in the second data set by a method comprising:

transmitting light at a second wavelength from the ingestible device located in the GI tract of the body, the second wavelength being different than the first wavelength;

detecting a second amount of light at the second wavelength, the second amount of light having been reflected from the environment external to the ingestible device;

storing the second value in the second data set, wherein the second value is indicative of the amount of detected light at the second wavelength; and iii) determining a change in a location of the ingestible device within the GI tract of the body by comparing the first data set to the second data set.

26. The method of claim 25, wherein comparing the first data set and the second data set comprises integrating a difference between values stored in the first data set and values stored in the second data set.

27. The method of claim 25, wherein comparing the first data set and the second data set comprises integrating a difference between a moving average of the first data set and a moving average of the second data set.

28. The method of claim 25, wherein comparing the first data set and the second data set comprises taking a difference between each first value stored in the first data set and each corresponding second value stored in the second data set.

29. The method of claim 25, wherein comparing the first data set and the second data set comprises taking a difference between a mean of the plurality of first values stored in the first data set and a mean of the plurality of second values stored in the second data set.

30. The method of claim 25, further comprising incrementing a counter when a mean of the first data set less a multiple of a standard deviation of the first data set is greater than a mean of the second data set plus a multiple of a standard deviation of the second data set.

31. An ingestible device, comprising:

a housing;

one or more sensing sub-units configured to iteratively:

transmit a first wavelength of light towards an environment external to the housing;

for each iteration of transmitting the first wavelength of light, detect the first wavelength of light after it has reflected from the environment external to the housing;

transmit a second wavelength of light towards the environment external to the housing, the second wavelength being different from the first wavelength; and for each iteration of transmitting the second wavelength of light, detect the second wavelength of light after it has reflected from the environment external to the housing; and a microcontroller configured to:

generate a first data set comprising a plurality of first values, wherein each first value is indicative of an amount of light detected by the device at the first wavelength for a corresponding iteration detecting the first wavelength of light after it has reflected from the environment external to the housing;

generate a second data set comprising a plurality of second values, wherein each second value is indicative of an amount of light detected by the device at the second wavelength for a corresponding iteration of detecting the second wavelength of light after it has reflected from the environment external to the housing; and determine a change in a location of the ingestible device within the gastrointestinal (GI) tract of the body by comparing the first data set to the second data set.

32. The ingestible device of claim 31, wherein the comparison of the first data set and the second data set comprises an integrated difference between values stored in the first data set and values stored in the second data set.

33. The ingestible device of claim 31, wherein the comparison of the first data set and the second data set comprises an integrated difference between a moving average of the first data set and a moving average of the second data set.

34. The ingestible device of claim 31, wherein the comparison of the first data set and the second data set comprises, for each iteration, a difference between the first value stored in the first data set and the second value stored in the second data set.

35. The ingestible device of claim 31, wherein the comparison of the first data set and the second data set comprises a difference between a mean of the plurality of first values stored in the first data set and a mean of the plurality of second values stored in the second data set.

36. The ingestible device of claim 31, wherein the comparison of the first data set and the second data set comprises a comparison of a mean of the plurality of first values stored in the first data set less a multiple of a standard deviation of the first data set and a mean of the plurality of second values stored in the second data set plus a multiple of a standard deviation of the second data set.

37. The ingestible device of claim 31, wherein the microcontroller is further configured to store the plurality of first values in the first data set and the plurality of second values in the second data set at periodic intervals.

\* \* \* \* \*

UNITED STATES PATENT AND TRADEMARK OFFICE
CERTIFICATE OF CORRECTION

Page 1 of 2

PATENT NO. : 10,835,152 B2
APPLICATION NO. : 15/514413
DATED : November 17, 2020
INVENTOR(S) : Mitchell Lawrence Jones et al.

It is certified that error appears in the above-identified patent and that said Letters Patent is hereby corrected as shown below:

On the Title Page

Page 3, Column 1 (Other Publications), Line 18, delete "om" and insert -- For --;

Page 3, Column 2 (Other Publications), Line 37, delete "Exoeriments," and insert -- Experiments, --;

Page 3, Column 2 (Other Publications), Line 40, delete "Suoolements," and insert -- Supplements, --;

In the Specification

Column 8, Line 49, delete "herein" and insert -- herein. --;

Column 8, Line 49, delete "a housing" and insert -- A housing --;

Column 15, Line 39, delete "Alibr™" and insert -- Alibre™ --;

Column 18, Line 34, after "can" delete "be";

Column 19, Line 44, delete "218*b*, 218*b*" and insert -- 218*a*, 218*b* --;

Column 22, Line 21, delete "that that" and insert -- that --;

Column 31, Line 45, delete "FIGS. 6A to 6C" and insert -- FIGS. 6A to 6B --;

Column 36, Line 46, delete "approximately) 60°" and insert -- approximately 60°) --;

Column 46, Line 48, delete "RDB" and insert -- RGB --;

Column 50, Line 67, delete "trietz" and insert -- treitz --;

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,835,152 B2

Column 56, Line 40, delete "LARGE_INTESTINE" and insert -- LARGE INTESTINE --;

Column 57, Line 19, delete "ILIEUM," and insert -- ILEUM, --;

Column 57, Line 20, after "also" insert -- be --;

Column 67, Line 25, delete "properly" and insert -- properly. --;

In the Claims

Column 78, Line 41, Claim 7, delete "claim 5," and insert -- claim 1, --;

Column 78, Lines 43-44, Claim 7, delete "an ileocecal transition." and insert -- a transition selected from the group consisting of a pyloric transition, a treitz transition, an ileocecal transition and a cecal transition. --.